United States Patent
Heo et al.

(10) Patent No.: US 11,450,819 B2
(45) Date of Patent: Sep. 20, 2022

(54) HETEROCYCLIC COMPOUND AND ORGANIC LIGHT-EMITTING ELEMENT INCLUDING SAME

(71) Applicant: LG Chem, Ltd., Seoul (KR)

(72) Inventors: Dong Uk Heo, Daejeon (KR); Dong Hoon Lee, Daejeon (KR); Jungoh Huh, Daejeon (KR); Boonjae Jang, Daejeon (KR); Yongbum Cha, Daejeon (KR); Miyeon Han, Daejeon (KR); Junghoon Yang, Daejeon (KR); Heekyung Yun, Daejeon (KR)

(73) Assignee: LG Chem, Ltd.

( * ) Notice: Subject to any disclaimer, the term of this patent is extended or adjusted under 35 U.S.C. 154(b) by 467 days.

(21) Appl. No.: 16/484,641

(22) PCT Filed: Apr. 13, 2018

(86) PCT No.: PCT/KR2018/004317
§ 371 (c)(1),
(2) Date: Aug. 8, 2019

(87) PCT Pub. No.: WO2018/190666
PCT Pub. Date: Oct. 18, 2018

(65) Prior Publication Data
US 2019/0355915 A1 Nov. 21, 2019

(30) Foreign Application Priority Data
Apr. 13, 2017 (KR) .......... 10-2017-0047933

(51) Int. Cl.
*H01L 51/00* (2006.01)
*C07D 405/10* (2006.01)
(Continued)

(52) U.S. Cl.
CPC ........ *H01L 51/0073* (2013.01); *C07D 405/04* (2013.01); *C07D 405/10* (2013.01); *C07D 413/04* (2013.01); *C07D 413/10* (2013.01); *C07D 417/10* (2013.01); *C07D 471/04* (2013.01); *C09K 11/06* (2013.01);
(Continued)

(58) Field of Classification Search
None
See application file for complete search history.

(56) References Cited

U.S. PATENT DOCUMENTS

2004/0219386 A1 11/2004 Thoms
2004/0251816 A1 12/2004 Leo et al.
(Continued)

FOREIGN PATENT DOCUMENTS

CN 102786508 A 11/2012
CN 103666455 A 3/2014
(Continued)

OTHER PUBLICATIONS

International Search Report from Application No. PCT/KR2018/004317 dated Aug. 20, 2018, 3 pages.
(Continued)

*Primary Examiner* — Jay Yang
(74) *Attorney, Agent, or Firm* — Lerner, David, Littenberg, Krumholz & Mentlik, LLP

(57) ABSTRACT

The present specification relates to a heterocyclic compound represented by Chemical Formula 1 and an organic light emitting device comprising the same.

18 Claims, 3 Drawing Sheets

(51) Int. Cl.
*C09K 11/06* (2006.01)
*C07D 471/04* (2006.01)
*C07D 413/04* (2006.01)
*C07D 405/04* (2006.01)
*C07D 417/10* (2006.01)
*C07D 413/10* (2006.01)
*H01L 51/50* (2006.01)

(52) U.S. Cl.
CPC ........ *H01L 51/007* (2013.01); *H01L 51/0069* (2013.01); *H01L 51/0072* (2013.01); *C09K 2211/1018* (2013.01); *H01L 51/5072* (2013.01); *H01L 51/5076* (2013.01); *H01L 51/5092* (2013.01)

(56) References Cited

U.S. PATENT DOCUMENTS

| | | | |
|---|---|---|---|
| 2015/0115241 A1 | 4/2015 | Zoellner et al. | |
| 2016/0118599 A1 | 4/2016 | Jeong et al. | |
| 2017/0162800 A1 | 6/2017 | Zoellner et al. | |
| 2017/0222157 A1 | 8/2017 | Jatsch et al. | |
| 2018/0337341 A1 | 11/2018 | Heo et al. | |

FOREIGN PATENT DOCUMENTS

| | | |
|---|---|---|
| CN | 104193738 A | 12/2014 |
| CN | 105884830 A | 8/2016 |
| EP | 3366682 A1 | 8/2018 |
| JP | 200396072 A | 4/2003 |
| JP | 2019500326 A | 1/2019 |
| KR | 20130140303 A | 12/2013 |
| KR | 20150002740 A | 1/2015 |
| KR | 20150106501 A | 9/2015 |
| KR | 101593368 B1 | 2/2016 |
| KR | 20170032414 A | 3/2017 |
| KR | 101755986 B1 | 7/2017 |
| WO | 2016012075 A1 | 1/2016 |
| WO | 2017146466 A1 | 8/2017 |

OTHER PUBLICATIONS

Extended European Search Report including Written Opinion for Application No. EP18784378.4 dated Dec. 19, 2019.

[FIG. 1]
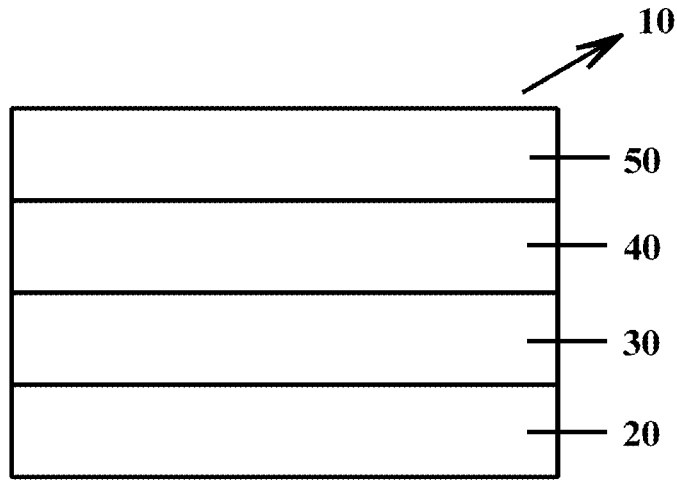
[FIG. 2]
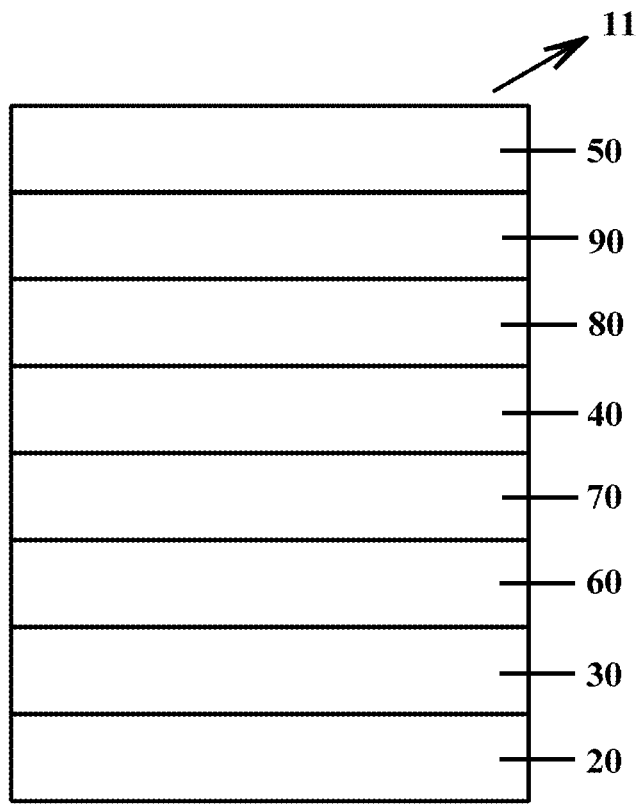

[FIG. 3]
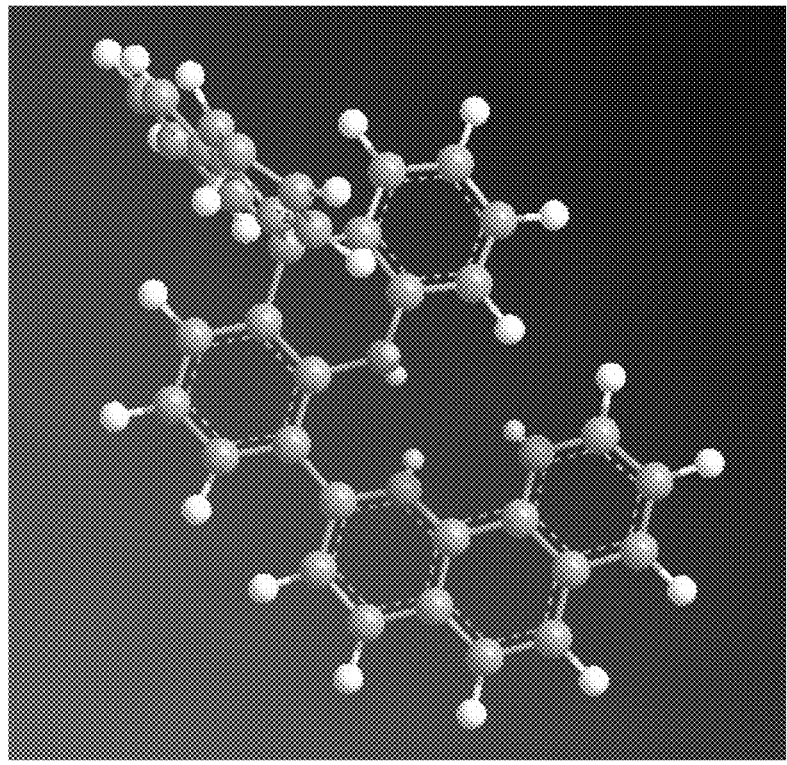
[FIG. 4]
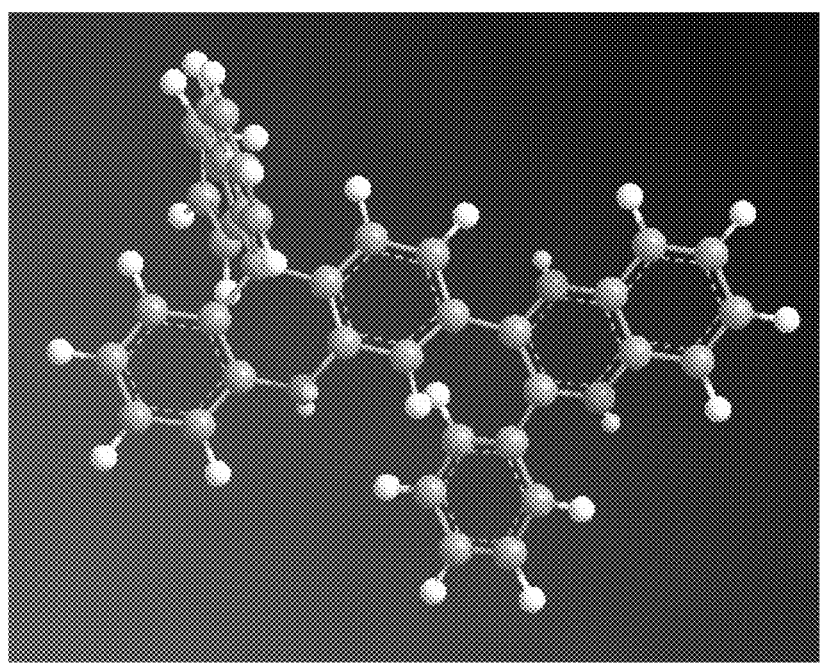

[FIG. 5]
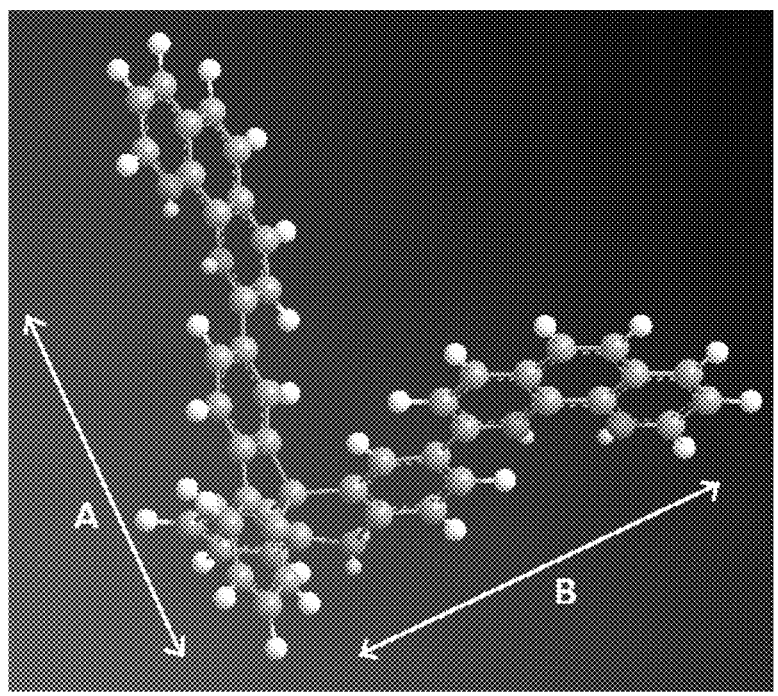
[FIG. 6]
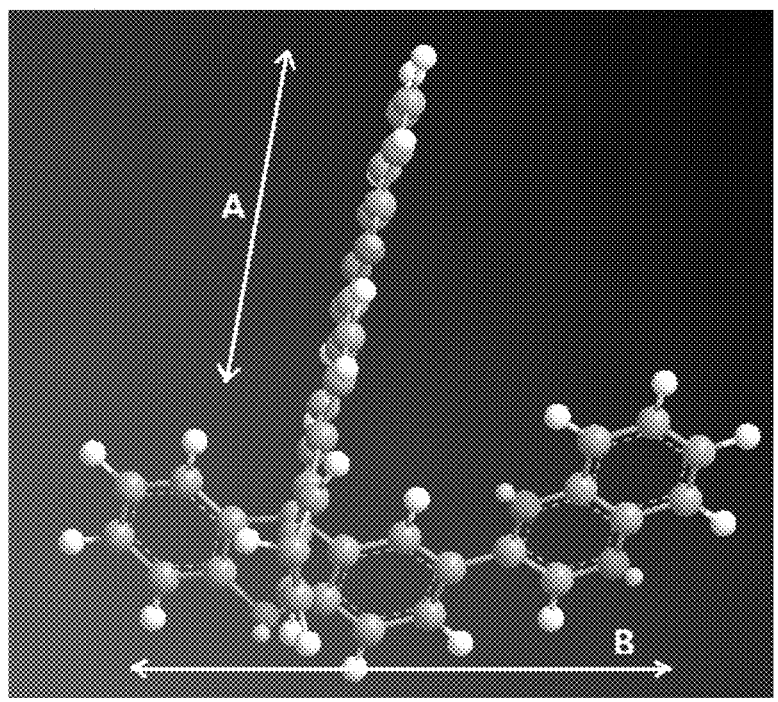

HETEROCYCLIC COMPOUND AND ORGANIC LIGHT-EMITTING ELEMENT INCLUDING SAME

CROSS-REFERENCE TO RELATED APPLICATIONS

The present application is a national phase entry under 35 U.S.C. § 371 of International Application No. PCT/KR2018/004317 filed Apr. 13, 2018, which claims priority from Korean Patent Application No. 10-2017-0047933 filed Apr. 13, 2017, all of which are incorporated herein by reference.

TECHNICAL FIELD

The present specification relates to a heterocyclic compound and an organic light emitting device comprising the same.

BACKGROUND ART

An organic light emission phenomenon generally refers to a phenomenon converting electrical energy to light energy using an organic material. An organic light emitting device using an organic light emission phenomenon normally has a structure comrising an anode, a cathode, and an organic material layer therebetween. Herein, the organic material layer is often formed in a multilayer structure formed with different materials in order to increase efficiency and stability of the organic light emitting device, and for example, may be formed with a hole injection layer, a hole transfer layer, a light emitting layer, an electron transfer layer, an electron injection layer and the like. When a voltage is applied between the two electrodes in such an organic light emitting device structure, holes and electrons are injected to the organic material layer from the anode and the cathode, respectively, and when the injected holes and electrons meet, excitons are formed, and light emits when these excitons fall back to the ground state.

Development of new materials for such an organic light emitting device has been continuously required.

DISCLOSURE

Technical Problem

The present specification is directed to providing a heterocyclic compound having excellent electron transfer, electron injection and electron control abilities, and, when used in an organic material layer of an organic light emitting device, particularly, an electron injection layer, an electron transfer layer, a layer carrying out electron transfer and injection at the same time or an electron control layer, thereby lowering a driving voltage, increasing light emission efficiency or enhancing lifetime properties of the device, and an organic light emitting device comprising the same.

Technical Solution

One embodiment of the present specification provides a heterocyclic compound represented by the following Chemical Formula 1.

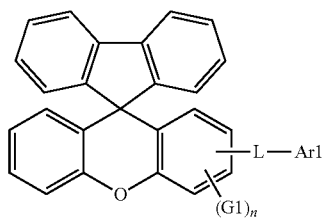

[Chemical Formula 1]

In Chemical Formula 1,
G1 is hydrogen; deuterium; a nitrile group; a nitro group; a hydroxyl group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group,
L is a direct bond; or a substituted or unsubstituted arylene group,
Ar1 is a substituted or unsubstituted heteroring comprising two or more Ns, and
n is an integer of 0 to 3, and when n is 2 or greater, structures in the two or more parentheses are the same as or different from each other.

Another embodiment of the present specification provides an organic light emitting device comprising a first electrode; a second electrode provided opposite to the first electrode; and one or more organic material layers provided between the first electrode and the second electrode, wherein the heterocyclic compound represented by Chemical Formula 1 is comprised in one or more layers of the one or more organic material layers.

Advantageous Effects

A heterocyclic compound according to one embodiment of the present specification can be used as a material of an organic material layer of an organic light emitting device, and by using the same, efficiency can be enhanced, a driving voltage can be lowered, and/or life properties can be enhanced in the organic light emitting device.

DESCRIPTION OF DRAWINGS

FIG. 1 illustrates an organic light emitting device (10) according to one embodiment of the present specification.
FIG. 2 illustrates an organic light emitting device (11) according to another embodiment of the present specification.
FIG. 3 illustrates a molecular 3D structure for Compound E3 according to one embodiment of the present specification using Chem 3D Pro.
FIG. 4 illustrates a molecular 3D structure for Compound E6 according to one embodiment of the present specification using Chem 3D Pro.

FIG. 5 illustrates a molecular 3D structure for Compound [ET-1-E] using Chem 3D Pro.

FIG. 6 illustrates a molecular 3D structure for Compound [ET-1-I] using Chem 3D Pro.

REFERENCE NUMERAL 10, 11: Organic Light Emitting Device
20: Substrate
30: First Electrode
40: Light Emitting Layer
50: Second Electrode
60: Hole Injection Layer
70: Hole Transfer Layer
80: Electron Transfer Layer
90: Electron Injection Layer

MODE FOR DISCLOSURE

Hereinafter, the present specification will be described in more detail.

One embodiment of the present specification provides a heterocyclic compound represented by Chemical Formula 1.

The heterocyclic compound according to one embodiment of the present specification has a nonlinear structure, and efficiency enhancement, low driving voltage, lifetime property enhancement and/or the like are capable of being obtained in an organic light emitting device. In addition, by the substituent Ar1 having an electron depleted-structured substituent in the structure of the heterocyclic compound represented by Chemical Formula 1, a dipole moment of the molecule may be designed close to nonpolar, and therefore, an amorphous layer may be formed when manufacturing an organic light emitting device comprising the heterocyclic compound represented by Chemical Formula 1. Accordingly, in an organic light emitting device comprising the heterocyclic compound according to one embodiment of the present specification, efficiency enhancement, low driving voltage, lifetime property enhancement and the like are capable of being obtained.

Particularly, the compound of Chemical Formula 1 has a substituent in only one benzene in the core structure, and, particularly when there is one substituent, has a three-dimensionally horizontal structure as well has having the electronic properties described above, and therefore, electron mobility is strengthened when forming an organic material layer using such a material.

When two or more benzenes in the core structure of Chemical Formula 1 are each substituted with substituents, such a horizontal structure is not obtained, and therefore, electron mobility is low compared to the compound of the present disclosure.

In the present specification, a description of a certain part "comprising" certain constituents means capable of further including other constituents, and does not exclude other constituents unless particularly stated on the contrary.

In the present specification, a description of one member being placed "on" another member includes not only a case of the one member adjoining the another member but a case of still another member being present between the two members.

Examples of the substituents in the present specification are described below, however, the substituents are not limited thereto.

The term "substitution" means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents may be the same as or different from each other.

The term "substituted or unsubstituted" in the present specification means being substituted with one, two or more substituents selected from the group consisting of deuterium; a halogen group; a nitrile group; a nitro group; an imide group; an amide group; a carbonyl group; an ester group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; and a substituted or unsubstituted heteroaryl group, or being substituted with a substituent linking two or more substituents among the substituents illustrated above, or having no substituents. For example, "a substituent linking two or more substituents" may include a biphenyl group. In other words, a biphenyl group may be an aryl group, or interpreted as a substituent linking two phenyl groups.

In the present specification,

means a site bonding to other substituents or bonding sites.

In the present specification, the halogen group may include fluorine, chlorine, bromine or iodine.

In the present specification, the number of carbon atoms of the imide group is not particularly limited, but is preferably from 1 to 30. Specifically, compounds having structures as below may be included, however, the imide group is not limited thereto.

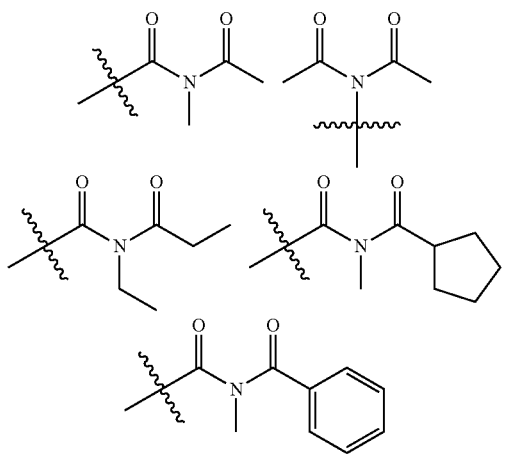

In the present specification, in the amide group, the nitrogen of the amide group may be substituted with a linear, branched or cyclic alkyl group having 1 to 30 carbon atoms or an aryl group having 6 to 30 carbon atoms. Specifically, compounds having the following structural formulae may be included, however, the amide group is not limited thereto.

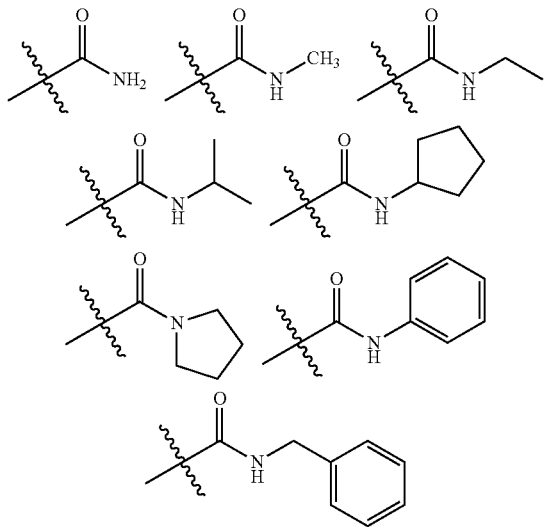

In the present specification, the number of carbon atoms of the carbonyl group is not particularly limited, but is preferably from 1 to 30. Specifically, compounds having structures as below may be included, however, the carbonyl group is not limited thereto.

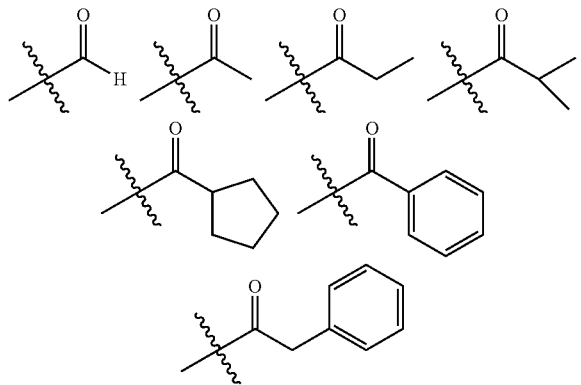

In the present specification, in the ester group, the oxygen of the ester group may be substituted with a linear, branched or cyclic alkyl group having 1 to 25 carbon atoms or an aryl group having 6 to 30 carbon atoms. Specifically, compounds having the following structural formulae may be included, however, the ester group is not limited thereto.

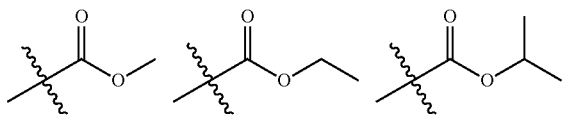

-continued

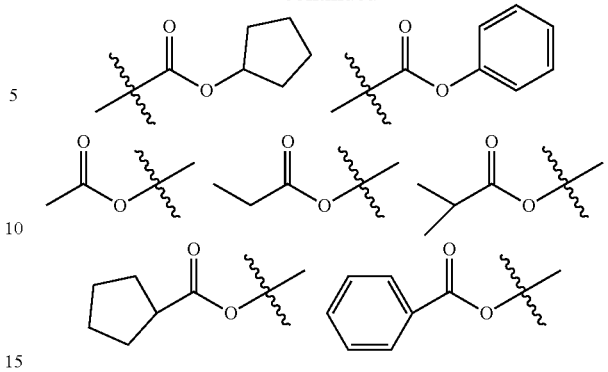

In the present specification, the alkyl group may be linear or branched, and although not particularly limited thereto, the number of carbon atoms is preferably from 1 to 30. Specifically, the number of carbon atoms is preferably from 1 to 20. More specifically, the number of carbon atoms is preferably from 1 to 10. Specific examples thereof may include a methyl group; an ethyl group; a propyl group; an n-propyl group; an isopropyl group; a butyl group; an n-butyl group; an isobutyl group; a tert-butyl group; a sec-butyl group; a 1-methylbutyl group; a 1-ethylbutyl group; a pentyl group; an n-pentyl group; an isopentyl group; a neopentyl group; a tert-pentyl group; a hexyl group; an n-hexyl group; a 1-methylpentyl group; a 2-methylpentyl group; a 3,3-dimethylbutyl group; a 2-ethylbutyl group; a heptyl group; an n-heptyl group; a 1-methylhexyl group; a cyclopentylmethyl group; a cyclohexylmethyl group; an octyl group; an n-octyl group; a tert-octyl group; a 1-methylheptyl group; a 2-ethylhexyl group; a 2-propylpentyl group; an n-nonyl group; a 2,2-dimethylheptyl group; a 1-ethylpropyl group; a 1,1-dimethylpropyl group; an isohexyl group; a 2-methylpentyl group; a 4-methylhexyl group; a 5-methylhexyl group and the like, but are not limited thereto.

In the present specification, the cycloalkyl group is not particularly limited, but preferably has 3 to 30 carbon atoms, and more preferably has 3 to 20 carbon atoms. Specific examples thereof may include a cyclopropyl group; a cyclobutyl group; a cyclopentyl group; a 3-methylcyclopentyl group; a 2,3-dimethylcyclopentyl group; a cyclohexyl group; a 3-methylcyclohexyl group; a 4-methylcyclohexyl group; a 2,3-dimethylcyclohexyl group; a 3,4,5-trimethylcyclohexyl group; a 4-tert-butylcyclohexyl group; a cycloheptyl group; a cyclooctyl group and the like, but are not limited thereto.

In the present specification, the alkoxy group may be linear, branched or cyclic. The number of carbon atoms of the alkoxy group is not particularly limited, but is preferably from 1 to 30. Specifically, the number of carbon atoms is preferably from 1 to 20. More specifically, the number of carbon atoms is preferably from 1 to 10. Specific examples thereof may include a methoxy group; an ethoxy group; an n-propoxy group; an isopropoxy group; an n-butoxy group; an isobutoxy group; a tert-butoxy group; a sec-butoxy group; an n-pentyloxy group; a neopentyloxy group; an isopentyloxy group; an n-hexyloxy group; a 3,3-dimethylbutyloxy group; a 2-ethylbutyloxy group; an n-octyloxy group; an n-nonyloxy group; an n-decyloxy group; a benzyloxy group; a p-methylbenzyloxy group and the like, but are not limited thereto.

In the present specification, the amine group may be selected from the group consisting of —NH₂; an alkylamine group; an N-alkylarylamine group; an arylamine group; an N-arylheteroarylamine group; an N-alkylheteroarylamine group and a heteroarylamine group, and the number of carbon atoms is, although not particularly limited thereto, preferably from 1 to 30. Specific examples of the amine group may include a methylamine group; a dimethylamine group; an ethylamine group; a diethylamine group; a phenylamine group; a naphthylamine group; a biphenylamine group; an anthracenylamine group; a 9-methylanthracenylamine group; a diphenylamine group; an N-phenylnaphthylamine group; a ditolylamine group; an N-phenyltolylamine group; a triphenylamine group; an N-phenylbiphenylamine group; an N-phenylnaphthylamine group; an N-biphenylnaphthylamine group; an N-naphthylfluorenylamine group; an N-phenylphenanthrenylamine group; an N-biphenylphenanthrenylamine group; an N-phenylfluorenylamine group; an N-phenylterphenylamine group; an N-phenanthrenylfluorenylamine group; an N-biphenylfluorenylamine group and the like, but are not limited thereto.

In the present specification, the N-alkylarylamine group means an amine group in which N of the amine group is substituted with an alkyl group and an aryl group.

In the present specification, the N-arylheteroarylamine group means an amine group in which N of the amine group is substituted with an aryl group and a heteroaryl group.

In the present specification, the N-alkylheteroarylamine group means an amine group in which N of the amine group is substituted with an alkyl group and a heteroaryl group.

In the present specification, the alkyl group in the alkylamine group, the N-arylalkylamine group, the alkylthioxy group, the alkylsulfoxy group and the N-alkylheteroarylamine group is the same as the examples of the alkyl group described above. Specifically, the alkylthioxy group may include a methylthioxy group; an ethylthioxy group; a tert-butylthioxy group; a hexylthioxy group; an octylthioxy group and the like, and the alkylsulfoxy group may include mesyl; an ethylsulfoxy group; a propylsulfoxy group; a butylsulfoxy group and the like, however, the alkythoixy group and the alkylsulfoxy group are not limited thereto.

In the present specification, the alkenyl group may be linear or branched, and although not particularly limited thereto, the number of carbon atoms is preferably from 2 to 30. Specific examples thereof may include a vinyl group; a 1-propenyl group; an isopropenyl group; a 1-butenyl group; a 2-butenyl group; a 3-butenyl group; a 1-pentenyl group; a 2-pentenyl group; a 3-pentenyl group; a 3-methyl-1-butenyl group; a 1,3-butadienyl group; an allyl group; a 1-phenylvinyl-1-yl group; a 2-phenylvinyl-1-yl group; a 2,2-diphenylvinyl-1-yl group; a 2-phenyl-2-(naphthyl-1-yl)vinyl-1-yl group; a 2,2-bis(diphenyl-1-yl)vinyl-1-yl group; a stilbenyl group; a styrenyl group and the like, but are not limited thereto.

In the present specification, the silyl group may be represented by a chemical formula of —SiRaRbRc, and Ra, Rb and Rc may each be hydrogen; a substituted or unsubstituted alkyl group; or a substituted or unsubstituted aryl group. Specific examples of the silyl group may include a trimethylsilyl group; a triethylsilyl group; a t-butyldimethylsilyl group; a vinyldimethylsilyl group; a propyldimethylsilyl group; a triphenylsilyl group; a diphenylsilyl group; a phenylsilyl group and the like, but are not limited thereto.

In the present specification, the boron group may be —$BR_{100}R_{101}$, and $R_{100}$ and $R_{101}$ are the same as or different from each other, and may be each independently selected from the group consisting of hydrogen; deuterium; a halogen group; a nitrile group; a substituted or unsubstituted monocyclic or multicyclic cycloalkyl group having 3 to 30 carbon atoms; a substituted or unsubstituted linear or branched alkyl group having 1 to 30 carbon atoms; a substituted or unsubstituted monocyclic or multicyclic aryl group having 6 to 30 carbon atoms; and a substituted or unsubstituted monocyclic or multicyclic heteroaryl group having 2 to 30 carbon atoms.

In the present specification, specific examples of the phosphine oxide group may include a diphenylphosphine oxide group; a dinaphthylphosphine oxide group and the like, but are not limited thereto.

In the present specification, the aryl group is not particularly limited, but preferably has 6 to 30 carbon atoms, and more preferably has 6 to 20 carbon atoms. The aryl group may be monocyclic or multicyclic.

When the aryl group is a monocyclic aryl group, the number of carbon atoms is not particularly limited, but is preferably from 6 to 30. Specific examples of the monocyclic aryl group may include a phenyl group; a biphenyl group; a terphenyl group and the like, but are not limited thereto.

When the aryl group is a multicyclic aryl group, the number of carbon atoms is not particularly limited, but is preferably from 10 to 30. Specific examples of the multicyclic aryl group may include a naphthyl group; an anthracenyl group; a phenanthrenyl group; a triphenylenyl group; a pyrenyl group; a phenalenyl group; a perylenyl group; a chrysenyl group; a fluorenyl group and the like, but are not limited thereto.

In the present specification, the fluorenyl group may be substituted, and adjacent substituents may bond to each other to form a ring.

When the fluorenyl group is substituted,

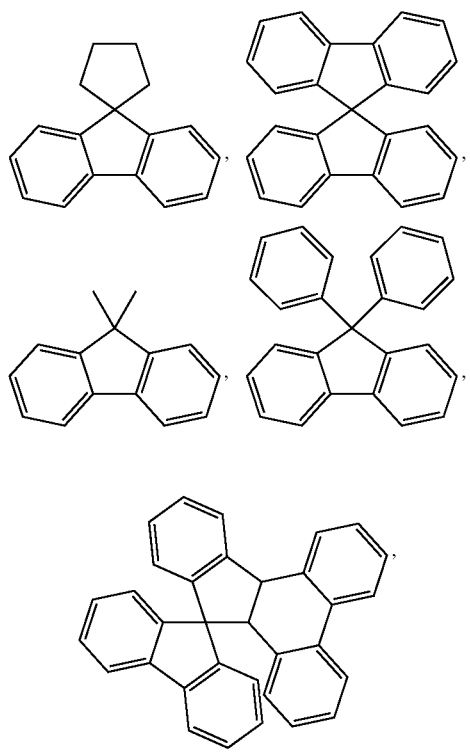

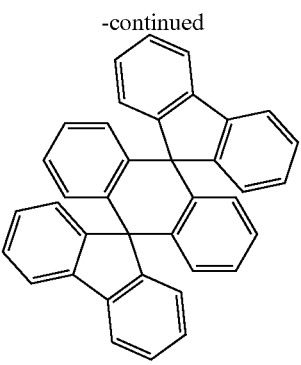

and the like may be included. However, the compound is not limited thereto.

In the present specification, an "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

In the present specification, the aryl group in the aryloxy group, the arylthioxy group, the arylsulfoxy group, the N-arylalkylamine group, the N-arylheteroarylamine group and the arylphosphine group is the same as the examples of the aryl group described above. Specific examples of the aryloxy group may include a phenoxy group; a p-tolyloxy group; an m-tolyloxy group; a 3,5-dimethylphenoxy group; a 2,4,6-trimethylphenoxy group; a p-tert-butylphenoxy group; a 3-biphenyloxy group; a 4-biphenyloxy group; a 1-naphthyloxy group; a 2-naphthyloxy group; a 4-methyl-1-naphthyloxy group; a 5-methyl-2-naphthyloxy group; a 1-anthryloxy group; a 2-anthryloxy group; a 9-anthryloxy group; a 1-phenanthryloxy group; a 3-phenanthryloxy group; a 9-phenanthryloxy group and the like, and specific examples of the arylthioxy group may include a phenylthioxy group; a 2-methylphenylthioxy group; a 4-tert-butylphenylthioxy group and the like, and specific examples of the arylsulfoxy group may include a benzenesulfoxy group; a p-toluenesulfoxy group and the like, however, the aryloxy group, the arylthioxy group and the arylsulfonyl group are not limited thereto.

In the present specification, examples of the arylamine group include a substituted or unsubstituted monoarylamine group, a substituted or unsubstituted diarylamine group, or a substituted or unsubstituted triarylamine group. The aryl group in the arylamine group may be a monocyclic aryl group or a multicyclic aryl group. The arylamine group including two or more aryl groups may include monocyclic aryl groups, multicyclic aryl groups, or both monocyclic aryl groups and multicyclic aryl groups. For example, the aryl group in the arylamine group may be selected from among the examples of the aryl group described above.

In the present specification, the heteroaryl group is a group including one or more atoms that are not carbon, that is, heteroatoms, and specifically, the heteroatom may include one or more atoms selected from the group consisting of O, N, Se, S and the like. The number of carbon atoms is not particularly limited, but is preferably from 2 to 30 and more preferably from 2 to 20, and the heteroaryl group may be monocyclic or multicyclic. Examples of the heteroaryl group may include a thiophene group; a furanyl group; a pyrrole group; an imidazolyl group; a thiazolyl group; an oxazolyl group; an oxadiazolyl group; a pyridyl group; a bipyridyl group; a pyrimidyl group; a triazinyl group; a triazolyl group; an acridinyl group; a pyridazinyl group; a pyrazinyl group; a qinolinyl group; a quinazolinyl group; a quinoxalinyl group; a phthalazinyl group; a pyridopyrimidinyl group; a pyridopyrazinyl group; a pyrazinopyrazinyl group; an isoquinolinyl group; an indolyl group; a carbazolyl group; a benzoxazolyl group; a benzimidazolyl group; a benzothiazolyl group; a benzocarbazolyl group; a benzothiophenyl group; a dibenzothiophenyl group; a benzofuranyl group; a phenanthrolinyl group; an isoxazolyl group; a thiadiazolyl group; a phenothiazinyl group; a dibenzofuranyl group and the like, but are not limited thereto.

In the present specification, examples of the heteroarylamine group include a substituted or unsubstituted monoheteroarylamine group, a substituted or unsubstituted diheteroarylamine group, or a substituted or unsubstituted triheteroarylamine group. The heteroarylamine group including two or more heteroaryl groups may include monocyclic heteroaryl groups, multicyclic heteroaryl groups, or both monocyclic heteroaryl groups and multicyclic heteroaryl groups. For example, the heteroaryl group in the heteroarylamine group may be selected from among the examples of the heteroaryl group described above.

In the present specification, examples of the heteroaryl group in the N-arylheteroarylamine group and the N-alkylheteroarylamine group are the same as the examples of the heteroaryl group described above.

In the present specification, the arylene group means an aryl group having two bonding sites, that is, a divalent group. Descriptions on the aryl group provided above may be applied thereto except for each being a divalent group.

In the present specification, the heteroarylene group means a heteroaryl group having two bonding sites, that is, a divalent group. Descriptions on the heteroaryl group provided above may be applied thereto except for each being a divalent group.

According to one embodiment of the present specification, in Chemical Formula 1, L is a direct bond; or a substituted or unsubstituted arylene group.

According to one embodiment of the present specification, in Chemical Formula 1, L is a direct bond; a substituted or unsubstituted phenylene group; a substituted or unsubstituted biphenylene group; a substituted or unsubstituted naphthalene group; a substituted or unsubstituted terphenylene group; a substituted or unsubstituted quaterphenylene group; a substituted or unsubstituted anthracenylene group; a substituted or unsubstituted phenanthrenylene group; a substituted or unsubstituted triphenylenylene group; a substituted or unsubstituted pyrenylene group; a substituted or unsubstituted fluorenylene group; or a substituted or unsubstituted spiro cyclopentane fluorenylene group.

According to one embodiment of the present specification, in Chemical Formula 1, L is a direct bond; a phenylene group; a biphenylene group unsubstituted or substituted with a nitrile group; a naphthalene group; a terphenylene group; a quaterphenylene group; an anthracenylene group; a phenanthrenylene group; a triphenylenylene group; a pyrenylene group; a fluorenylene group unsubstituted or substituted with an alkyl group or an aryl group; or a spirocyclopentane fluorenylene group.

According to one embodiment of the present specification, in Chemical Formula 1, L is represented by a direct bond; or any one of the following structural formulae.

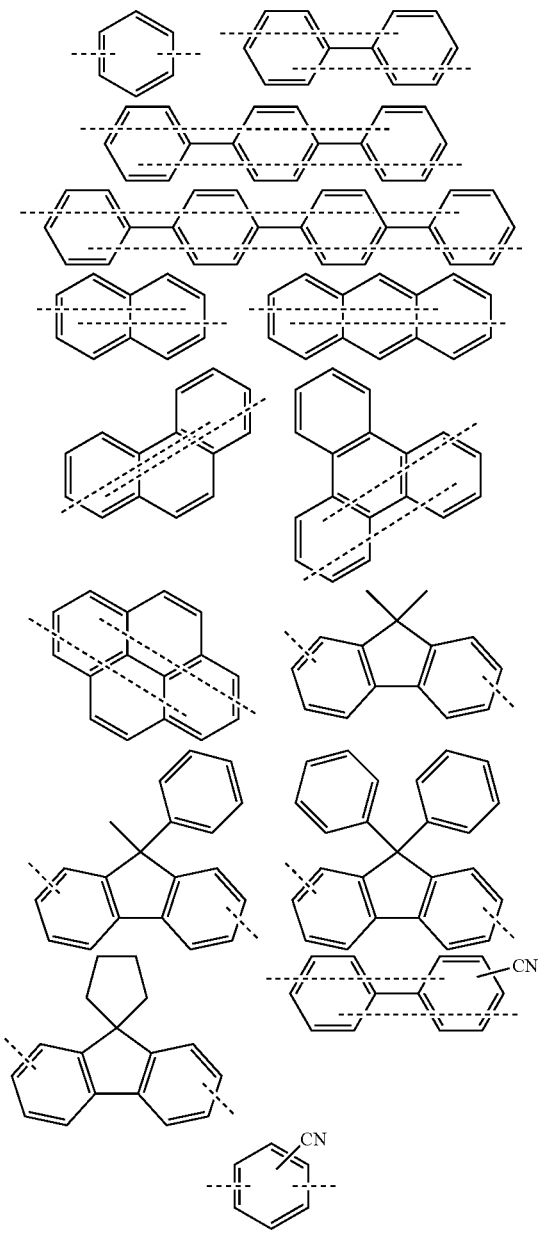

In the structures, ----- is a site bonding to the main chain.

According to one embodiment of the present specification, Ar1 is a substituted or unsubstituted heteroring comprising two or more Ns.

According to one embodiment of the present specification, Ar1 is a substituted or unsubstituted heteroring having 2 to 24 carbon atoms comprising two or more Ns.

According to one embodiment of the present specification, Ar1 is a substituted or unsubstituted heteroring having 2 to 20 carbon atoms comprising two or more Ns.

According to one embodiment of the present specification, Ar1 is a heteroring comprising two or more Ns unsubstituted or substituted with an aryl group unsubstituted or substituted with a nitrile group.

According to one embodiment of the present specification, Ar1 is any one of the following Chemical Formulae 2-A to 2-E.

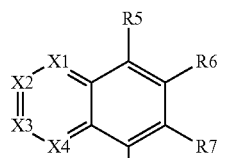

[Chemical Formula 2-A]

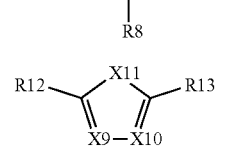

[Chemical Formula 2-B]

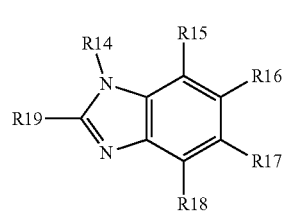

[Chemical Formula 2-C]

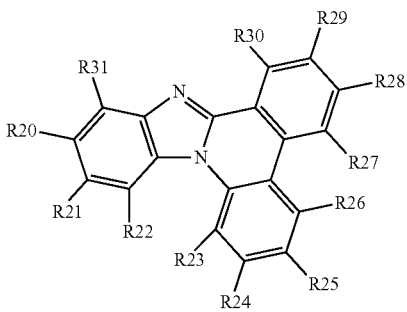

[Chemical Formula 2-D]

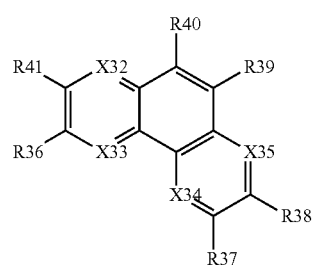

[Chemical Formula 2-E]

In Chemical Formula 2-A to Chemical Formula 2-E,

X1 is N or CR1, X2 is N or CR2, X3 is N or CR3, X4 is N or CR4, and at least two of X1 to X4 are N, X9 is N or CR9, X10 is N or CR10, and X11 is O; S; or NR11, X11 is NR11 and at least one of X9 and X10 is N, or X11 is O or S and X9 and X10 are each N, X32 is N or CR32, X33 is N or CR33, X34 is N or CR34, X35 is N or CR35, and at least two of X32 to X35 are N, any one of R1 to R8, any one of R9 to R13, any one of R14 to R19, any one of R20 to R31 or any one of R32 to R41 is a site bonding to L of Chemical Formula 1, and the rest of R1 to R41 other than the site bonding to L of Chemical Formula 1 are the same as or different from each other, and each independently hydrogen; deuterium; a nitrile group; a nitro group; a hydroxyl group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group.

According to one embodiment of the present specification, the rest of R1 to R41 other than the site bonding to L of Chemical Formula 1 are the same as or different from each other, and each independently hydrogen; a substituted or unsubstituted phenyl group; a substituted or unsubstituted naphthyl group; or a substituted or unsubstituted biphenyl group.

According to one embodiment of the present specification, the rest of R1 to R41 other than the site bonding to L of Chemical Formula 1 are the same as or different from each other, and each independently hydrogen; a phenyl group unsubstituted or substituted with a nitrile group; a naphthyl group unsubstituted or substituted with a nitrile group; or a biphenyl group unsubstituted or substituted with a nitrile group.

According to one embodiment of the present specification, the rest of R1 to R8 other than the site bonding to L of Chemical Formula 1 are the same as or different from each other, and each independently hydrogen; a phenyl group unsubstituted or substituted with a nitrile group; a naphthyl group; or a biphenyl group unsubstituted or substituted with a nitrile group.

According to one embodiment of the present specification, the rest of R9 to R13 other than the site bonding to L of Chemical Formula 1 are the same as or different from each other, and each independently hydrogen; or a phenyl group unsubstituted or substituted with a nitrile group.

According to one embodiment of the present specification, the rest of R14 to R19 other than the site bonding to L of Chemical Formula 1 are the same as or different from each other, and each independently hydrogen; or a phenyl group unsubstituted or substituted with a nitrile group.

According to one embodiment of the present specification, the rest of R20 to R31 other than the site bonding to L of Chemical Formula 1 are each hydrogen.

According to one embodiment of the present specification, the rest of R32 to R41 other than the site bonding to L of Chemical Formula 1 are the same as or different from each other, and each independently hydrogen; or a phenyl group unsubstituted or substituted with a nitrile group.

According to one embodiment of the present specification, Chemical Formula 2-A is represented by any one selected from among the following Chemical Formulae 3-A to 3-D.

[Chemical Formula 3-A]

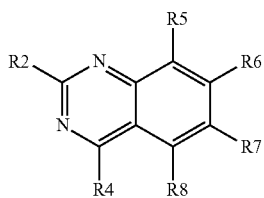

[Chemical Formula 3-B]

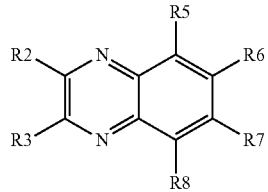

[Chemical Formula 3-C]

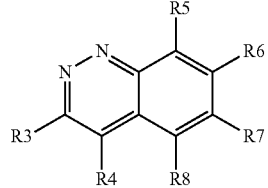

[Chemical Formula 3-D]

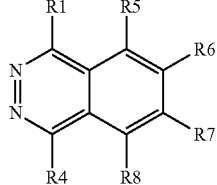

In Chemical Formula 3-A, any one of R2 and R4 to R8 is a site bonding to L of Chemical Formula 1, in Chemical Formula 3-B, any one of R2, R3 and R5 to R8 is a site bonding to L of Chemical Formula 1, in Chemical Formula 3-C, any one of R3 to R8 is a site bonding to L of Chemical Formula 1, in Chemical Formula 3-D, any one of R1 and R4 to R8 is a site bonding to L of Chemical Formula 1, and the rest of R1 to R8 other than the site bonding to L of Chemical Formula 1 are the same as or different from each other, and each independently hydrogen; deuterium; a nitrile group; a nitro group; a hydroxyl group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group.

According to one embodiment of the present specification, in Chemical Formulae 3-A to 3-D, the rest of R1 to R8 other than the site bonding to L of Chemical Formula 1 are the same as or different from each other, and each independently hydrogen; a substituted or unsubstituted phenyl group; a substituted or unsubstituted naphthyl group; or a substituted or unsubstituted biphenyl group.

According to one embodiment of the present specification, in Chemical Formulae 3-A to 3-D, the rest of R1 to R8 other than the site bonding to L of Chemical Formula 1 are the same as or different from each other, and each independently hydrogen; a phenyl group unsubstituted or substituted with a nitrile group; a naphthyl group unsubstituted or substituted with a nitrile group; or a biphenyl group unsubstituted or substituted with a nitrile group.

According to one embodiment of the present specification, Chemical Formula 2-B is represented by any one selected from among the following Chemical Formulae 4-A to 4-D.

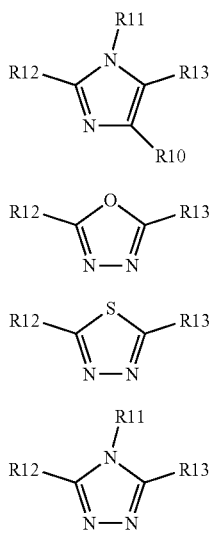

[Chemical Formula 4-A]

[Chemical Formula 4-B]

[Chemical Formula 4-C]

[Chemical Formula 4-D]

In Chemical Formula 4-A, any one of R10 to R13 is a site bonding to L of Chemical Formula 1, in Chemical Formulae 4-B and 4-C, R12 or R13 is a site bonding to L of Chemical Formula 1, in Chemical Formula 4-D, any one of R11 to R13 is a site bonding to L of Chemical Formula 1, and the rest of R10 to R13 other than the site bonding to L of Chemical Formula 1 are the same as or different from each other, and each independently hydrogen; deuterium; a nitrile group; a nitro group; a hydroxyl group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group.

According to one embodiment of the present specification, in Chemical Formulae 4-A to 4-D, the rest of R10 to R13 other than the site bonding to L of Chemical Formula 1 are the same as or different from each other, and each independently hydrogen; a substituted or unsubstituted phenyl group; a substituted or unsubstituted naphthyl group; or a substituted or unsubstituted biphenyl group.

According to one embodiment of the present specification, in Chemical Formulae 4-A to 4-D, the rest of R10 to R13 other than the site bonding to L of Chemical Formula 1 are the same as or different from each other, and each independently hydrogen; or a phenyl group unsubstituted or substituted with a nitrile group.

According to one embodiment of the present specification, Chemical Formula 2-E is represented by any one selected from among the following Chemical Formula 5-A to Chemical Formula 5-G.

[Chemical Formula 5-A]

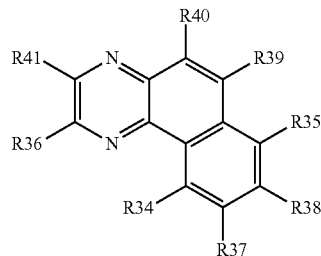

[Chemical Formula 5-B]

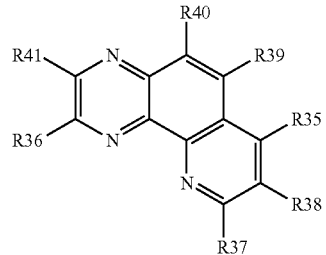

[Chemical Formula 5-C]

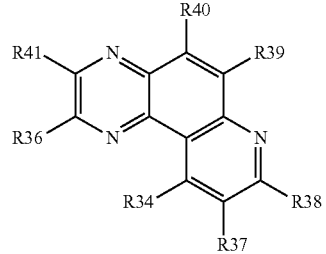

[Chemical Formula 5-D]

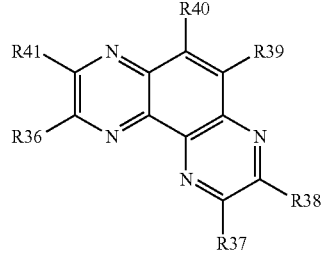

[Chemical Formula 5-E]

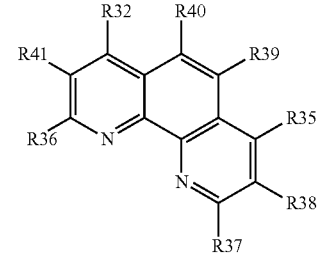

[Chemical Formula 5-F]

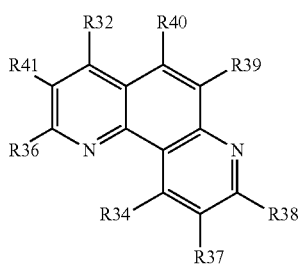

[Chemical Formula 5-G]

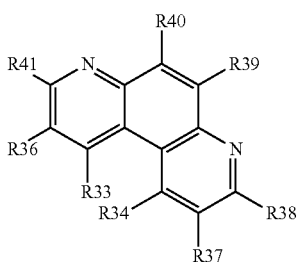

In Chemical Formula 5-A, any one of R34 to R41 is a site bonding to L of Chemical Formula 1, in Chemical Formula 5-B, any one of R35 to R41 is a site bonding to L of Chemical Formula 1, in Chemical Formula 5-C, any one of R34 and R36 to R41 is a site bonding to L of Chemical Formula 1, in Chemical Formula 5-D, any one of R36 to R41 is a site bonding to L of Chemical Formula 1, in Chemical Formula 5-E, any one of R32 and R35 to R41 is a site bonding to L of Chemical Formula 1, in Chemical Formula 5-F, any one of R32, R34 and R36 to R41 is a site bonding to L of Chemical Formula 1, in Chemical Formula 5-G, any one of R33, R34 and R36 to R41 is a site bonding to L of Chemical Formula 1, and the rest of R32 to R41 other than the site bonding to L of Chemical Formula 1 are the same as or different from each other, and each independently hydrogen; deuterium; a nitrile group; a nitro group; a hydroxyl group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group.

According to one embodiment of the present specification, in Chemical Formulae 5-A to 5-G, the rest of R32 to R41 other than the site bonding to L of Chemical Formula 1 are the same as or different from each other, and each independently hydrogen; a substituted or unsubstituted phenyl group; a substituted or unsubstituted naphthyl group; or a substituted or unsubstituted biphenyl group.

According to one embodiment of the present specification, in Chemical Formulae 5-A to 5-G, the rest of R32 to R41 other than the site bonding to L of Chemical Formula 1 are the same as or different from each other, and each independently hydrogen; or a phenyl group unsubstituted or substituted with a nitrile group.

According to one embodiment of the present specification, Chemical Formula 1 is represented by any one selected from among the following Chemical Formulae 1-1 to 1-3.

[Chemical Formula 1-1]

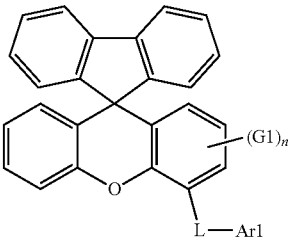

[Chemical Formula 1-2]

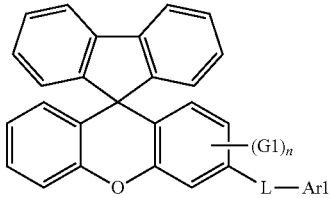

[Chemical Formula 1-3]

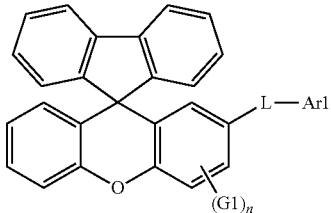

In Chemical Formulae 1-1 to 1-3,

L, Ar1, G1 and n have the same definitions as in Chemical Formula 1.

According to one embodiment of the present specification, G1 is hydrogen.

Electron mobility of a compound generally varies depending on orientation in a molecular 3D structure, and electron mobility is strengthened in a more horizontal structure. The heterocyclic compound represented by Chemical Formula 1 in which one -L-Ar1 is substituted according to one embodiment of the present specification has a strong tendency toward a horizontal structure of a molecule compared to compounds in which two or more -L-Arls are substituted, and has an advantage of enhancing electron mobility. Accordingly, when using the heterocyclic compound represented by Chemical Formula 1 in an organic light emitting device, effects of low driving voltage, high efficiency and long lifetime are obtained.

When referring to FIG. 3 and FIG. 4 illustrating 3D structures of Compounds E3 and E6 according to one embodiment of the present specification, the molecules of the compounds are identified to have a horizontal structure, and when referring to FIG. 5 and FIG. 6 illustrating 3D structures of Compounds ET-1-E and ET-1-I used as comparative example compounds of the present specification, the A axis and the B axis are almost perpendicular to each other in each compound identifying that the molecule is very out of a horizontal structure. As a result, Compounds E3 and E6 according to one embodiment of the present specification have a horizontal structure compared to Compounds ET-1-E and ET-1-I due to a difference in the orientation in the molecular 3D structure, and as a result, it is seen that excellent effects in terms of driving voltage, efficiency and lifetime are obtained when using the heterocyclic compound represented by Chemical Formula 1 in an organic light emitting device.

According to one embodiment of the present specification, the heterocyclic compound represented by Chemical Formula 1 is any one selected from among the following heterocyclic compounds.

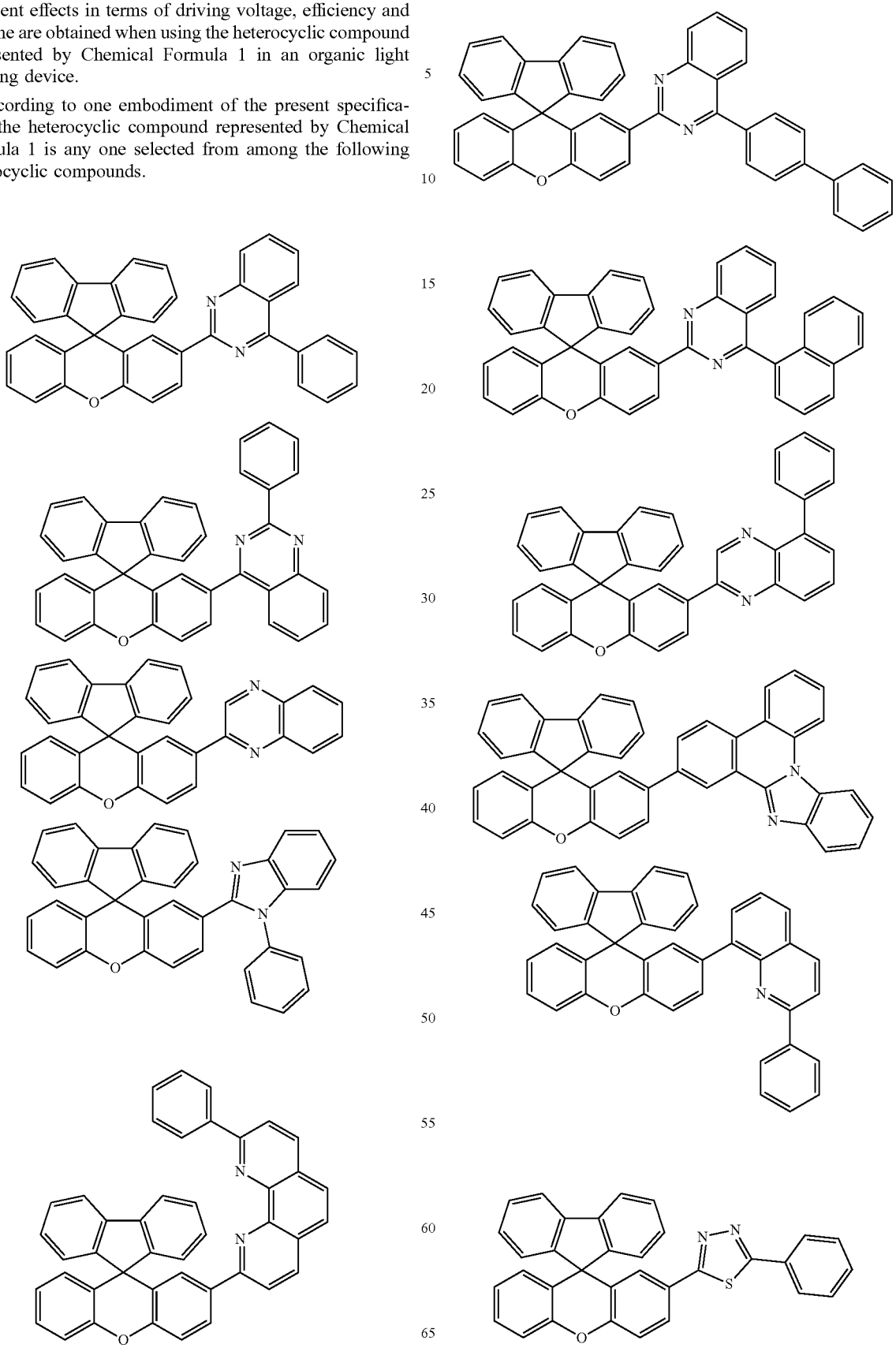

-continued
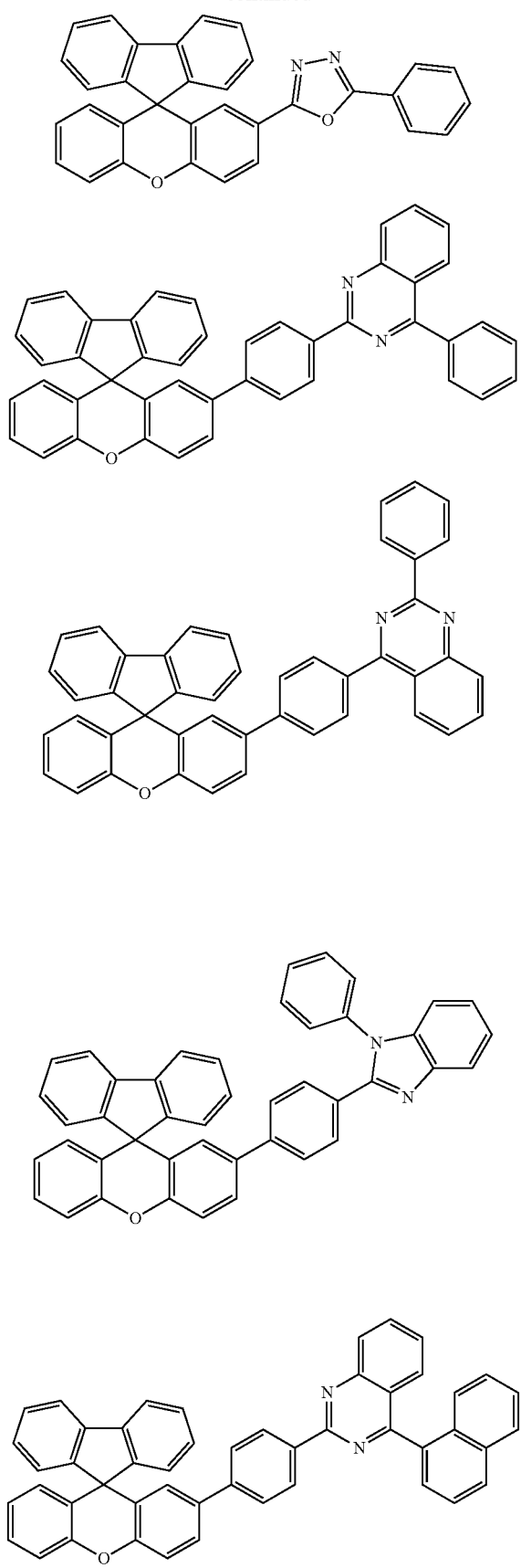
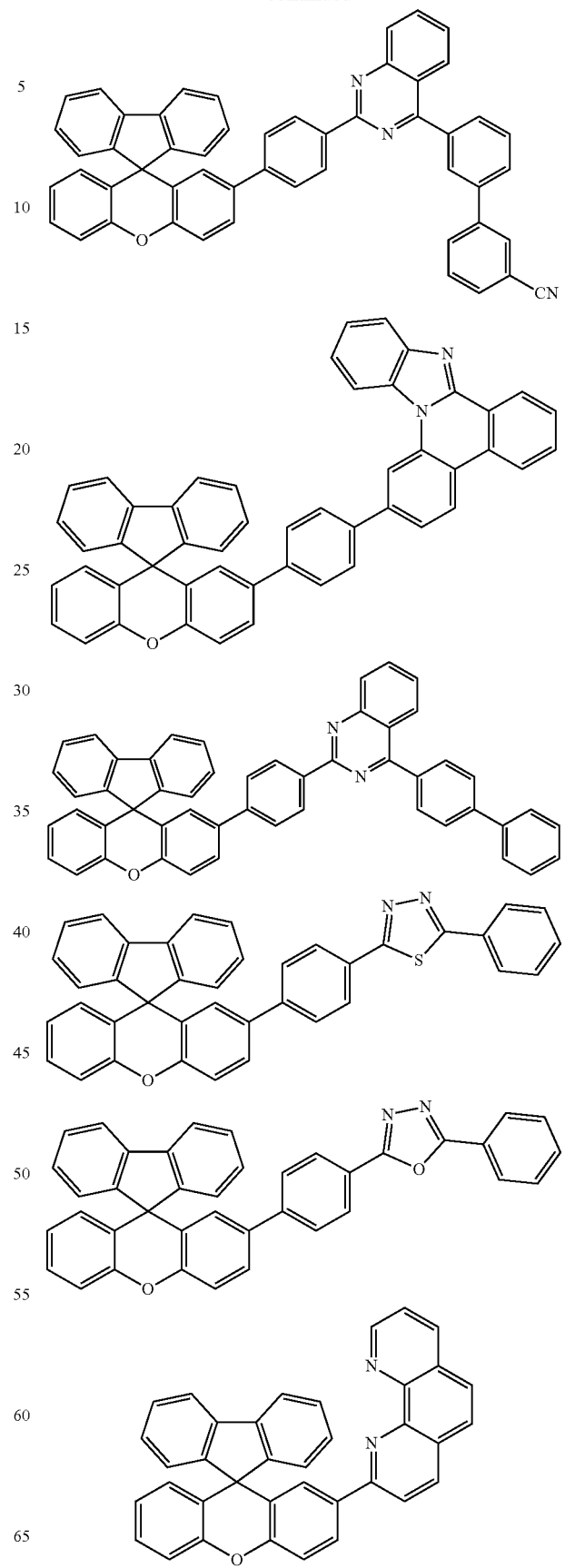

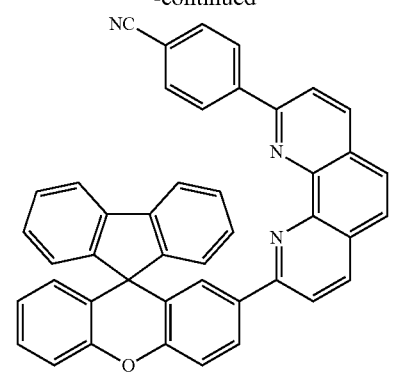
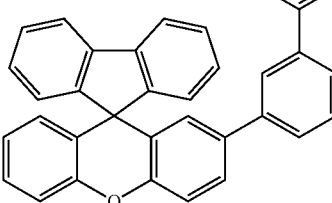
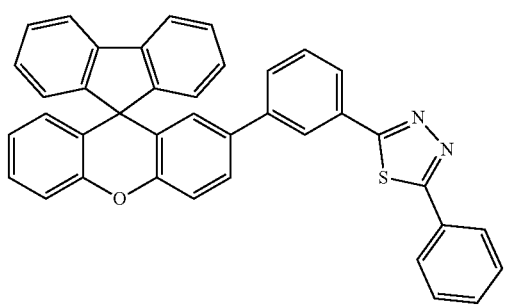
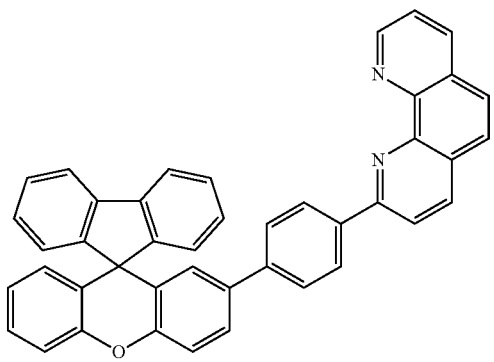
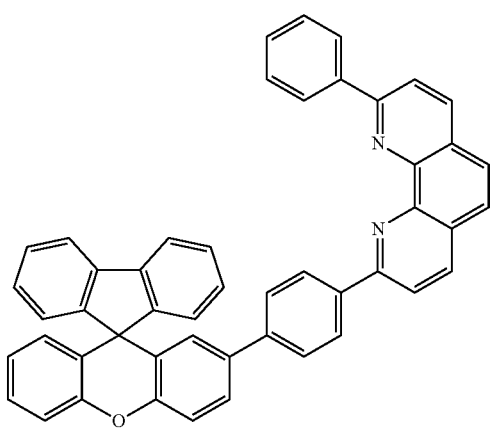
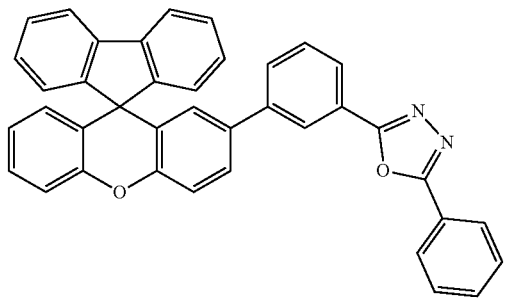
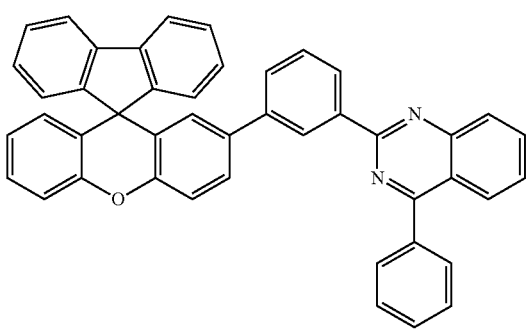
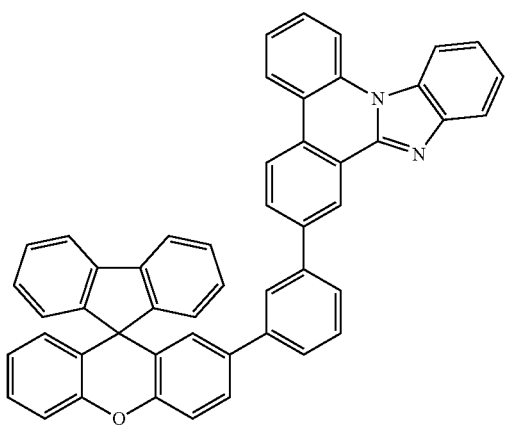

25
-continued
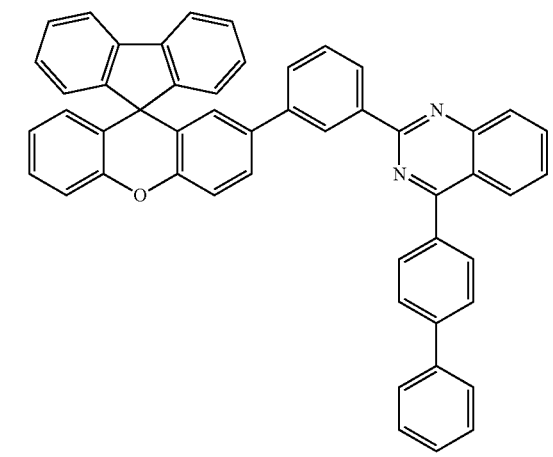
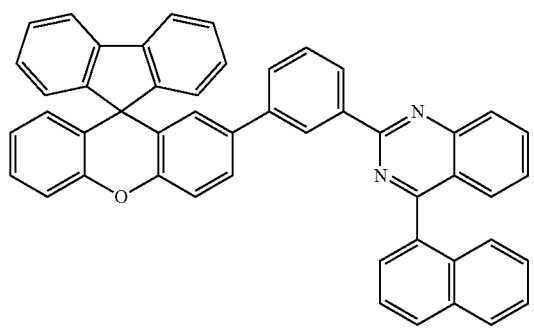
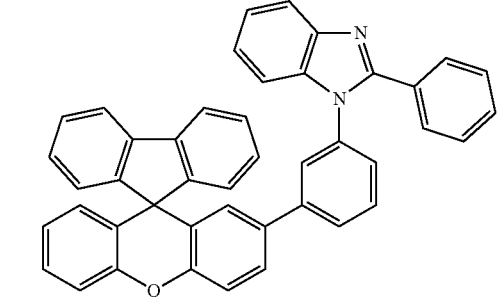
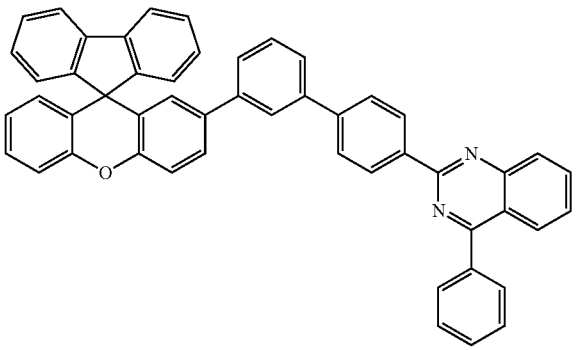
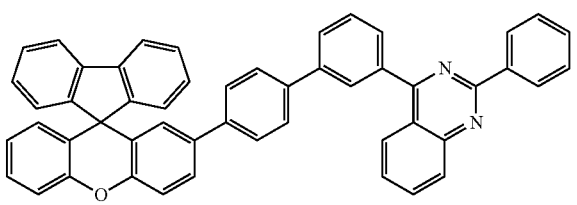
26
-continued
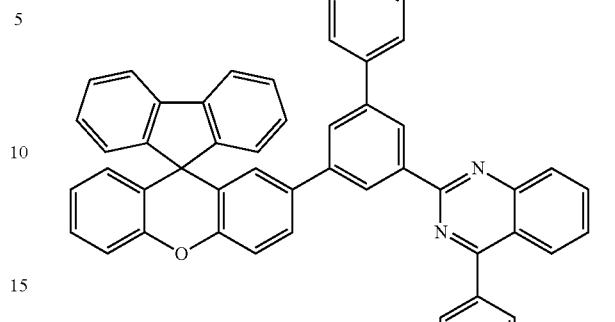
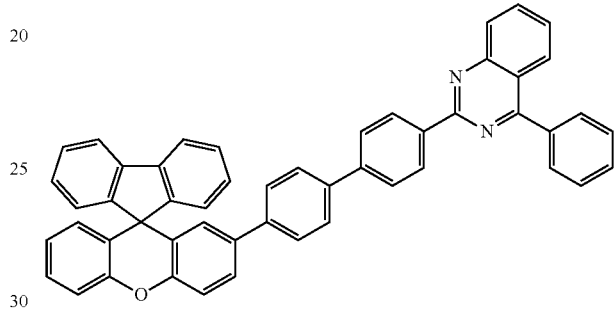
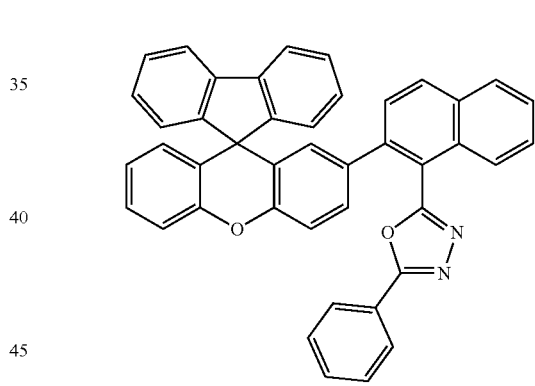
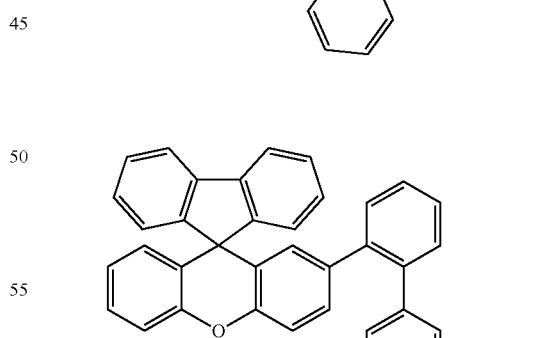
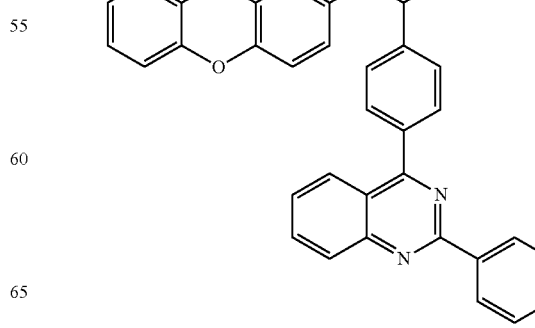

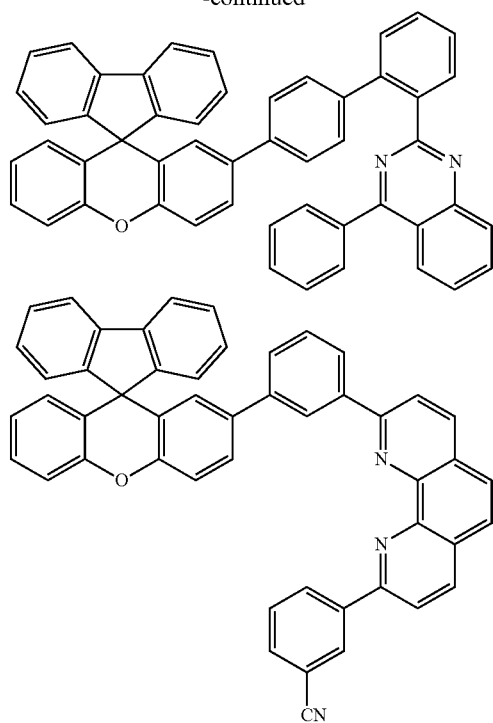
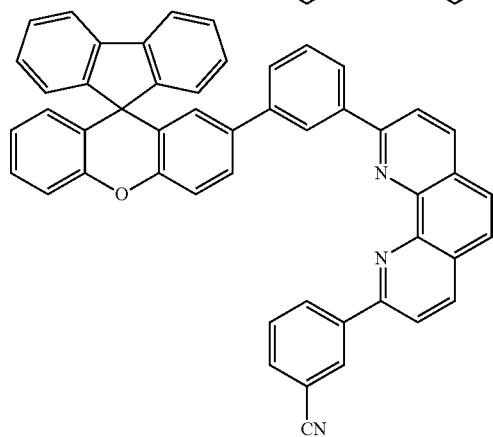
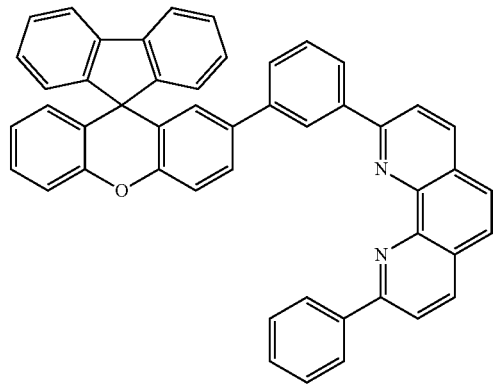
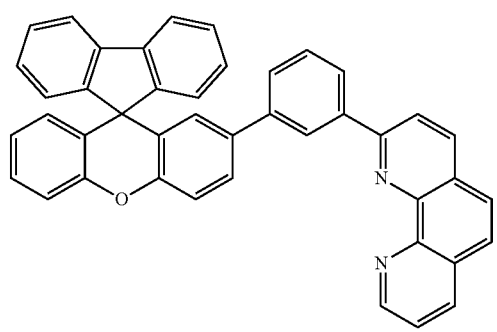
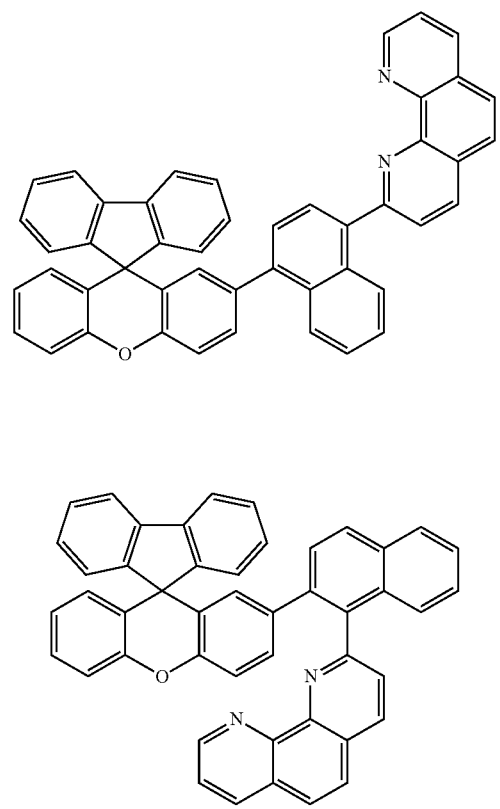
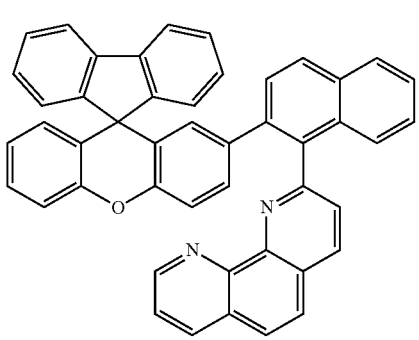
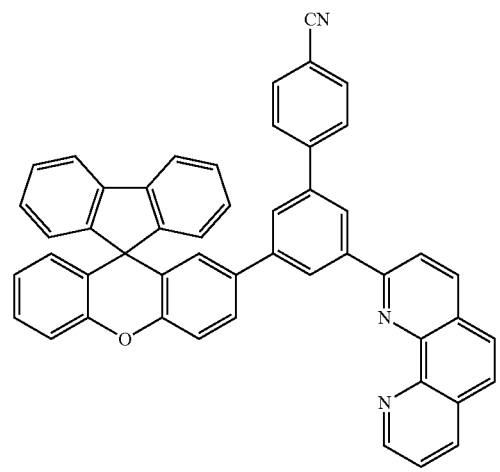
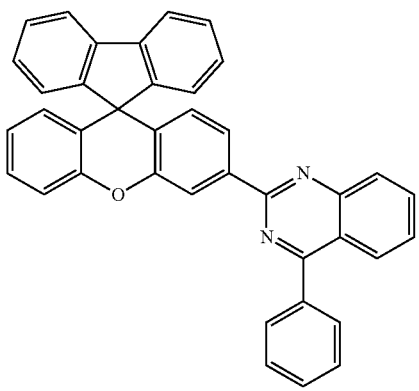

-continued
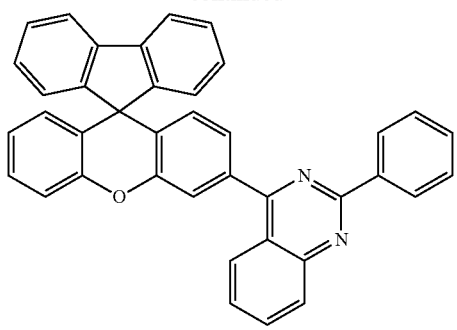
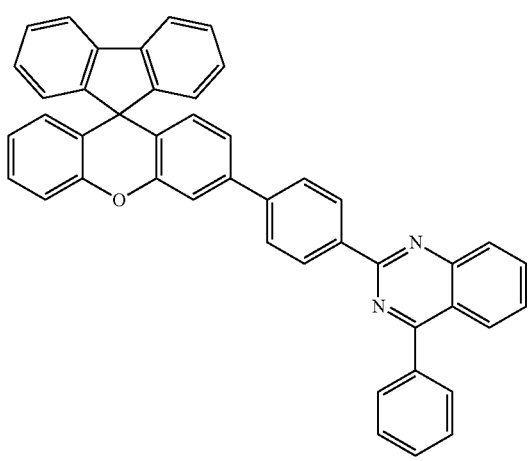
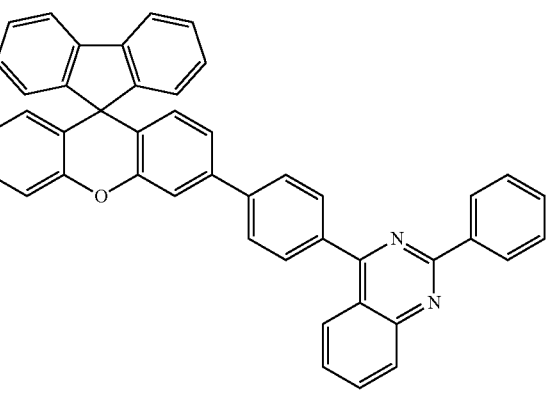
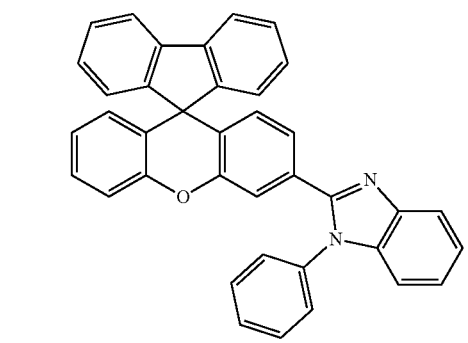
-continued
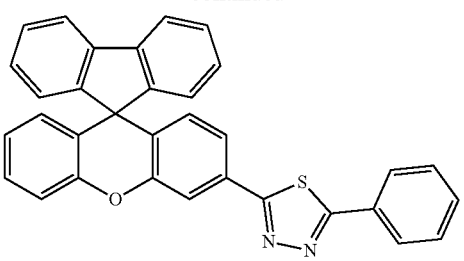
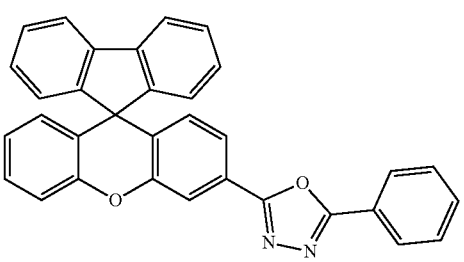
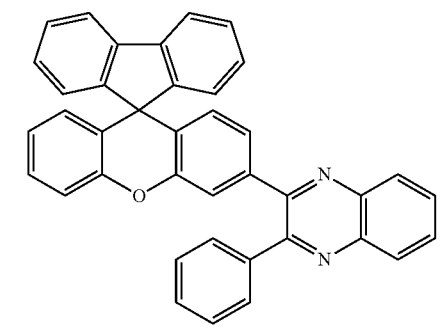
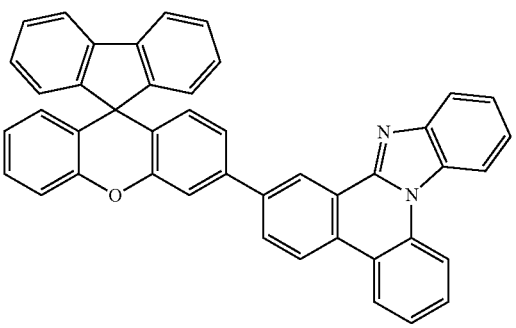
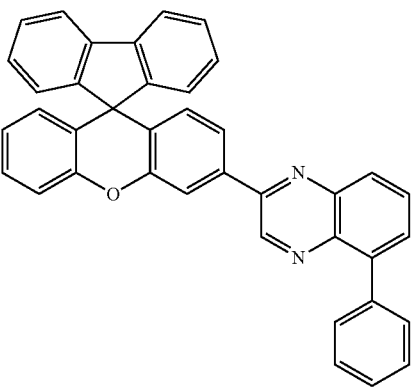

31
-continued
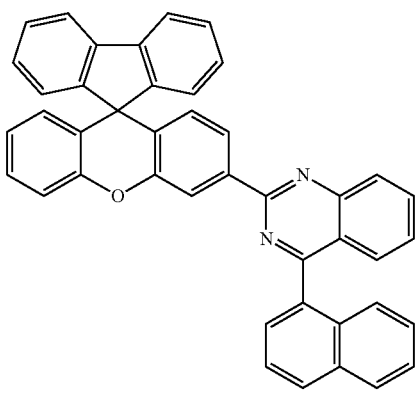
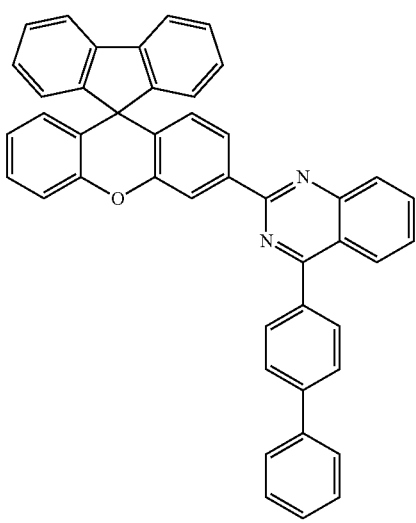
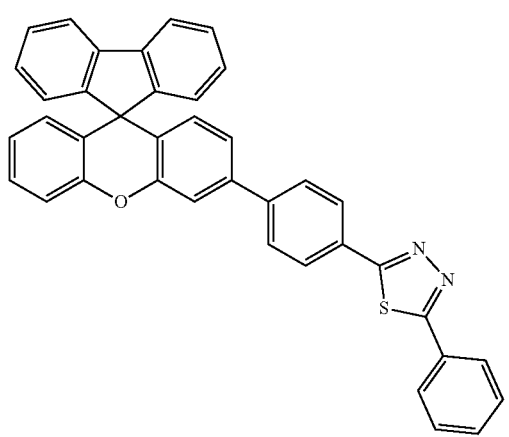
32
-continued
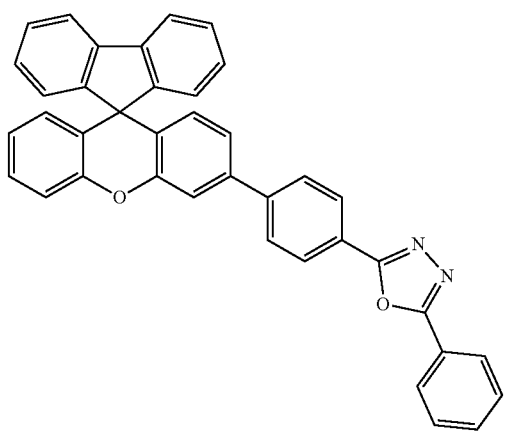
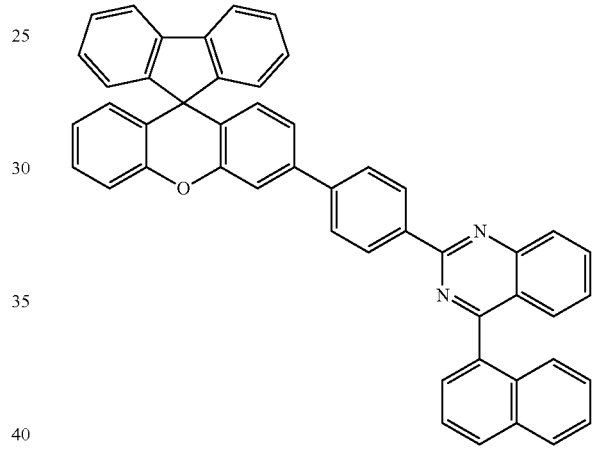
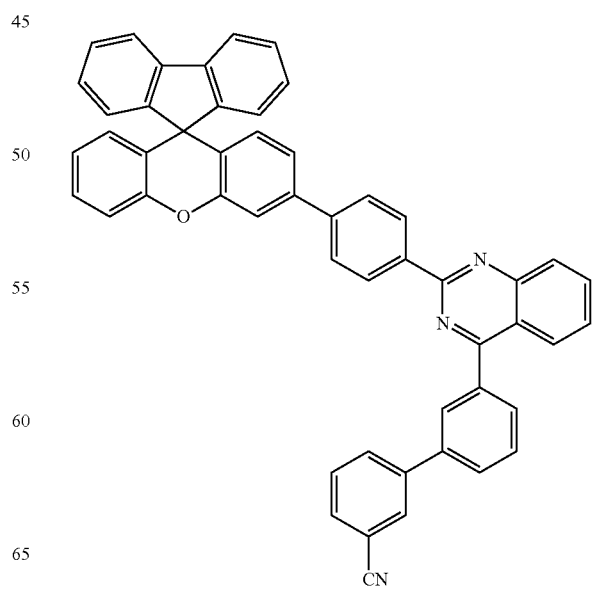

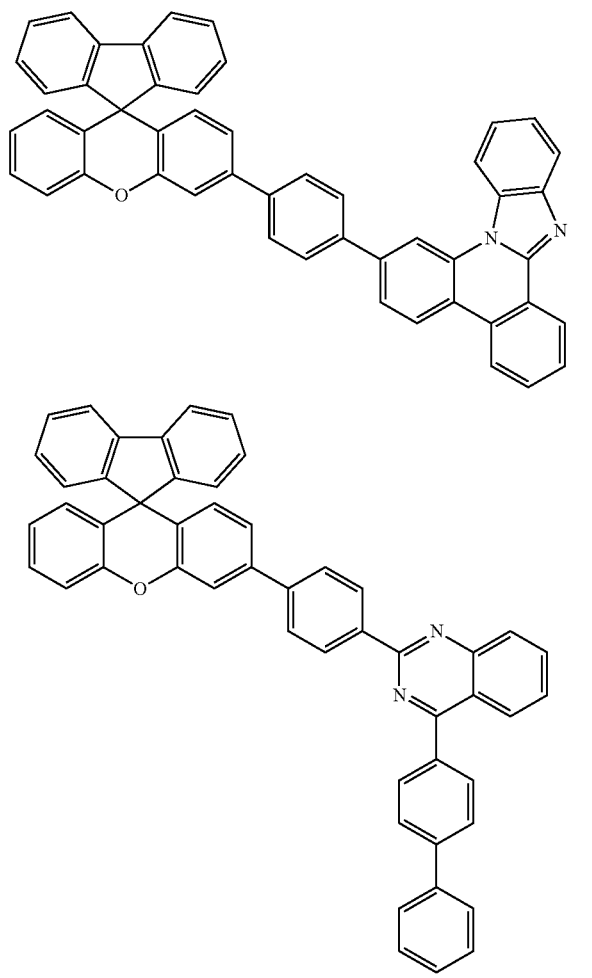
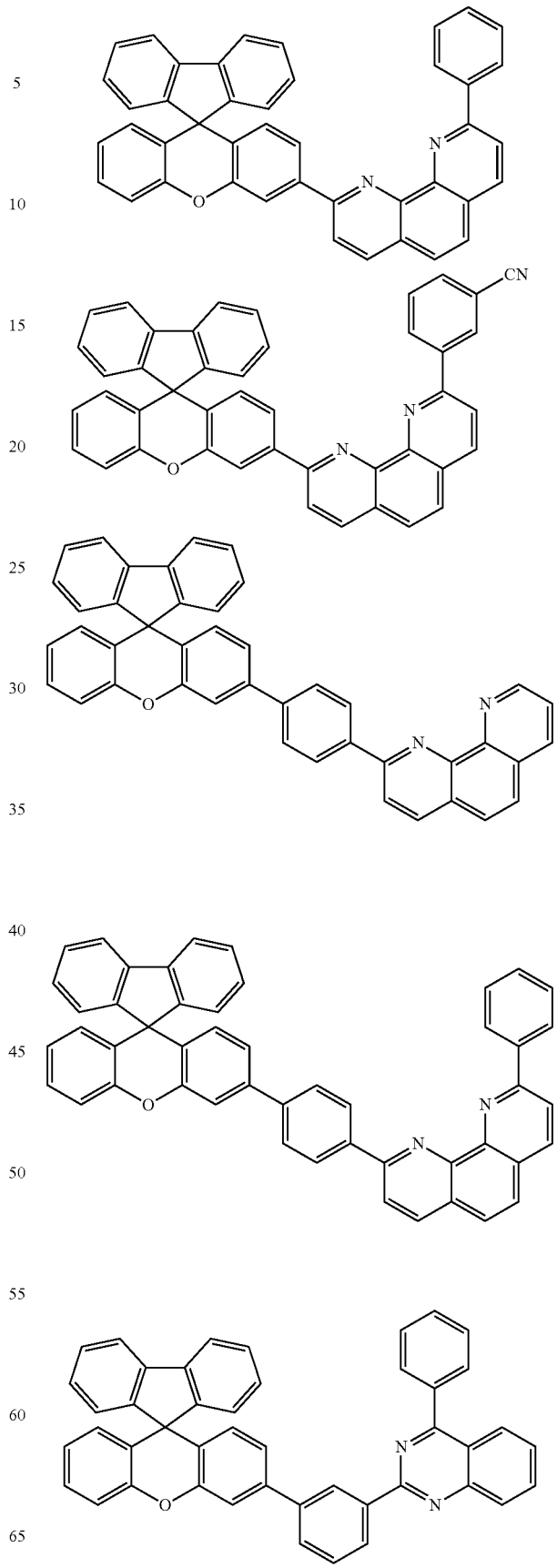

35
-continued
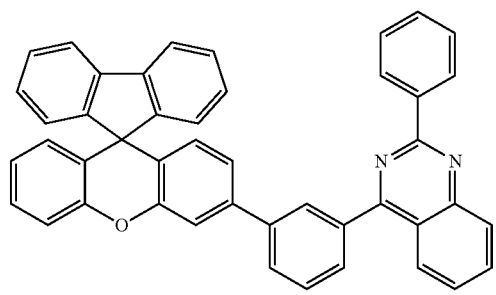
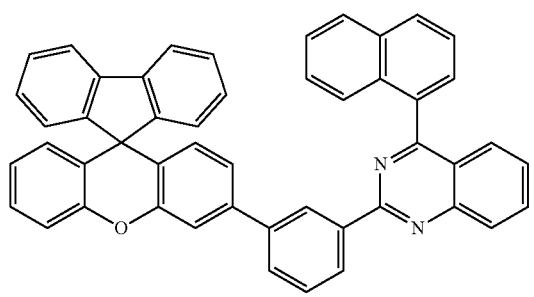
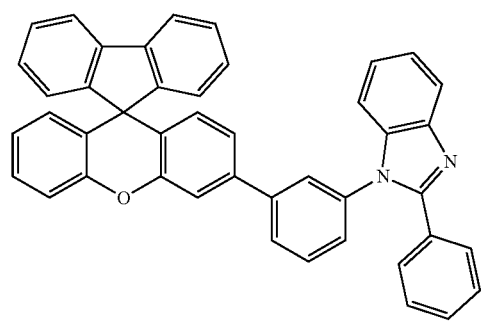
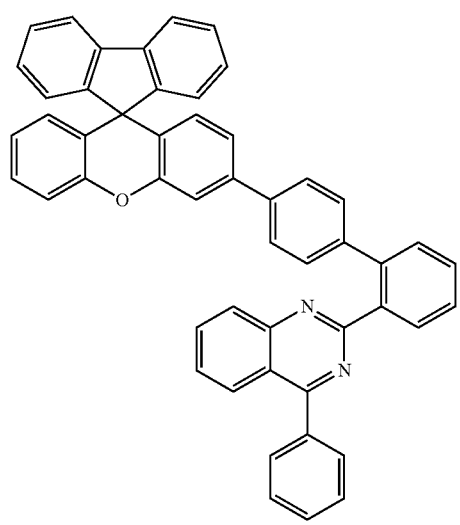
36
-continued
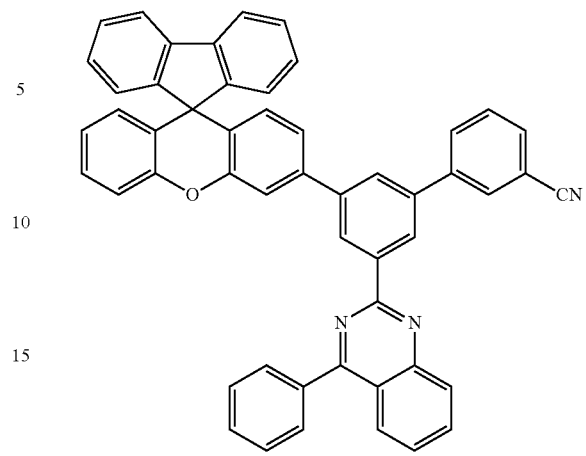
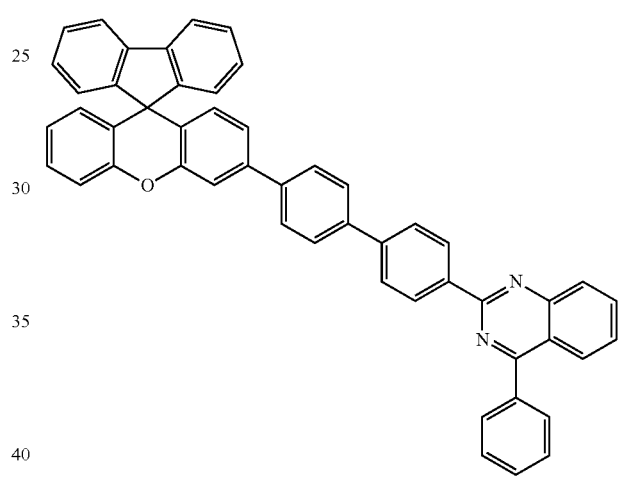
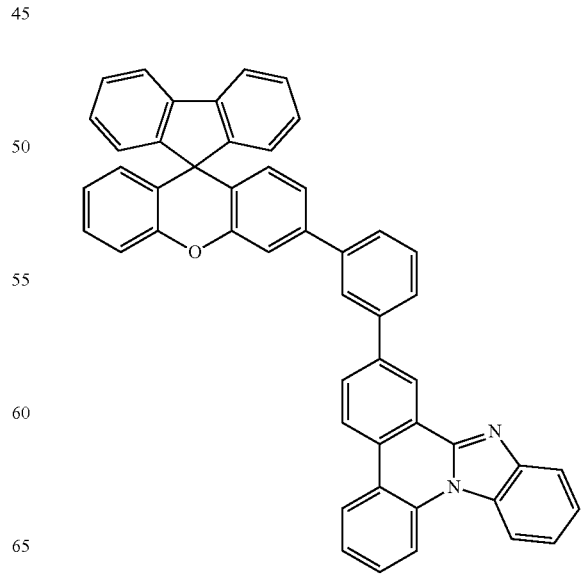

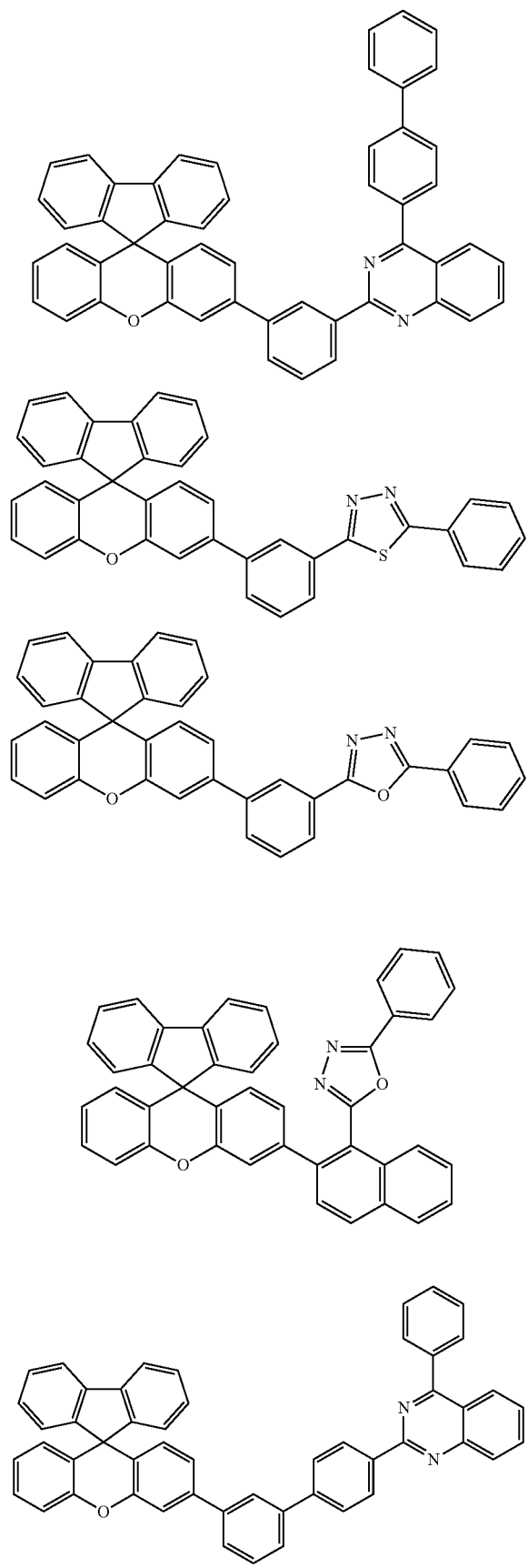
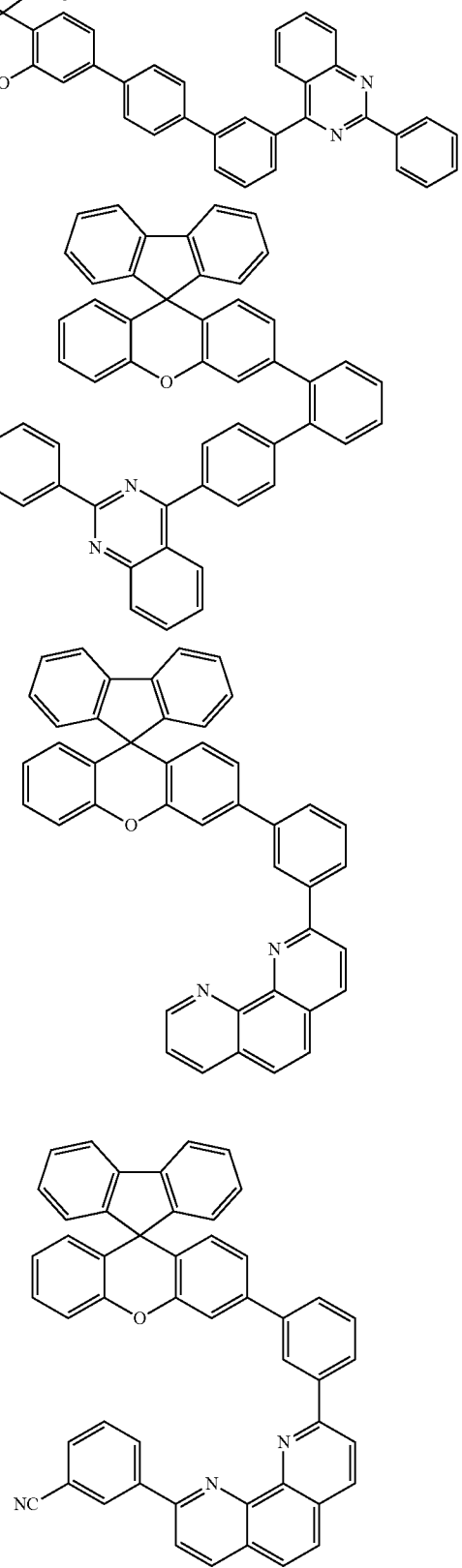

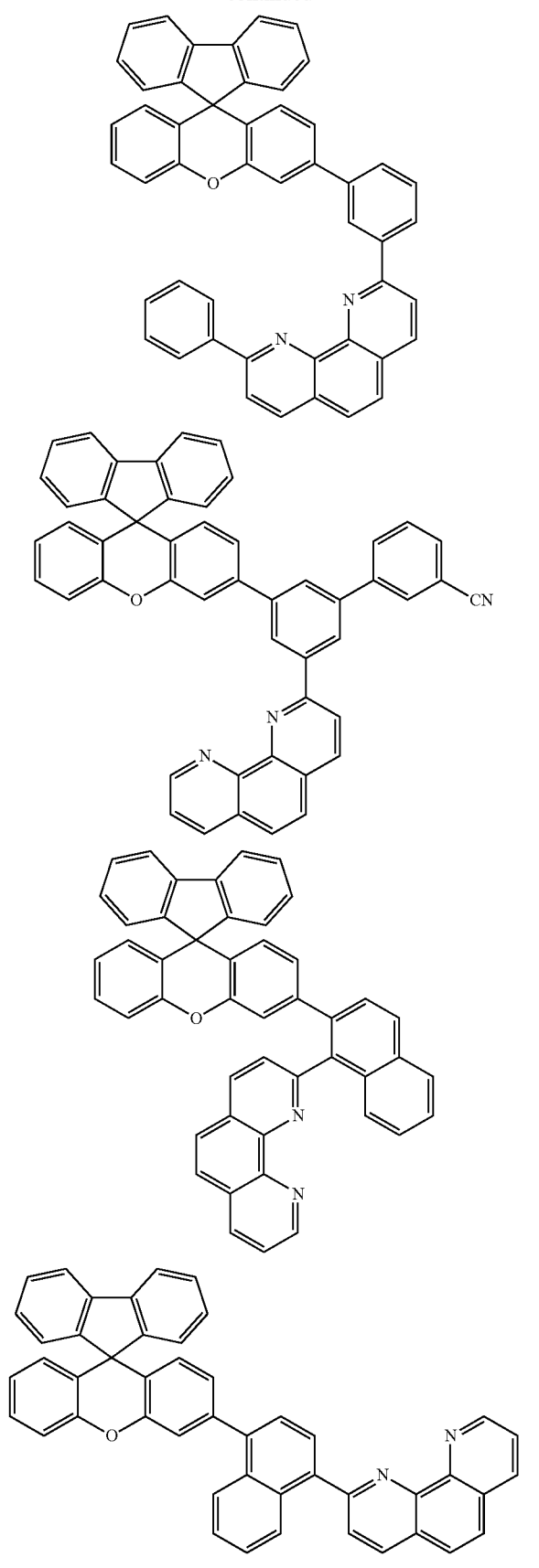

41
-continued
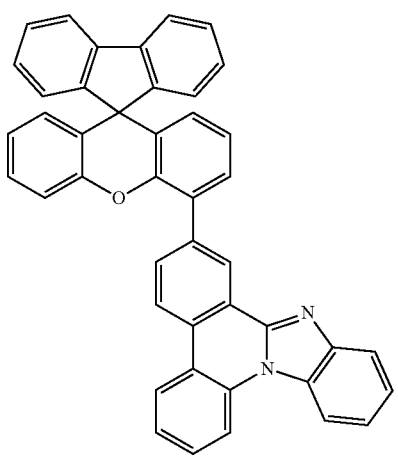
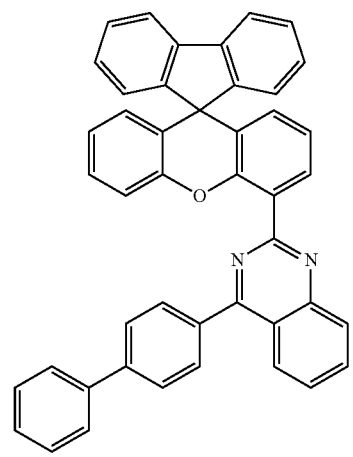
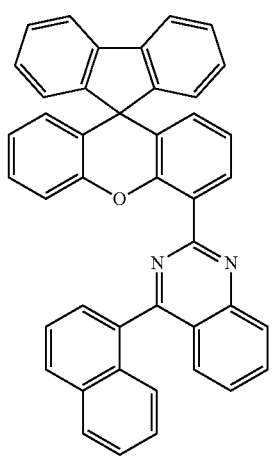
42
-continued
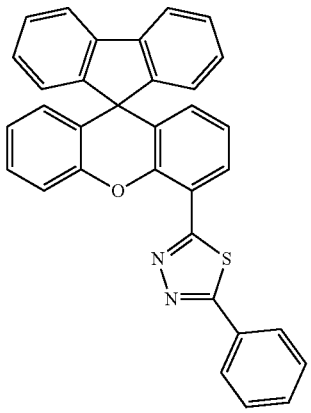
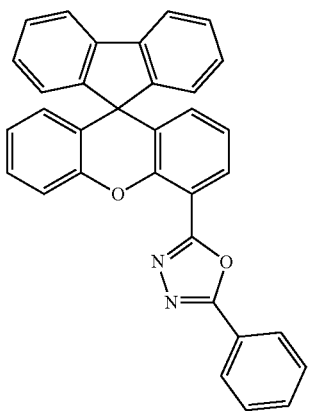
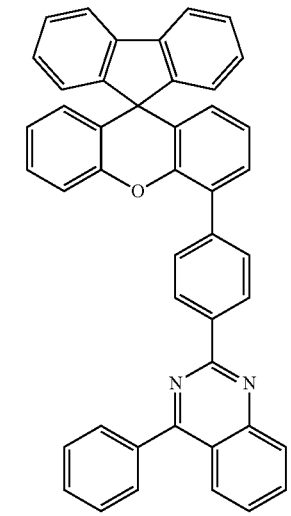

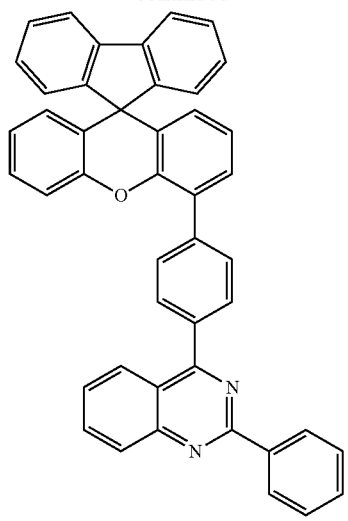
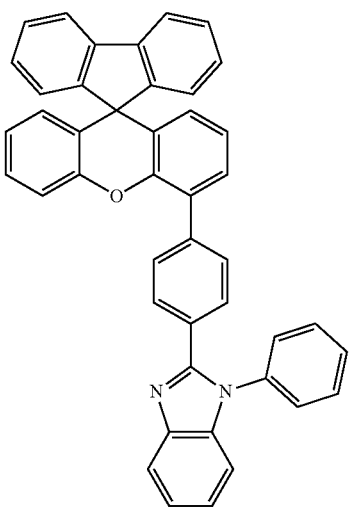
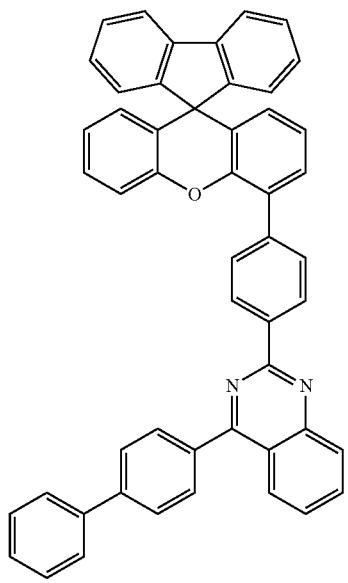
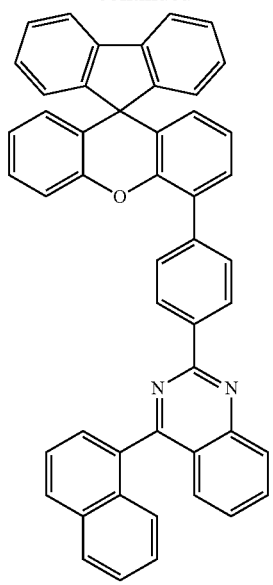
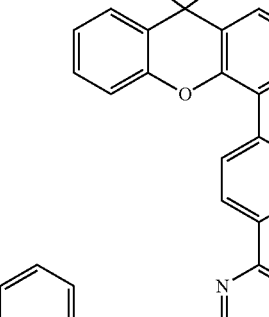
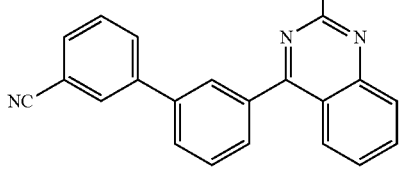
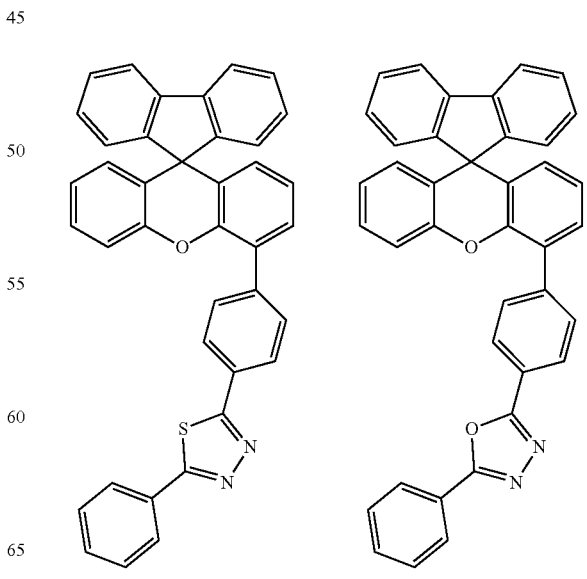

-continued
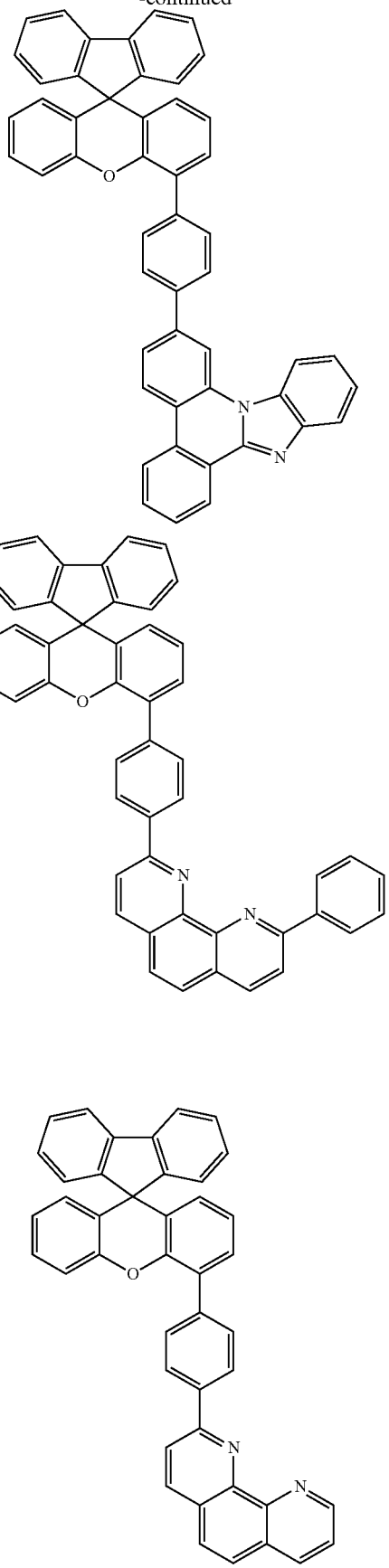
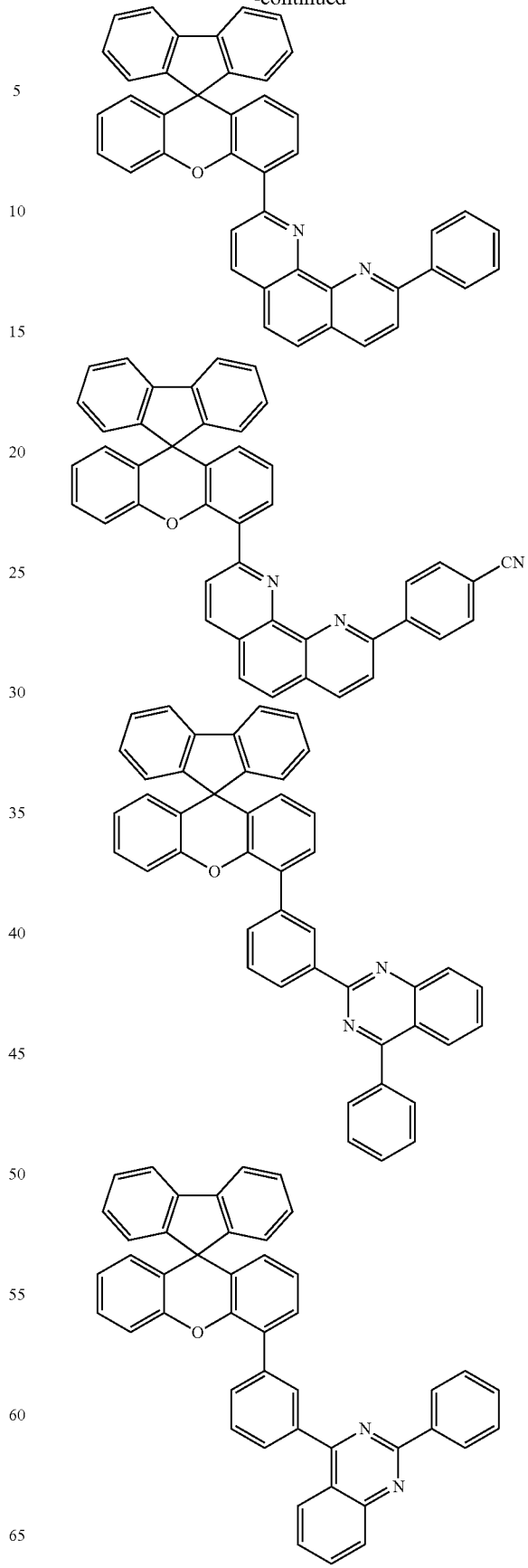

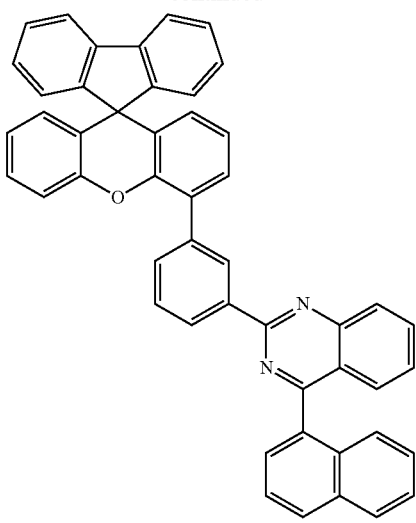
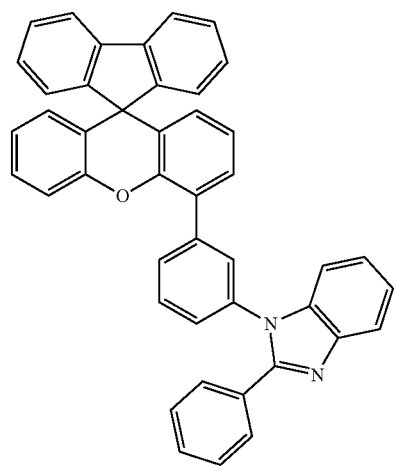
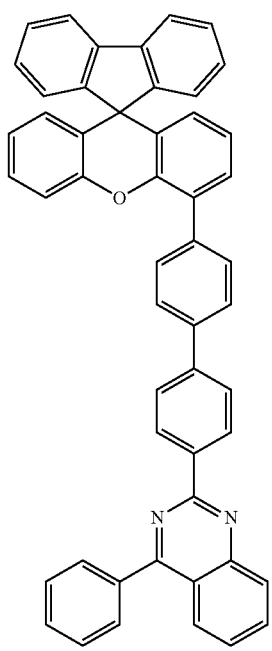
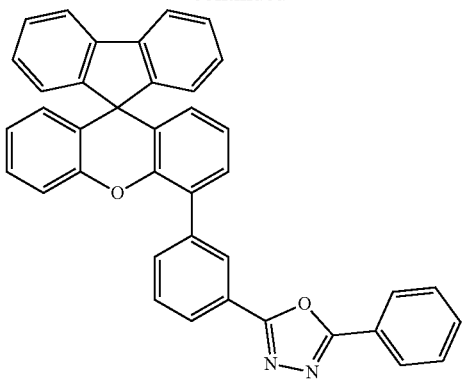
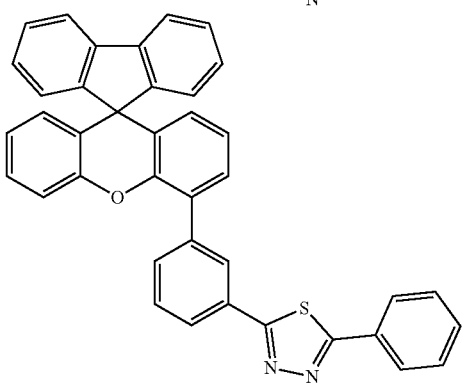
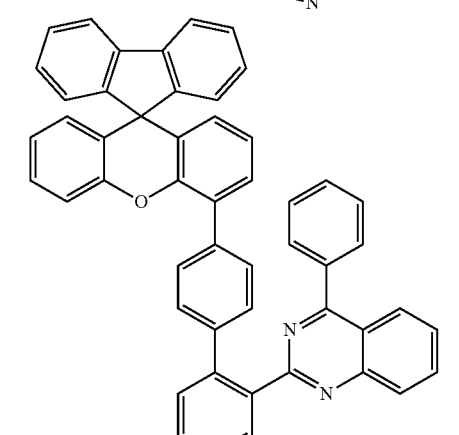
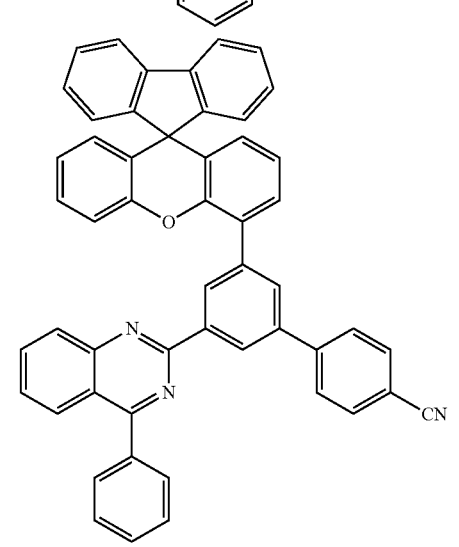

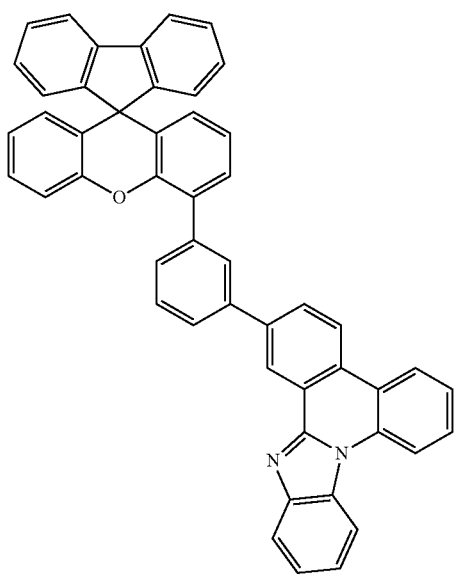
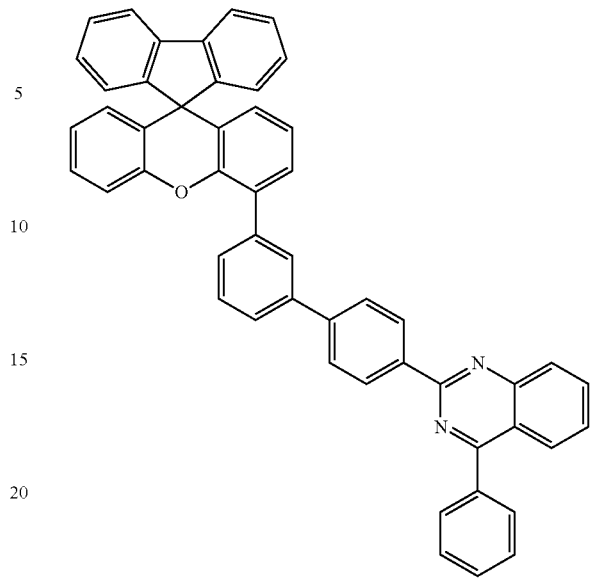
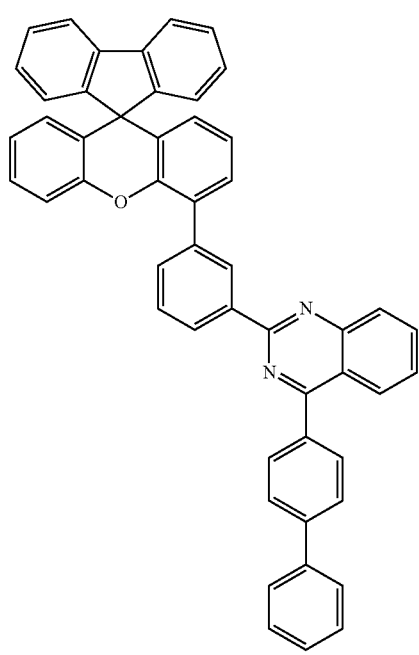
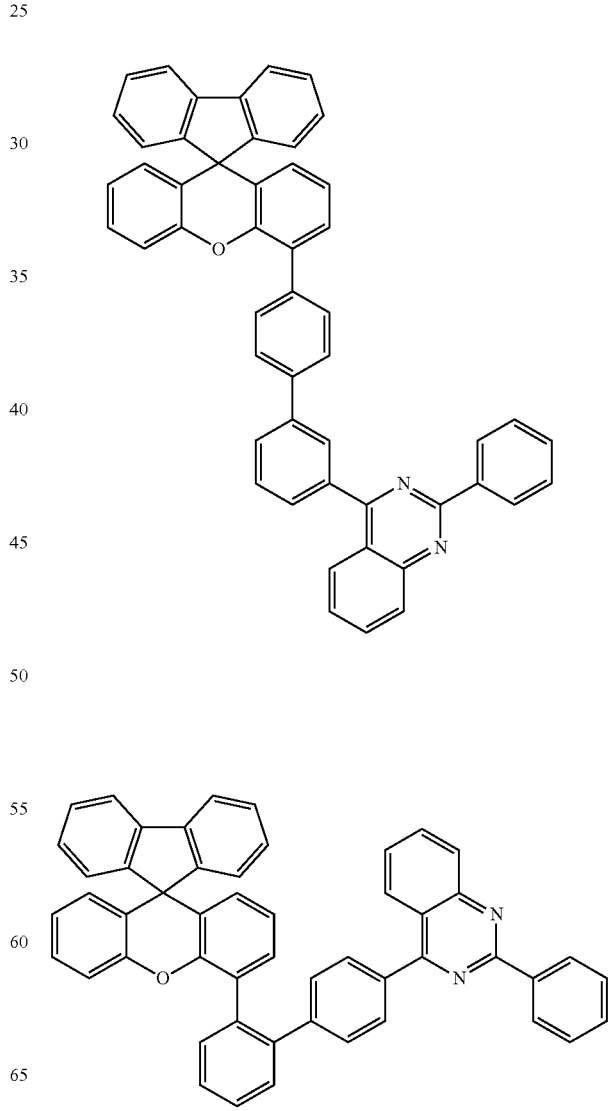

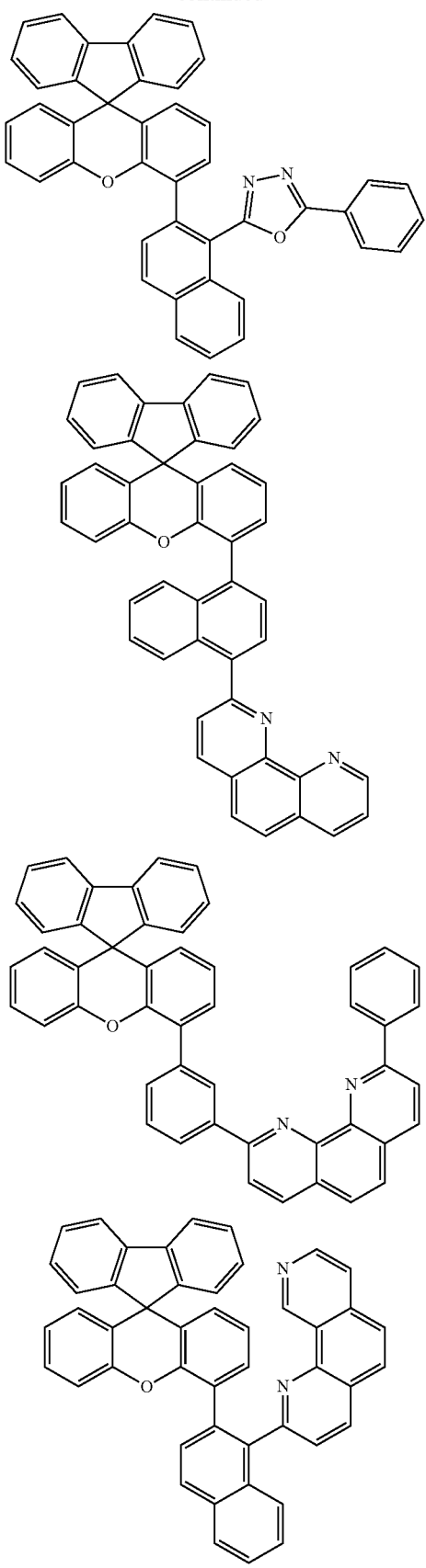
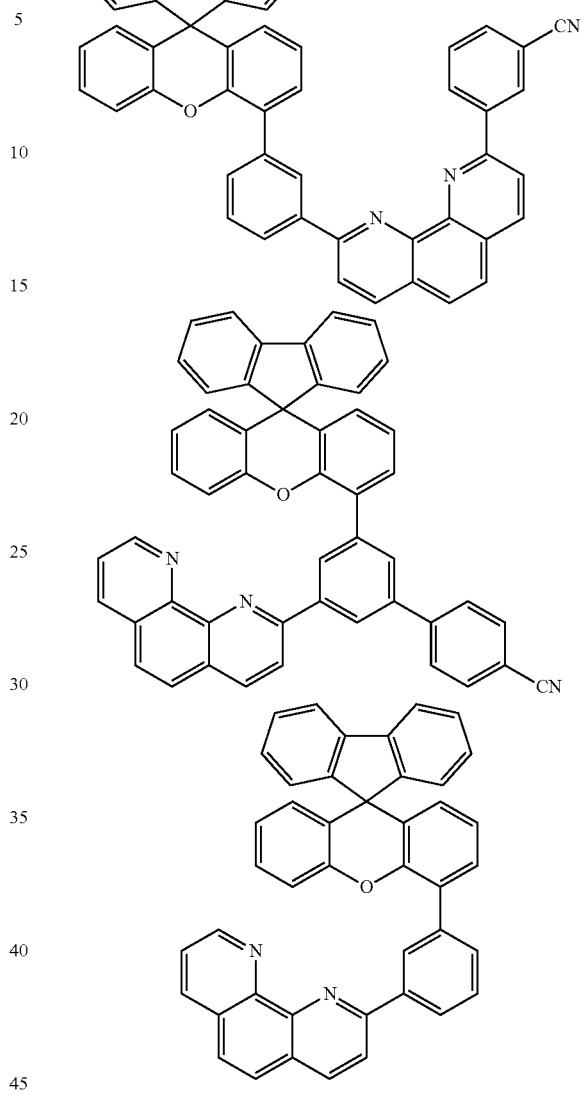

One embodiment of the present specification provides an organic light emitting device comprising a first electrode; a second electrode provided opposite to the first electrode; and one or more organic material layers provided between the first electrode and the second electrode, wherein the heterocyclic compound represented by Chemical Formula 1 is comprised in one or more layers of the one or more organic material layers.

According to one embodiment of the present specification, the organic material layer of the organic light emitting device of the present specification may be formed in a single layer structure, but may be formed in a multilayer structure in which two or more organic material layers are laminated. For example, the organic light emitting device of the present disclosure may have a structure comprising a hole injection layer, a hole transfer layer, an electron blocking layer, a light emitting layer, a hole blocking layer, an electron transfer layer, an electron injection layer and the like as the organic material layer. However, the structure of the organic light emitting device is not limited thereto, and may include less or more numbers of organic material layers.

For example, structures of an organic light emitting device of the present specification may be as illustrated in FIG. 1 and FIG. 2, but are not limited thereto.

FIG. 1 illustrates a structure of an organic light emitting device (10) in which a first electrode (30), a light emitting layer (40) and a second electrode (50) are consecutively laminated on a substrate (20). FIG. 1 is an exemplary structure of an organic light emitting device according to one embodiment of the present specification, and other organic material layers may be further included.

FIG. 2 illustrates a structure of an organic light emitting device (11) in which a first electrode (30), a hole injection layer (60), a hole transfer layer (70), a light emitting layer (40), an electron transfer layer (80), an electron injection layer (90) and a second electrode (50) are consecutively laminated on a substrate (20). FIG. 2 is an exemplary structure of an organic light emitting device according to an embodiment of the present specification, and other organic material layers may be further included.

According to one embodiment of the present specification, the heterocyclic compound represented by Chemical Formula 1 is comprised in one or more layers of an electron injection layer, an electron transfer layer and a layer carrying out electron injection and transfer at the same time.

In one embodiment of the present specification, when using the heterocyclic compound represented by Chemical Formula 1 in the organic material layer capable of carrying out electron injection and electron transfer at the same time, an n-type dopant used in the art may be mixed thereto.

In one embodiment of the present specification, when an n-type dopant is further included in the electron transfer layer, the electron injection layer or the layer carrying out electron injection and electron transfer at the same time in addition to the compound of Chemical Formula 1, a weight ratio of the compound of Chemical Formula 1 and the n-type dopant may be from 1:100 to 100:1. The weight ratio may be specifically from 1:10 to 10:1. The weight ratio may be more specifically 1:1.

In one embodiment of the present specification, the n-type dopant may be a metal complex and the like, and may use an alkali metal such as Li, Na, K, Rb, Cs or Fr; an alkali-earth metal such as Be, Mg, Ca, Sr, Ba or Ra; a rare-earth metal such as La, Ce, Pr, Nd, Sm, Eu, Tb, Th, Dy, Ho, Er, Em, Gd, Yb, Lu, Y or Mn; or a metal compound including one or more metals of the above-mentioned metals, however, the n-type dopant is not limited thereto, and those known in the art may be used. According to one embodiment, the electron transfer layer, the electron injection layer or the layer carrying out electron injection and electron transfer at the same time including the compound of Chemical Formula 1 may further include LiQ.

According to one embodiment of the present specification, the heterocyclic compound represented by Chemical Formula 1 is comprised in an electron control layer.

According to one embodiment of the present specification, the organic light emitting device may include one or more electron control layers, and the heterocyclic compound represented by Chemical Formula 1 may be comprised in one of the one or more electron control layers, or may be included in each of the two or more electron control layers.

According to one embodiment of the present specification, the one or more organic material layers may further include one or more layers selected from the group consisting of a hole injection layer, a hole transfer layer, a light emitting layer, an electron transfer layer and an electron injection layer.

According to one embodiment of the present specification, the organic light emitting device may include one or more hole transfer layers, and the one or more hole transfer layers may be each formed with materials the same as or different from each other.

The organic light emitting device of the present specification may be manufactured using materials and methods known in the art, except that one or more layers of the organic material layers comprise the heterocyclic compound of the present specification, that is, the heterocyclic compound represented by Chemical Formula 1.

When the organic light emitting device includes a plurality of organic material layers, the organic material layers may be formed with materials the same as or different from each other.

For example, the organic light emitting device of the present specification may be manufactured by consecutively laminating a first electrode, an organic material layer and a second electrode on a substrate. Herein, the organic light emitting device may be manufactured by forming a first electrode on a substrate by depositing a metal, a metal oxide having conductivity, or an alloy thereof using a physical vapor deposition (PVD) method such as sputtering or e-beam evaporation, and forming an organic material layer including a hole injection layer, a hole transfer layer, a light emitting layer and an electron transfer layer thereon, and then depositing a material capable of being used as a second electrode thereon. In addition to such a method, the organic light emitting device may also be manufactured by consecutively depositing a second electrode material, an organic material layer and a first electrode material on a substrate. In addition, the heterocyclic compound represented by Chemical Formula 1 may be formed into an organic material layer using a solution coating method as well as a vacuum deposition method when manufacturing the organic light emitting device. Herein, the solution coating method means spin coating, dip coating, doctor blading, inkjet printing, screen printing, a spray method, roll coating and the like, but is not limited thereto.

According to one embodiment of the present specification, the first electrode is an anode, and the second electrode is a cathode.

According to another embodiment of the present specification, the first electrode is a cathode, and the second electrode is an anode.

As the anode material, materials having large work function are normally preferable so that hole injection to an organic material layer is smooth. Specific examples of the anode material capable of being used in the present disclosure include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly[3,4-(ethylene-1,2-dioxy)thiophene] (PEDOT), polypyrrole and polyaniline, but are not limited thereto.

As the cathode material, materials having small work function are normally preferable so that electron injection to an organic material layer is smooth. Specific examples of the cathode material include metals such as magnesium, calcium, sodium, potassium, titanium, indium, yttrium, lithium, gadolinium, aluminum, silver, tin and lead, or alloys thereof; multilayer structure materials such as LiF/Al, $LiO_2$/Al or Mg/Ag, and the like, but are not limited thereto.

The hole injection layer is a layer that injects holes from an electrode, and the hole injection material is preferably a compound that has an ability to transfer holes, therefore, has a hole injection effect in an anode, has an excellent hole injection effect for a light emitting layer or a light emitting material, prevents excitons generated in the light emitting layer from moving to an electron injection layer or an electron injection material, and in addition, has an excellent thin film forming ability. The highest occupied molecular orbital (HOMO) of the hole injection material is preferably in between the work function of an anode material and the HOMO of surrounding organic material layers. Specific examples of the hole injection material include metal porphyrins, oligothiophene, arylamine-based organic materials, hexanitrile hexaazatriphenylene-based organic materials, quinacridone-based organic materials, perylene-based organic materials, anthraquinone, and polyaniline- and polythiophene-based conductive polymers, and the like, but are not limited thereto.

The hole transfer layer is a layer that receives holes from a hole injection layer and transfers the holes to a light emitting layer, and as the hole transfer material, materials capable of receiving holes from an anode or a hole injection layer, moving the holes to a light emitting layer, and having high mobility for the holes are suitable. Specific examples thereof include arylamine-based organic materials, conductive polymers, block copolymers having conjugated parts and non-conjugated parts together, and the like, but are not limited thereto.

The light emitting material of the light emitting layer is a material capable of emitting light in a visible light region by receiving holes and electrons from a hole transfer layer and an electron transfer layer, respectively, and binding the holes and the electrons, and is preferably a material having favorable quantum efficiency for fluorescence or phosphorescence. Specific examples thereof include 8-hydroxyquinoline aluminum complexes ($Alq_3$); carbazole series compounds; dimerized styryl compounds; BAlq; 10-hydroxybenzoquinoline-metal compounds; benzoxazole, benzthiazole and benzimidazole series compounds; poly(p-phenylenevinylene) (PPV) series polymers; spiro compounds; polyfluorene, rubrene, and the like, but are not limited thereto.

The light emitting layer may include a host material and a dopant material.

As the host material of the light emitting layer, fused aromatic ring derivatives, heteroring-containing compounds or the like may be used. As the fused aromatic ring derivative, anthracene derivatives, pyrene derivatives, naphthalene derivatives, pentacene derivatives, phenanthrene compounds, fluoranthene compounds and the like may be included, and as the heteroring-containing compound, carbazole derivatives, dibenzofuran derivatives, ladder-type furan compounds, pyrimidine derivatives and the like may be included, however, the host material is not limited thereto.

As the dopant material of the light emitting layer, aromatic amine derivatives, styrylamine compounds, boron complexes, fluoranthene compounds, metal complexes and the like may be included. The aromatic amine derivative is a fused aromatic ring derivative having a substituted or unsubstituted arylamine group, and arylamine group-including pyrene, anthracene, chrysene, peryflanthene and the like may be used. As the styrylamine compound, a compound in which substituted or unsubstituted arylamine is substituted with at least one arylvinyl group may be used. Examples of the styrylamine compound may include styrylamine, styryldiamine, styryltriamine, styryltetramine and the like, but are not limited thereto. As the metal complex, iridium complexes, platinum complexes and the like may be used, however, the metal complex is not limited thereto.

The electron control layer is a layer controlling performance of the whole device by blocking holes from inflowing to a cathode from a light emitting layer and controlling electrons inflowing to the light emitting layer. As the electron control material, compounds having capabilities of preventing holes from inflowing to a cathode from a light emitting layer, and controlling injected electrons for the light emitting layer or light emitting material are preferred. As the electron control material, proper materials may be used depending on the constitution of the organic material layer used in a device. The electron control layer is located between a light emitting layer and a cathode, and preferably, is provided directly adjoining the light emitting layer.

The electron transfer layer is a layer that receives electrons from an electron injection layer and transfers the electrons to a light emitting layer. As the electron transfer material, materials capable of favorably receiving electrons from a cathode, moving the electrons to a light emitting layer, and having high mobility for the electrons are suited. Examples of the electron transfer material include Al complexes of 8-hydroxyquinoline; complexes including $Alq_3$; organic radical compounds; hydroxyflavon-metal complexes, and the like, but are not limited thereto. The electron transfer layer may be used together with any desired cathode material as used in the art. In one embodiment, materials having low work function; and an aluminum layer or a silver layer may be used as the cathode material. Examples of the material having low work function may include cesium, barium, calcium, ytterbium, samarium and the like, and after forming a layer with the above-mentioned material, an aluminum layer or a silver layer may be formed on the layer.

The electron injection layer is a layer injecting electrons received from an electrode to a light emitting layer. As the electron injection material, compounds having an electron transferring ability, having an electron injection effect from a cathode, having an excellent electron injection effect for a light emitting layer or light emitting material, and preventing excitons generated in the light emitting layer from moving to a hole injection layer, and in addition thereto, having an excellent thin film forming ability are preferably used. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone or the like, and derivatives thereof, metal complex compounds, nitrogen-containing 5-membered ring derivatives, and the like, but are not limited thereto.

The metal complex compound includes 8-hydroxyquinolinato lithium, bis(8-hydroxyquinolinato) zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato) gallium, bis(10-hydroxybenzo[h]quinolinato)berylium, bis(10-hydroxybenzo[h]quinolinato) zinc, bis(2-methyl-8-quinolinato) chlorogallium, bis(2-methyl-8-quinolinato) (o-cresolato) gallium, bis(2-methyl-8-quinolinato) (1-naphtholato)aluminum, bis(2-methyl-8-quinolinato) (2-naphtholato)gallium and the like, but is not limited thereto.

The organic light emitting device according to the present specification may be a top-emission type, a bottom-emission type or a dual-emission type depending on the materials used.

According to one embodiment of the present specification, the heterocyclic compound represented by Chemical Formula 1 may be included in organic solar cells or organic transistors in addition to organic light emitting devices.

Hereinafter, the present specification will be described in detail with reference to examples. However, the examples according to the present specification may be modified to various other forms, and the scope of the present specification is not to be construed as being limited to the examples described below. Examples of the present specification are provided in order to more completely describe the present specification to those having average knowledge in the art.

Synthesis Example

<Preparation Example 1> Synthesis of Compound E1

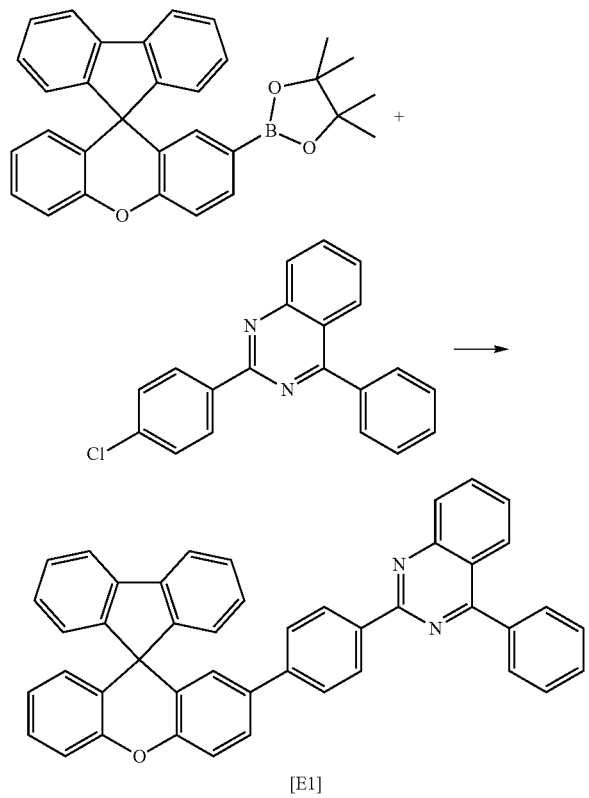

[E1]

After completely dissolving compounds of 4,4,5,5-tetramethyl-2-(spiro[fluorene-9,9'-xanthen]-2'-yl)-1,3,2-dioxaborolane (10.0 g, 21.8 mmol) and 2-(4-chlorophenyl)-4-phenylquinazoline (6.9 g, 21.8 mmol) in tetrahydrofuran (100 ml), potassium carbonate (9.0 g, 65.4 mmol) dissolved in water (50 ml) was added thereto, and after introducing tetrakistriphenyl-phosphino palladium (756 mg, 0.65 mmol) thereto, the result was heated and stirred for 8 hours. After lowering the temperature to room temperature and terminating the reaction, the potassium carbonate solution was removed to filter white solids. The filtered white solids were washed twice each with tetrahydrofuran and ethyl acetate to prepare Compound E1 (11.9 g, yield 89%).

MS[M+H]$^+$=613

<Preparation Example 2> Synthesis of Compound E2

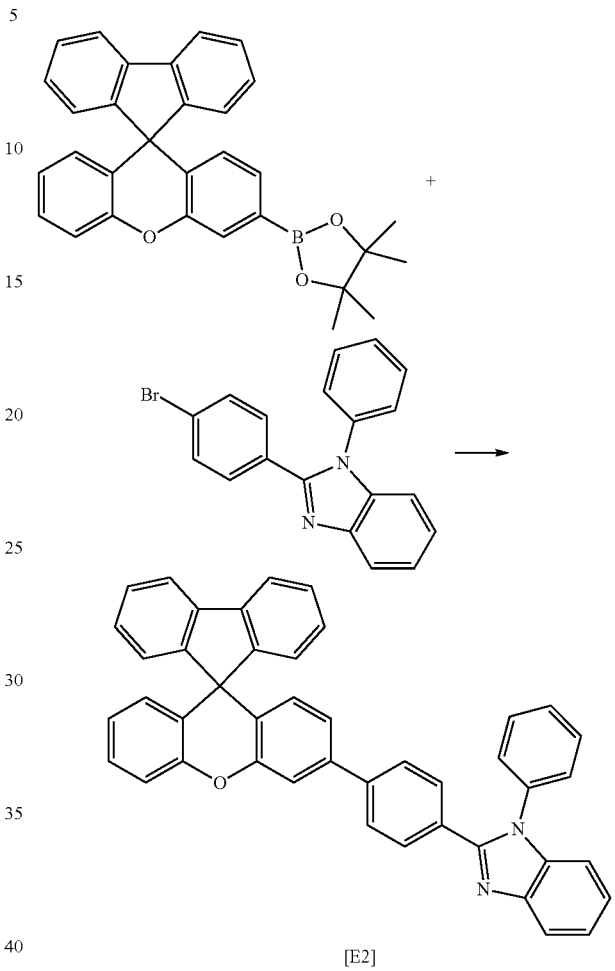

[E2]

Compound E2 was prepared in the same manner as in Preparation Example 1 except that each starting material was as in the above-described reaction formula.

MS[M+H]$^+$=601

<Preparation Example 3> Synthesis of Compound E3

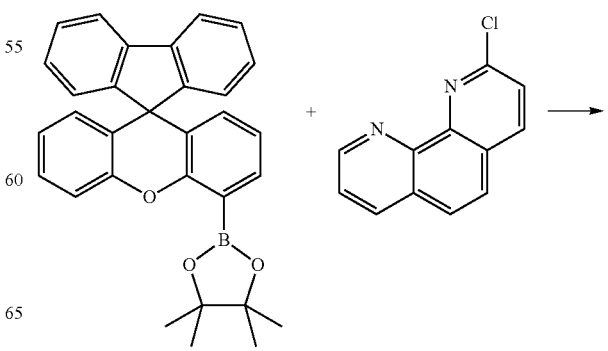

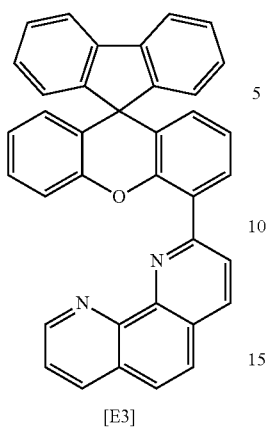

[E3]

Compound E3 was prepared in the same manner as in Preparation Example 1 except that each starting material was as in the above-described reaction formula.

MS[M+H]$^+$=511

<Preparation Example 4> Synthesis of Compound E4

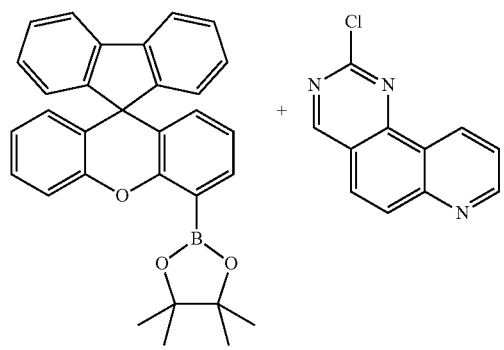

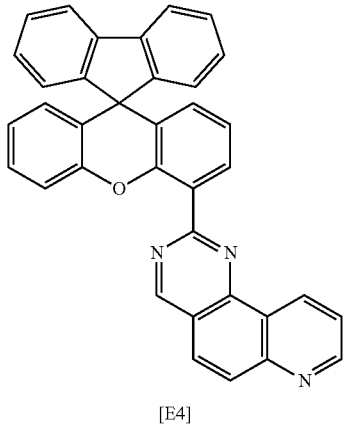

[E4]

Compound E4 was prepared in the same manner as in Preparation Example 1 except that each starting material was as in the above-described reaction formula.

MS[M+H]$^+$=(512)

<Preparation Example 5> Synthesis of Compound E5

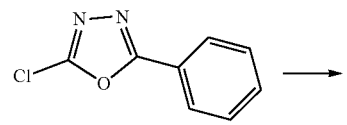

+

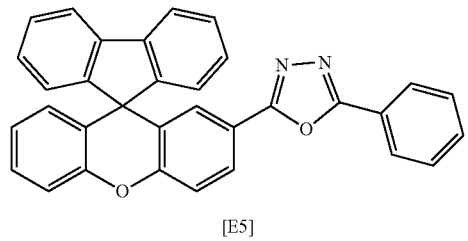

[E5]

Compound E5 was prepared in the same manner as in Preparation Example 1 except that each starting material was as in the above-described reaction formula.

MS[M+H]$^+$=477

<Preparation Example 6> Synthesis of Compound E6

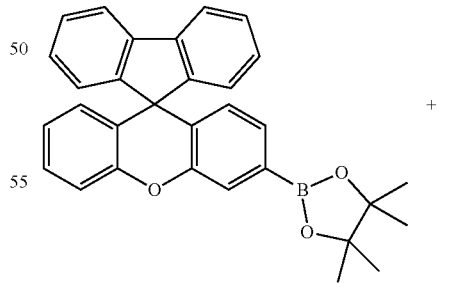

+

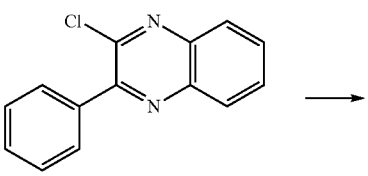

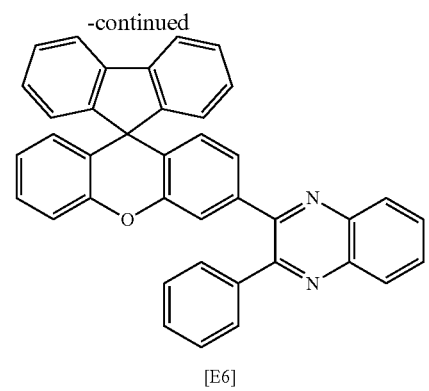

[E6]

Compound E6 was prepared in the same manner as in Preparation Example 1 except that each starting material was as in the above-described reaction formula.

MS[M+H]$^+$=537

<Preparation Example 7> Synthesis of Compound E7

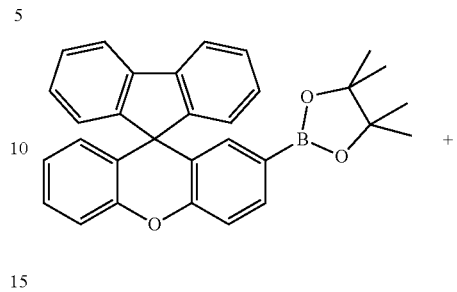

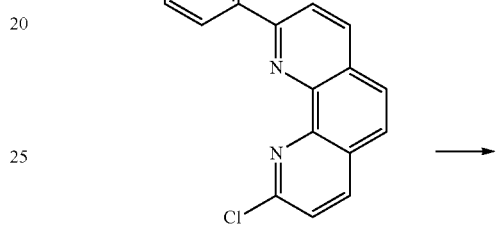

[E7]

Compound E7 was prepared in the same manner as in Preparation Example 1 except that each starting material was as in the above-described reaction formula.

MS[M+H]$^+$=(589)

<Preparation Example 8> Synthesis of Compound E8

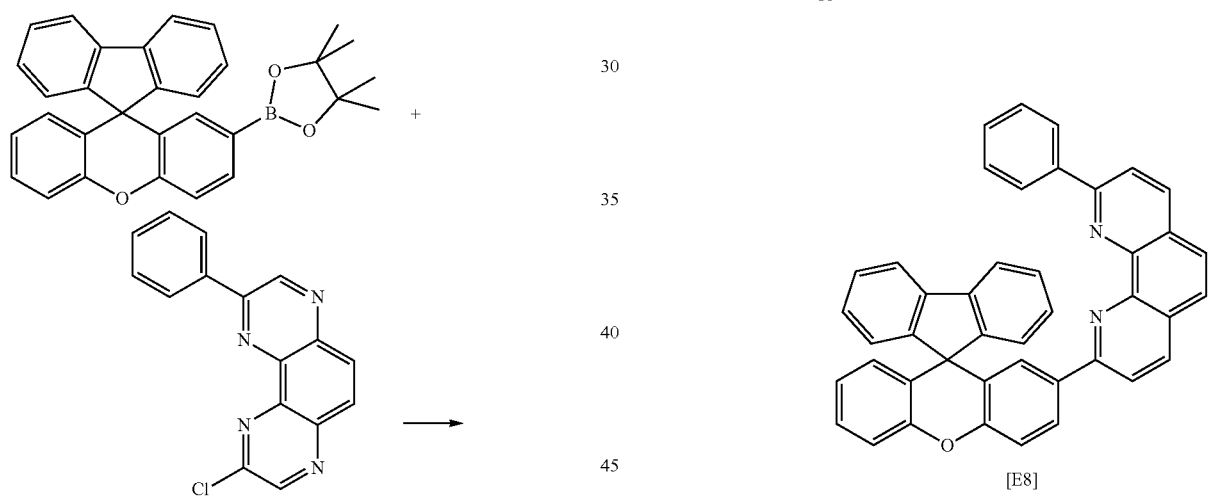

[E8]

Compound E8 was prepared in the same manner as in Preparation Example 1 except that each starting material was as in the above-described reaction formula.

MS [M+H]$^+$=587

<Preparation Example 11> Synthesis of Compound E11

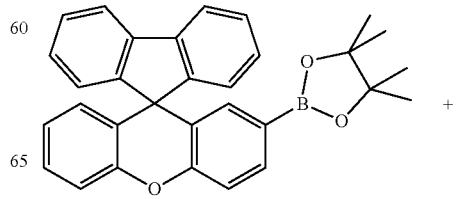

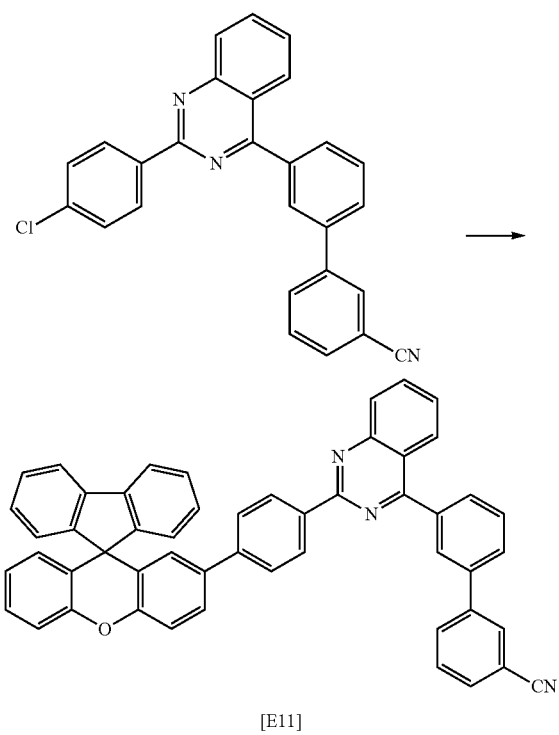

[E11]

Compound E11 was prepared in the same manner as in Preparation Example 1 except that each starting material was as in the above-described reaction formula.

MS[M+H]$^+$=714

<Preparation Example 12> Synthesis of Compound E12

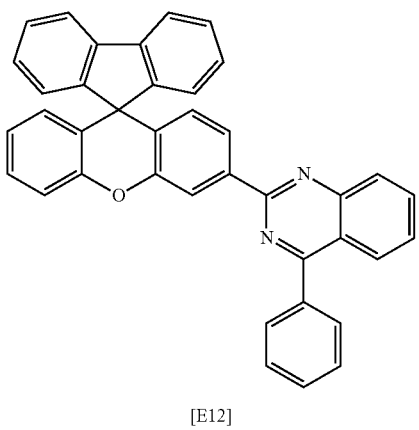

[E12]

Compound E12 was prepared in the same manner as in Preparation Example 1 except that each starting material was as in the above-described reaction formula.

MS[M+H]$^+$=537

<Preparation Example 13> Synthesis of Compound E13

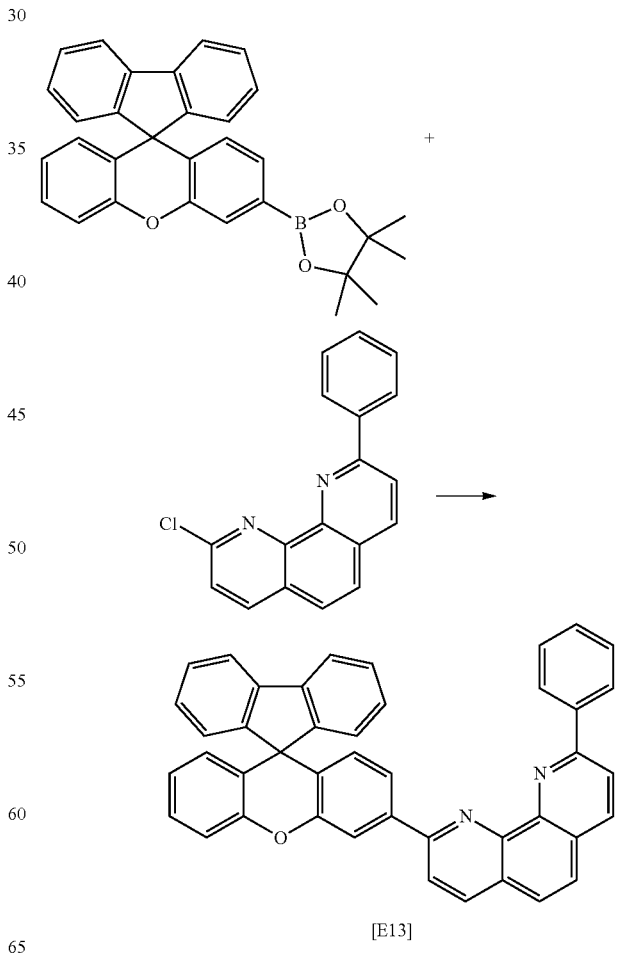

[E13]

Compound E13 was prepared in the same manner as in Preparation Example 1 except that each starting material was as in the above-described reaction formula.
MS[M+H]⁺=587

<Preparation Example 14> Synthesis of Compound E14

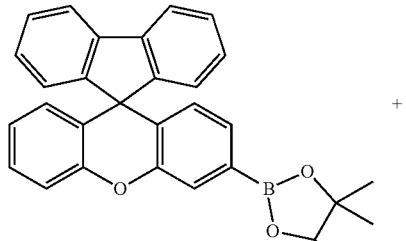

+

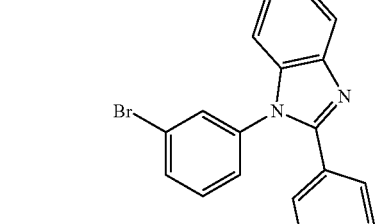

→

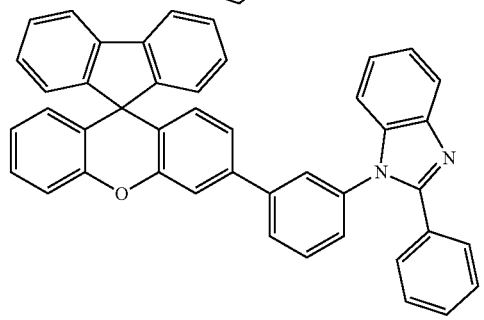

[E14]

Compound E14 was prepared in the same manner as in Preparation Example 1 except that each starting material was as in the above-described reaction formula.
MS[M+H]⁺=601

<Preparation Example 15> Synthesis of Compound E15

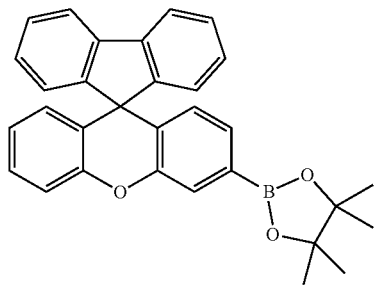

+

-continued

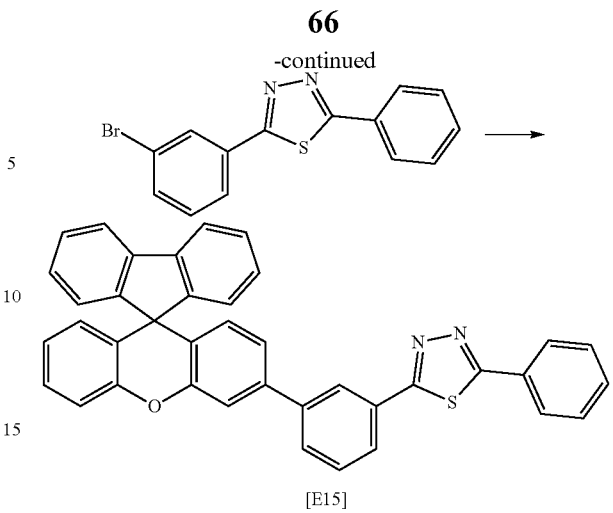

[E15]

Compound E15 was prepared in the same manner as in Preparation Example 1 except that each starting material was as in the above-described reaction formula.
MS[M+H]⁺=569

<Preparation Example 16> Synthesis of Compound E16

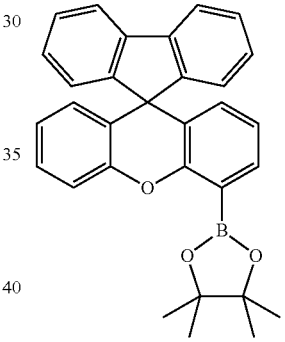

+

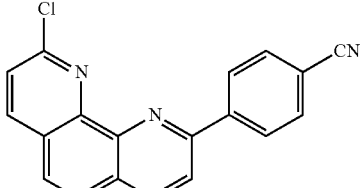

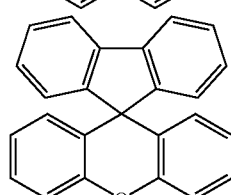

[E16]

Compound E16 was prepared in the same manner as in Preparation Example 1 except that each starting material was as in the above-described reaction formula.

MS[M+H]$^+$=612

<Preparation Example 17> Synthesis of Compound E17

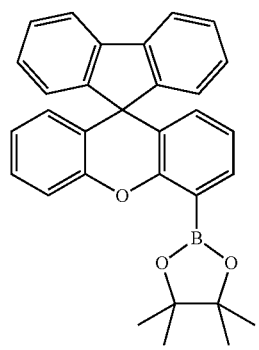

+

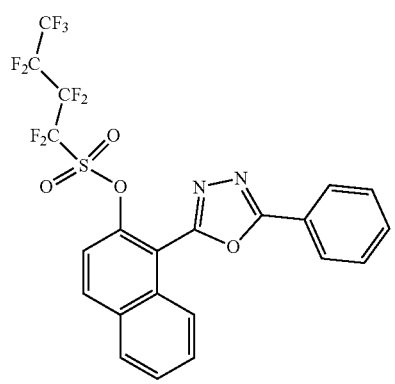

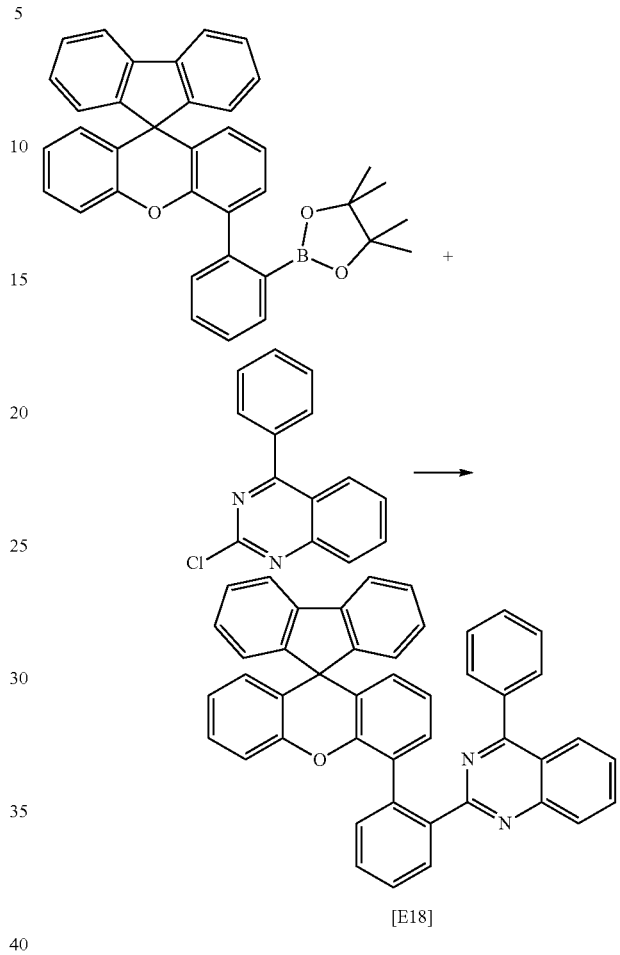

[E17]

Compound E17 was prepared in the same manner as in Preparation Example 1 except that each starting material was as in the above-described reaction formula.

MS[M+H]$^+$=603

<Preparation Example 18> Synthesis of Compound E18

Compound E18 was prepared in the same manner as in Preparation Example 1 except that each starting material was as in the above-described reaction formula.

MS[M+H]$^+$=614

Example 1-1

A glass substrate on which indium tin oxide (ITO) was coated as a thin film to a thickness of 1,000 Å was placed in detergent-dissolved distilled water and ultrasonic cleaned. Herein, a product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol, acetone and methanol, then dried, and then transferred to a plasma cleaner. In addition, the substrate was cleaned for 5 minutes using oxygen plasma, and then transferred to a vacuum depositor.

On the transparent ITO electrode prepared as above, a hole injection layer was formed by thermal vacuum depositing the following compound [HI-A] to a thickness of 600 Å. A hole transfer layer was formed on the hole injection layer by vacuum depositing hexaazatriphenylene (HAT) of the following chemical formula to a thickness of 50 Å and the following compound [HT-A] (600 Å) in consecutive order.

Subsequently, a light emitting layer was formed on the hole transfer layer to a film thickness of 200 Å by vacuum depositing the following compounds [BH] and [BD] in a weight ratio of 25:1.

On the light emitting layer, an electron injection and transfer layer was formed to a thickness of 350 Å by vacuum depositing Compound E1 and the following lithium quinolate [LiQ] compound in a weight ratio of 1:1. A cathode was formed on the electron injection and transfer layer by depositing lithium fluoride (LiF) to a thickness of 10 Å and aluminum to a thickness of 1,000 Å in consecutive order.

An organic light emitting device was manufactured by maintaining, in the above-mentioned processes, the deposition rates of the organic materials at 0.4 Å/sec to 0.9 Å/sec, the deposition rates of the lithium fluoride and the aluminum of the cathode at 0.3 Å/sec and 2 Å/sec, respectively, and the degree of vacuum during the deposition at $1 \times 10^7$ torr to $5 \times 10^8$ torr.

[HAT]
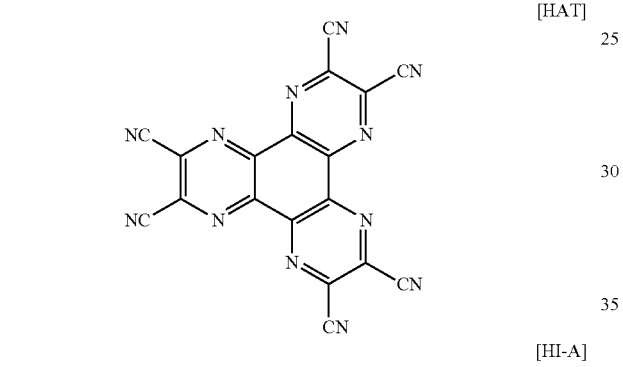

[HI-A]
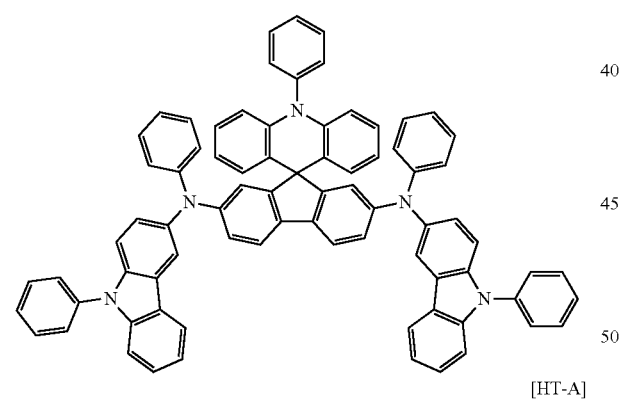

[HT-A]
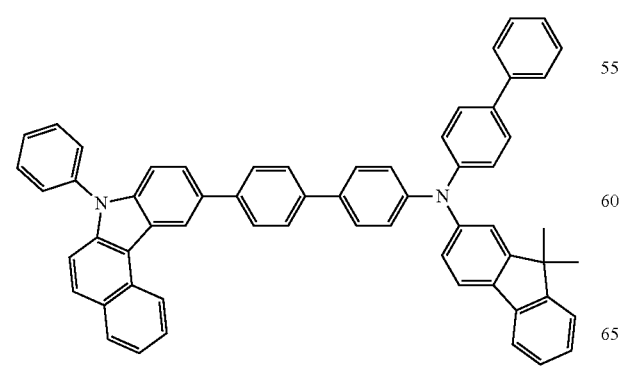

[LiQ]
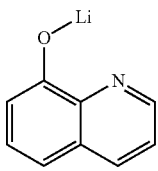

[BH]
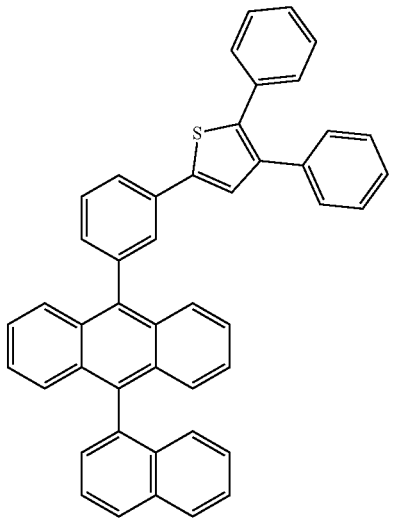

[BD]
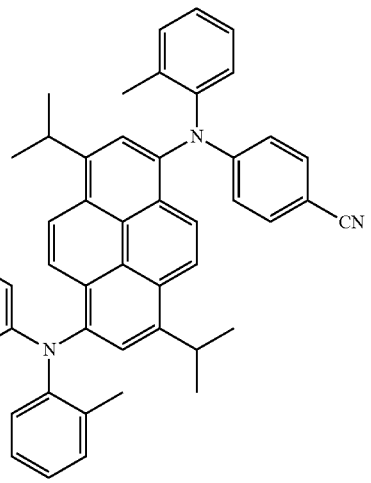

[ET-1-A]
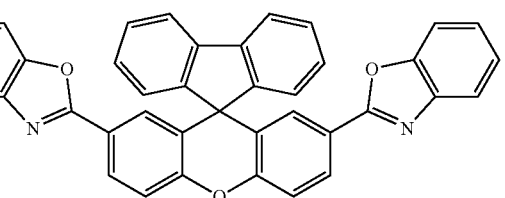

-continued

[ET-1-B]

[ET-1-C]

[ET-1-D]

[ET-1-E]

-continued

[ET-1-F]

[ET-1-G]

[ET-1-H]

[ET-1-I]

[ET-1-J]

-continued

[ET-1-K]

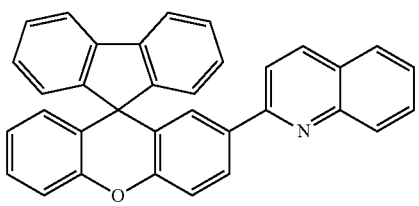

[ET-1-L]

[ET-1-M]

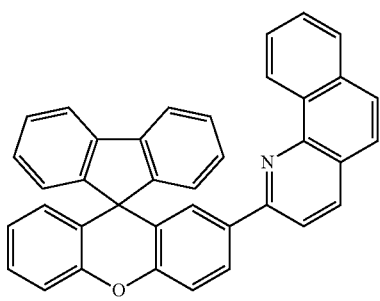

[ET-1-N]

[ET-1-O]

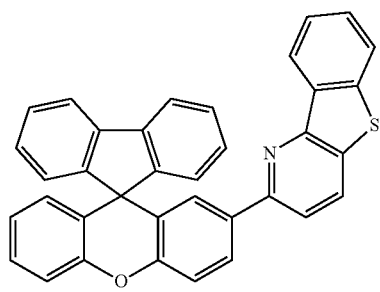

Example 1-2

An organic light emitting device was manufactured in the same manner as in Example 1-1 except that Compound E2 was used instead of Compound E1.

Example 1-3

An organic light emitting device was manufactured in the same manner as in Example 1-1 except that Compound E3 was used instead of Compound E1.

Example 1-4

An organic light emitting device was manufactured in the same manner as in Example 1-1 except that Compound E4 was used instead of Compound E1.

Example 1-5

An organic light emitting device was manufactured in the same manner as in Example 1-1 except that Compound E5 was used instead of Compound E1.

Example 1-6

An organic light emitting device was manufactured in the same manner as in Example 1-1 except that Compound E6 was used instead of Compound E1.

Example 1-7

An organic light emitting device was manufactured in the same manner as in Example 1-1 except that Compound E7 was used instead of Compound E1.

Example 1-8

An organic light emitting device was manufactured in the same manner as in Example 1-1 except that Compound E8 was used instead of Compound E1.

Example 1-11

An organic light emitting device was manufactured in the same manner as in Example 1-1 except that Compound E11 was used instead of Compound E1.

Example 1-12

An organic light emitting device was manufactured in the same manner as in Example 1-1 except that Compound E12 was used instead of Compound E1.

Example 1-13

An organic light emitting device was manufactured in the same manner as in Example 1-1 except that Compound E13 was used instead of Compound E1.

Example 1-14

An organic light emitting device was manufactured in the same manner as in Example 1-1 except that Compound E14 was used instead of Compound E1.

Example 1-15

An organic light emitting device was manufactured in the same manner as in Example 1-1 except that Compound E15 was used instead of Compound E1.

Example 1-16

An organic light emitting device was manufactured in the same manner as in Example 1-1 except that Compound E16 was used instead of Compound E1.

Example 1-17

An organic light emitting device was manufactured in the same manner as in Example 1-1 except that Compound E17 was used instead of Compound E1.

Example 1-18

An organic light emitting device was manufactured in the same manner as in Example 1-1 except that Compound E18 was used instead of Compound E1.

Comparative Example 1-1

An organic light emitting device was manufactured in the same manner as in Example 1-1 except that Compound ET-1-A was used instead of Compound E1.

Comparative Example 1-2

An organic light emitting device was manufactured in the same manner as in Example 1-1 except that Compound ET-1-B was used instead of Compound E1.

Comparative Example 1-3

An organic light emitting device was manufactured in the same manner as in Example 1-1 except that Compound ET-1-C was used instead of Compound E1.

Comparative Example 1-4

An organic light emitting device was manufactured in the same manner as in Example 1-1 except that Compound ET-1-D was used instead of Compound E1.

Comparative Example 1-5

An organic light emitting device was manufactured in the same manner as in Example 1-1 except that Compound ET-1-E was used instead of Compound E1.

Comparative Example 1-6

An organic light emitting device was manufactured in the same manner as in Example 1-1 except that Compound ET-1-F was used instead of Compound E1.

Comparative Example 1-7

An organic light emitting device was manufactured in the same manner as in Example 1-1 except that Compound ET-1-G was used instead of Compound E1.

Comparative Example 1-8

An organic light emitting device was manufactured in the same manner as in Example 1-1 except that Compound ET-1-H was used instead of Compound E1.

Comparative Example 1-9

An organic light emitting device was manufactured in the same manner as in Example 1-1 except that Compound ET-1-I was used instead of Compound E1.

Comparative Example 1-10

An organic light emitting device was manufactured in the same manner as in Example 1-1 except that Compound ET-1-J was used instead of Compound E1.

Comparative Example 1-11

An organic light emitting device was manufactured in the same manner as in Example 1-1 except that Compound ET-1-K was used instead of Compound E1.

Comparative Example 1-12

An organic light emitting device was manufactured in the same manner as in Example 1-1 except that Compound ET-1-L was used instead of Compound E1.

Comparative Example 1-13

An organic light emitting device was manufactured in the same manner as in Example 1-1 except that Compound ET-1-M was used instead of Compound E1.

Comparative Example 1-14

An organic light emitting device was manufactured in the same manner as in Example 1-1 except that Compound ET-1-N was used instead of Compound E1.

Comparative Example 1-15

An organic light emitting device was manufactured in the same manner as in Example 1-1 except that Compound ET-1-O was used instead of Compound E1.

For the organic light emitting devices manufactured using the methods of Examples 1-1 to 1-8 and 1-11 to 1-18, and Comparative Examples 1-1 to 1-15 described above, a driving voltage and light emission efficiency were measured at current density of 10 mA/cm$^2$, and time taken for the luminance decreasing to 90% compared to its initial luminance ($T_{90}$) was measured at current density of 20 mA/cm$^2$. The results are shown in the following Table 1.

TABLE 1

| | Compound | Voltage (V@10 mA/cm$^2$) | Efficiency (cd/A@10 mA/cm$^2$) | Color Coordinate (x, y) | Lifetime (h) $T_{90}$ at 20 mA/cm$^2$ |
|---|---|---|---|---|---|
| Example 1-1 | E1 | 4.40 | 5.07 | (0.142, 0.096) | 201 |
| Example 1-2 | E2 | 4.27 | 5.39 | (0.142, 0.096) | 140 |
| Example 1-3 | E3 | 4.39 | 5.02 | (0.142, 0.096) | 148 |
| Example 1-4 | E4 | 4.40 | 4.94 | (0.142, 0.097) | 200 |
| Example 1-5 | E5 | 4.39 | 4.98 | (0.142, 0.097) | 126 |
| Example 1-6 | E6 | 4.36 | 4.95 | (0.142, 0.096) | 130 |
| Example 1-7 | E7 | 4.30 | 5.02 | (0.142, 0.097) | 159 |
| Example 1-8 | E8 | 4.30 | 5.40 | (0.142, 0.099) | 230 |
| Example 1-11 | E11 | 4.42 | 5.10 | (0.142, 0.096) | 220 |
| Example 1-12 | E12 | 4.38 | 5.17 | (0.142, 0.097) | 194 |

TABLE 1-continued

| Compound | | Voltage (V@10 mA/cm$^2$) | Efficiency (cd/A@10 mA/cm$^2$) | Color Coordinate (x, y) | Lifetime (h) T$_{90}$ at 20 mA/cm$^2$ |
|---|---|---|---|---|---|
| Example 1-13 | E13 | 4.29 | 5.35 | (0.142, 0.096) | 231 |
| Example 1-14 | E14 | 4.29 | 5.11 | (0.142, 0.097) | 141 |
| Example 1-15 | E15 | 4.32 | 4.95 | (0.142, 0.097) | 130 |
| Example 1-16 | E16 | 4.30 | 5.31 | (0.142, 0.097) | 255 |
| Example 1-17 | E17 | 4.36 | 4.93 | (0.142, 0.097) | 126 |
| Example 1-18 | E18 | 4.28 | 5.20 | (0.142, 0.096) | 199 |
| Comparative Example 1-1 | ET-1-A | 4.72 | 3.91 | (0.142, 0.098) | 90 |
| Comparative Example 1-2 | ET-1-B | 4.84 | 4.01 | (0.142, 0.102) | 87 |
| Comparative Example 1-3 | ET-1-C | 4.91 | 3.99 | (0.142, 0.096) | 91 |
| Comparative Example 1-4 | ET-1-D | 4.88 | 4.00 | (0.142, 0.096) | 55 |
| Comparative Example 1-5 | ET-1-E | 5.01 | 3.61 | (0.142, 0.096) | 75 |
| Comparative Example 1-6 | ET-1-F | 5.15 | 3.48 | (0.142, 0.096) | 60 |
| Comparative Example 1-7 | ET-1-G | 5.33 | 3.21 | (0.142, 0.096) | 60 |
| Comparative Example 1-8 | ET-1-H | 5.45 | 3.20 | (0.142, 0.096) | 55 |
| Comparative Example 1-9 | ET-1-I | 5.55 | 3.10 | (0.142, 0.096) | 62 |
| Comparative Example 1-10 | ET-1-J | 5.43 | 3.33 | (0.142, 0.096) | 78 |
| Comparative Example 1-11 | ET-1-K | 5.00 | 3.60 | (0.142, 0.097) | 98 |
| Comparative Example 1-12 | ET-1-L | 5.44 | 3.24 | (0.142, 0.096) | 44 |
| Comparative Example 1-13 | ET-1-M | 5.41 | 2.99 | (0.142, 0.097) | 50 |
| Comparative Example 1-14 | ET-1-N | 5.01 | 3.12 | (0.142, 0.097) | 33 |
| Comparative Example 1-15 | ET-1-O | 5.88 | 1.97 | (0.142, 0.097) | 44 |

From the results of Table 1, it was identified that the heterocyclic compound represented by Chemical Formula 1 according to one embodiment of the present specification was able to be used in an organic material layer capable of carrying out electron injection and electron transfer at the same time of an organic light emitting device.

Specifically, when comparing Examples 1-1 to 1-8 and 1-11 to 1-18 with Comparative Examples 1-1, 1-2, 1-3, 1-5, 1-7, 1-8 and 1-9, it was identified that the compound in which only one heteroaryl group substitutes in the spiro fluorene xanthen skeleton as in Chemical Formula 1 had excellent properties in terms of driving voltage, efficiency and lifetime in an organic light emitting device compared to the compound having two or more substituents in the spiro fluorene xanthen skeleton.

When referring to FIG. 3 and FIG. 4 illustrating 3D structures of Compounds E3 and E6 according to one embodiment of the present specification, it was identified that the molecules of the compounds had a horizontal structure, and when referring to FIG. 5 and FIG. 6 illustrating 3D structures of Compounds ET-1-E and ET-1-I, the A axis and the B axis were almost perpendicular to each other in each compound identifying that the molecule was very out of a horizontal structure.

As a result, when comparing FIG. 3 and FIG. 4 illustrating 3D structures of Compounds E3 and E6 according to one embodiment of the present specification and FIG. 5 and FIG. 6 illustrating 3D structures of Compounds ET-1-E and ET-1-I, it was seen that the heterocyclic compound represented by Chemical Formula 1 according to one embodiment of the present specification had a more horizontal structure due to a difference in orientation in the molecular 3D structure. Accordingly, the compound in which only one heteroaryl group substitutes in the spiro fluorene xanthen skeleton as in Chemical Formula 1 of Examples 1-1 to 1-8 and 1-11 to 1-18 had a strong tendency toward a horizontal structure of the molecule compared to the compound having two or more substituents in the spiro fluorene xanthen resulting in an increase in the electron mobility, and effects of low driving voltage, high efficiency and long lifetime are obtained in an organic light emitting device.

In addition, when comparing Examples 1-1 to 1-8 and 1-11 to 1-18 with Comparative Examples 1-4 and 1-6, it was identified that the structure of Chemical Formula 1 comprising spiro fluorene xanthen exhibited excellent properties in an organic light emitting device compared to the structure comprising a spiro fluorene group.

In addition, when comparing Examples 1-1 to 1-8 and 1-11 to 1-18 with Comparative Examples 1-11 to 1-15, it was identified that the structure of Chemical Formula 1 in which Ar1 comprises two or more Ns exhibited effects of low driving voltage, high efficiency and long lifetime in an organic light emitting device compared to the structure comprising one N.

The heterocyclic compound represented by Chemical Formula 1 according to one embodiment of the present specification is capable of having excellent properties by having excellent thermal stability, a deep HOMO level of 6.0 eV or higher, high triplet energy (ET) and hole stability.

In one embodiment of the present specification, when using the heterocyclic compound represented by Chemical Formula 1 in an organic material layer carrying out electron injection and electron transfer at the same time, an n-type dopant used in the art may be mixed thereto.

Accordingly, the heterocyclic compound represented by Chemical Formula 1 according to one embodiment of the present specification has low driving voltage and high efficiency, and is capable of enhancing device stability by hole stability of the compound.

Example 2-1

A glass substrate on which indium tin oxide (ITO) was coated as a thin film to a thickness of 1,000 Å was placed in detergent-dissolved distilled water and ultrasonic cleaned. Herein, a product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol, acetone and methanol, then dried, and then transferred to a plasma cleaner. In addition, the substrate was cleaned for 5 minutes using oxygen plasma, and then transferred to a vacuum depositor.

On the transparent ITO electrode prepared as above, a hole injection layer was formed by thermal vacuum depositing the following compound [HI-A] to a thickness of 600 Å. A hole transfer layer was formed on the hole injection layer by vacuum depositing hexaazatriphenylene (HAT) of the following chemical formula to a thickness of 50 Å and the following compound [HT-A] (600 Å) in consecutive order.

Subsequently, a light emitting layer was formed on the hole transfer layer to a film thickness of 200 Å by vacuum depositing the following compounds [BH] and [BD] in a weight ratio of 25:1.

On the light emitting layer, an electron control layer was formed to a thickness of 200 Å by vacuum depositing Compound E1. On the electron control layer, an electron injection and transfer layer was formed to a thickness of 150 Å by vacuum depositing the following compound [ET-1-J] and the following lithium quinolate [LiQ] compound in a weight ratio of 1:1. A cathode was formed on the electron injection and transfer layer by depositing lithium fluoride (LiF) to a thickness of 10 Å and aluminum to a thickness of 1,000 Å in consecutive order.

An organic light emitting device was manufactured by maintaining, in the above-mentioned processes, the deposition rates of the organic materials at 0.4 Å/sec to 0.9 Å/sec, the deposition rates of the lithium fluoride and the aluminum of the cathode at 0.3 Å/sec and 2 Å/sec, respectively, and the degree of vacuum during the deposition at $1 \times 10^7$ torr to $5 \times 10^8$ torr.

[HAT]

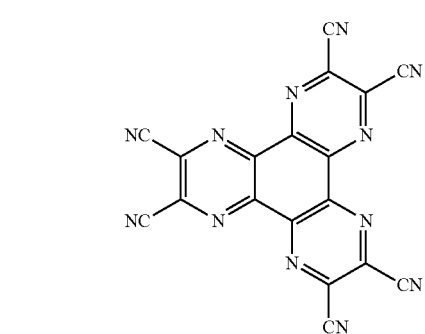

[HI-A]

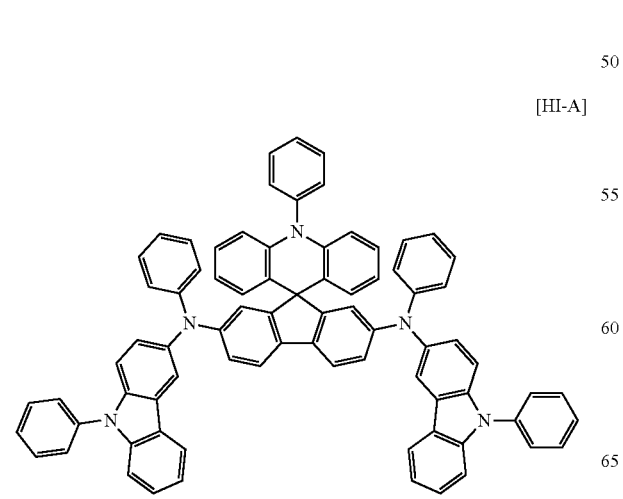

-continued

[HT-A]

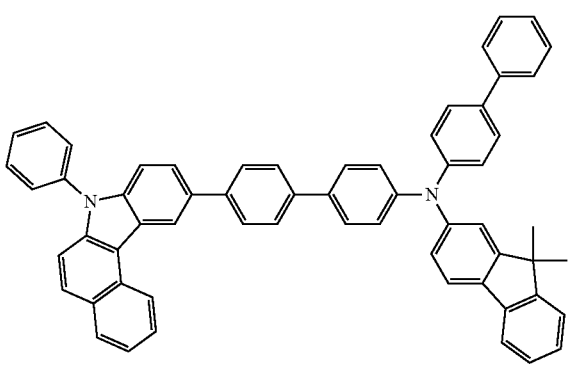

[LiQ]

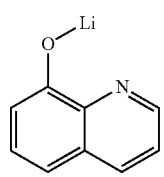

[BH]

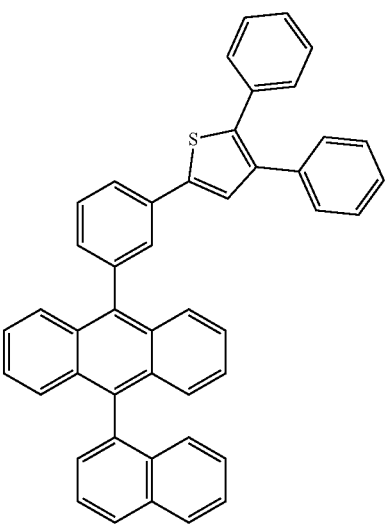

[BD]

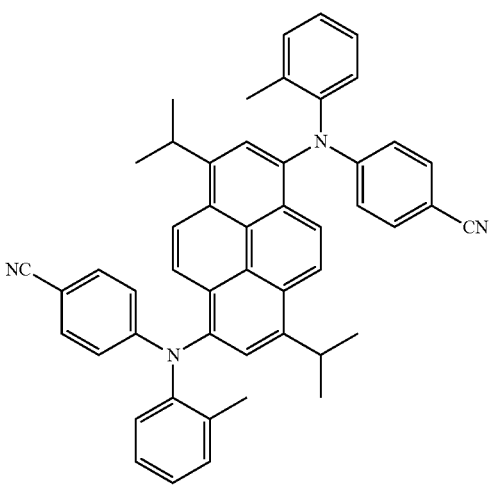

-continued
[ET-1-A]
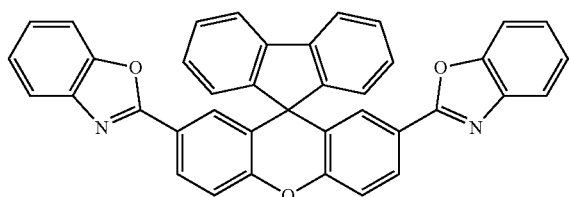
[ET-1-B]
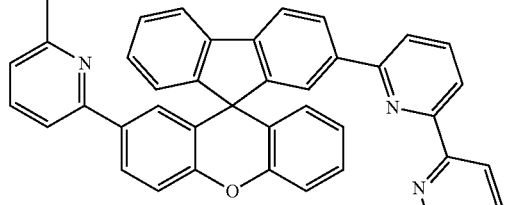
[ET-1-C]
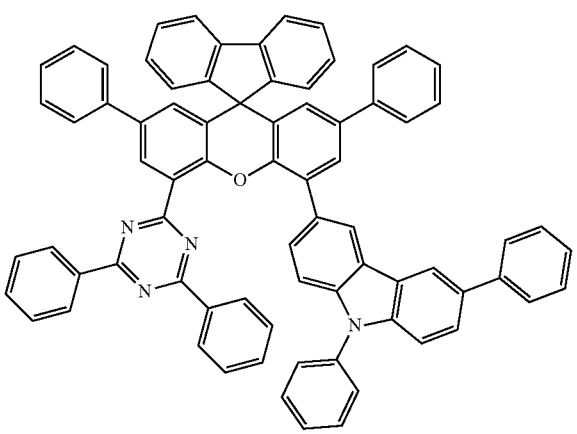
[ET-1-D]
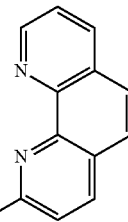
-continued
[ET-1-E]
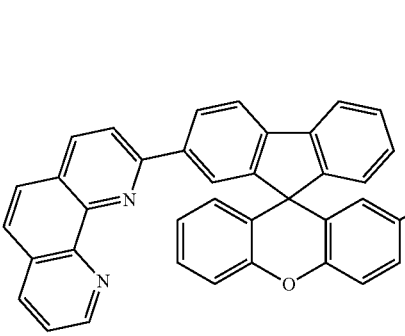
[ET-2-F]
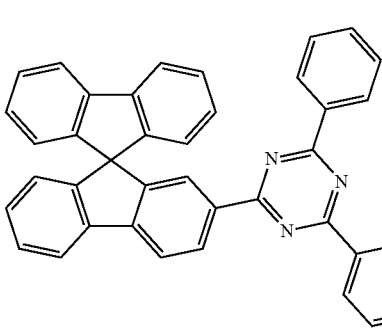
[ET-1-G]
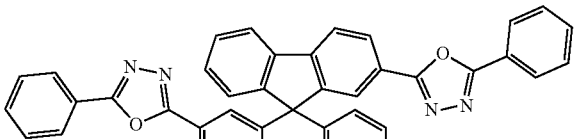
[ET-1-H]
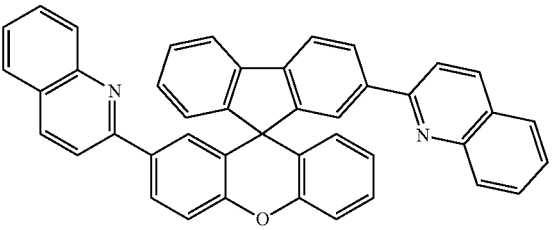
[ET-1-I]
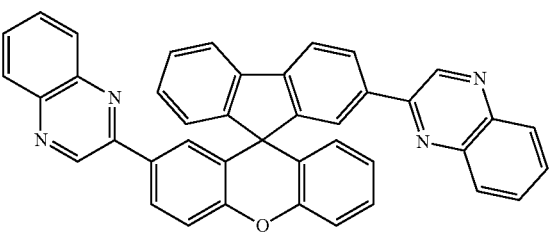

[ET-1-J]

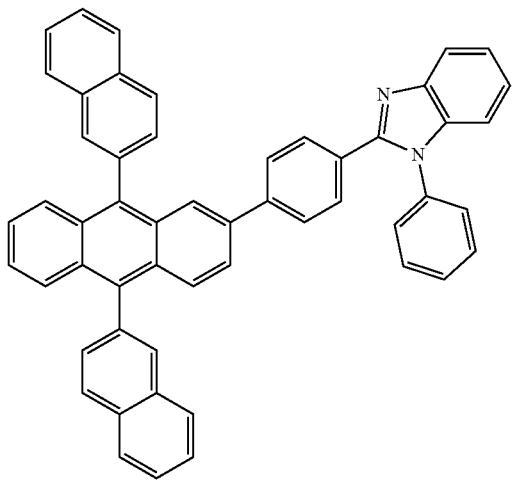

[ET-1-K]

[ET-1-L]

[ET-1-M]

[ET-1-N]

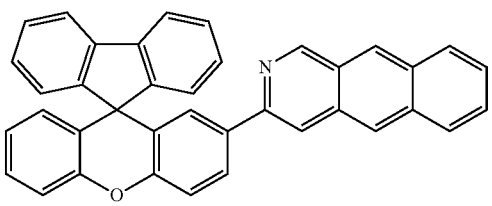

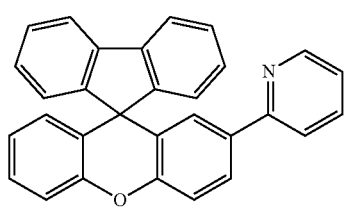

[ET-1-O]

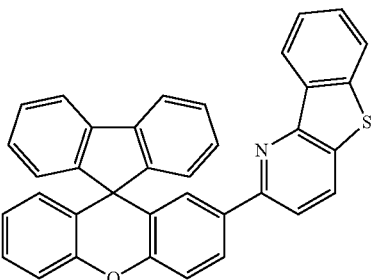

Example 2-2

An organic light emitting device was manufactured in the same manner as in Example 2-1 except that Compound E2 was used instead of Compound E1.

Example 2-3

An organic light emitting device was manufactured in the same manner as in Example 2-1 except that Compound E3 was used instead of Compound E1.

Example 2-4

An organic light emitting device was manufactured in the same manner as in Example 2-1 except that Compound E4 was used instead of Compound E1.

Example 2-5

An organic light emitting device was manufactured in the same manner as in Example 2-1 except that Compound E5 was used instead of Compound E1.

Example 2-6

An organic light emitting device was manufactured in the same manner as in Example 2-1 except that Compound E6 was used instead of Compound E1.

Example 2-7

An organic light emitting device was manufactured in the same manner as in Example 2-1 except that Compound E7 was used instead of Compound E1.

Example 2-8

An organic light emitting device was manufactured in the same manner as in Example 2-1 except that Compound E8 was used instead of Compound E1.

Example 2-11

An organic light emitting device was manufactured in the same manner as in Example 2-1 except that Compound E11 was used instead of Compound E1.

Example 2-12

An organic light emitting device was manufactured in the same manner as in Example 2-1 except that Compound E12 was used instead of Compound E1.

Example 2-13

An organic light emitting device was manufactured in the same manner as in Example 2-1 except that Compound E13 was used instead of Compound E1.

Example 2-14

An organic light emitting device was manufactured in the same manner as in Example 2-1 except that Compound E14 was used instead of Compound E1.

Example 2-15

An organic light emitting device was manufactured in the same manner as in Example 2-1 except that Compound E15 was used instead of Compound E1.

Example 2-16

An organic light emitting device was manufactured in the same manner as in Example 2-1 except that Compound E16 was used instead of Compound E1.

Example 2-17

An organic light emitting device was manufactured in the same manner as in Example 2-1 except that Compound E17 was used instead of Compound E1.

Example 2-18

An organic light emitting device was manufactured in the same manner as in Example 2-1 except that Compound E18 was used instead of Compound E1.

Comparative Example 2-1

An organic light emitting device was manufactured in the same manner as in Example 2-1 except that Compound ET-1-A was used instead of Compound E1.

Comparative Example 2-2

An organic light emitting device was manufactured in the same manner as in Example 2-1 except that Compound ET-1-B was used instead of Compound E1.

Comparative Example 2-3

An organic light emitting device was manufactured in the same manner as in Example 2-1 except that Compound ET-1-C was used instead of Compound E1.

Comparative Example 2-4

An organic light emitting device was manufactured in the same manner as in Example 2-1 except that Compound ET-1-D was used instead of Compound E1.

Comparative Example 2-5

An organic light emitting device was manufactured in the same manner as in Example 2-1 except that Compound ET-1-E was used instead of Compound E1.

Comparative Example 2-6

An organic light emitting device was manufactured in the same manner as in Example 2-1 except that Compound ET-2-F was used instead of Compound E1.

Comparative Example 2-7

An organic light emitting device was manufactured in the same manner as in Example 2-1 except that Compound ET-1-G was used instead of Compound E1.

Comparative Example 2-8

An organic light emitting device was manufactured in the same manner as in Example 2-1 except that Compound ET-1-H was used instead of Compound E1.

Comparative Example 2-9

An organic light emitting device was manufactured in the same manner as in Example 2-1 except that Compound ET-1-I was used instead of Compound E1.

Comparative Example 2-10

An organic light emitting device was manufactured in the same manner as in Example 2-1 except that Compound ET-1-J was used instead of Compound E1.

Comparative Example 2-11

An organic light emitting device was manufactured in the same manner as in Example 2-1 except that Compound ET-1-K was used instead of Compound E1.

Comparative Example 2-12

An organic light emitting device was manufactured in the same manner as in Example 2-1 except that Compound ET-1-L was used instead of Compound E1.

Comparative Example 2-13

An organic light emitting device was manufactured in the same manner as in Example 2-1 except that Compound ET-1-M was used instead of Compound E1.

Comparative Example 2-14

An organic light emitting device was manufactured in the same manner as in Example 2-1 except that Compound ET-1-N was used instead of Compound E1.

Comparative Example 2-15

An organic light emitting device was manufactured in the same manner as in Example 2-1 except that Compound ET-1-O was used instead of Compound E1.

For the organic light emitting devices manufactured using the methods of Examples 2-1 to 2-8 and 2-11 to 2-18, and Comparative Examples 2-1 to 2-15 described above, a driving voltage and light emission efficiency were measured at current density of 10 mA/cm$^2$, and time taken for the luminance decreasing to 90% compared to its initial luminance ($T_{90}$) was measured at current density of 20 mA/cm$^2$. The results are shown in the following Table 2.

TABLE 2

| Compound | | Voltage (V@10 mA/cm$^2$) | Efficiency (cd/A@10 mA/cm$^2$) | Color Coordinate (x, y) | Lifetime (h) $T_{90}$ at 20 mA/cm$^2$ |
|---|---|---|---|---|---|
| Example 2-1 | E1 | 4.30 | 5.09 | (0.142, 0.096) | 159 |
| Example 2-2 | E2 | 4.44 | 5.07 | (0.142, 0.096) | 150 |
| Example 2-3 | E3 | 4.32 | 5.00 | (0.142, 0.096) | 149 |
| Example 2-4 | E4 | 4.50 | 5.08 | (0.142, 0.097) | 142 |
| Example 2-5 | E5 | 4.34 | 4.98 | (0.142, 0.097) | 130 |
| Example 2-6 | E6 | 4.36 | 4.96 | (0.142, 0.096) | 132 |
| Example 2-7 | E7 | 4.38 | 5.01 | (0.142, 0.097) | 166 |
| Example 2-8 | E8 | 4.30 | 5.20 | (0.142, 0.099) | 211 |
| Example 2-11 | E11 | 4.35 | 5.01 | (0.142, 0.097) | 197 |
| Example 2-12 | E12 | 4.32 | 5.10 | (0.142, 0.096) | 185 |
| Example 2-13 | E13 | 4.28 | 5.22 | (0.142, 0.097) | 200 |
| Example 2-14 | E14 | 4.46 | 5.02 | (0.142, 0.096) | 151 |
| Example 2-15 | E15 | 4.34 | 4.92 | (0.142, 0.097) | 147 |
| Example 2-16 | E16 | 4.37 | 5.15 | (0.142, 0.097) | 241 |
| Example 2-17 | E17 | 4.33 | 4.91 | (0.142, 0.097) | 149 |
| Example 2-18 | E18 | 4.29 | 5.10 | (0.142, 0.096) | 177 |
| Comparative Example 2-1 | ET-1-A | 4.80 | 3.89 | (0.142, 0.098) | 80 |
| Comparative Example 2-2 | ET-1-B | 4.87 | 4.00 | (0.142, 0.102) | 76 |
| Comparative Example 2-3 | ET-1-C | 4.98 | 3.81 | (0.142, 0.096) | 82 |
| Comparative Example 2-4 | ET-1-D | 4.73 | 4.07 | (0.142, 0.096) | 57 |
| Comparative Example 2-5 | ET-1-E | 5.02 | 3.58 | (0.142, 0.096) | 69 |
| Comparative Example 2-6 | ET-2-F | 5.11 | 3.44 | (0.142, 0.096) | 72 |
| Comparative Example 2-7 | ET-1-G | 5.42 | 3.07 | (0.142, 0.096) | 54 |
| Comparative Example 2-8 | ET-1-H | 5.46 | 3.11 | (0.142, 0.096) | 50 |
| Comparative Example 2-9 | ET-1-I | 5.57 | 3.06 | (0.142, 0.096) | 55 |
| Comparative Example 2-10 | ET-1-J | 5.47 | 3.99 | (0.142, 0.096) | 78 |
| Comparative Example 2-11 | ET-1-K | 5.00 | 4.10 | (0.142, 0.097) | 95 |
| Comparative Example 2-12 | ET-1-L | 5.40 | 3.21 | (0.142, 0.096) | 40 |
| Comparative Example 2-13 | ET-1-M | 5.42 | 2.88 | (0.142, 0.097) | 44 |
| Comparative Example 2-14 | ET-1-N | 5.05 | 3.00 | (0.142, 0.097) | 37 |
| Comparative Example 2-15 | ET-1-O | 5.84 | 1.85 | (0.142, 0.097) | 41 |

From the results of Table 2, it was identified that the heterocyclic compound represented by Chemical Formula 1 according to one embodiment of the present specification was able to be used in an electron control layer of an organic light emitting device.

Specifically, when comparing Examples 2-1 to 2-8 and 2-11 to 2-18 with Comparative Examples 2-1, 2-2, 2-3, 2-5, 2-7, 2-8 and 2-9, it was identified that the compound in which only one heteroaryl group substitutes in the spiro fluorene xanthen skeleton as in Chemical Formula 1 had excellent properties in terms of driving voltage, efficiency and lifetime in an organic light emitting device compared to the compound having two or more substituents in the spiro fluorene xanthen skeleton.

When referring to FIG. 3 and FIG. 4 illustrating 3D structures of Compounds E3 and E6 according to one embodiment of the present specification, it was identified that the molecules of the compounds had a horizontal structure, and when referring to FIG. 5 and FIG. 6 illustrating 3D structures of Compounds ET-1-E and ET-1-I, the A axis and the B axis were almost perpendicular to each other in each compound identifying that the molecule was very out of a horizontal structure.

As a result, when comparing FIG. 3 and FIG. 4 illustrating 3D structures of Compounds E3 and E6 according to one embodiment of the present specification and FIG. 5 and FIG. 6 illustrating 3D structures of Compounds ET-1-E and ET-1-I, it was seen that the heterocyclic compound represented by Chemical Formula 1 according to one embodiment of the present specification had a more horizontal structure due to a difference in orientation in the molecular 3D structure. Accordingly, the compound in which only one heteroaryl group substitutes in the spiro fluorene xanthen skeleton as in Chemical Formula 1 of Examples 2-1 to 2-8 and 2-11 to 2-18 had a strong tendency toward a horizontal structure of the molecule compared to the compound having two or more substituents in the spiro fluorene xanthen resulting in an increase in the electron mobility, and effects of low driving voltage, high efficiency and long lifetime are obtained in an organic light emitting device.

In addition, when comparing Examples 2-1 to 2-8 and 2-11 to 2-18 with Comparative Examples 2-4 and 2-6, it was identified that the structure of Chemical Formula 1 comprising spiro fluorene xanthen exhibited excellent properties in an organic light emitting device compared to the structure comprising a spiro fluorene group.

In addition, when comparing Example 2-1 to 2-8 and 2-11 to 2-18 with Comparative Example 2-11 to 2-15, it was identified that the structure of Chemical Formula 1 in which Ar1 comprises two or more Ns exhibited effects of low driving voltage, high efficiency and long lifetime in an organic light emitting device compared to the structure comprising one N.

The heterocyclic compound represented by Chemical Formula 1 according to one embodiment of the present specification is capable of having excellent properties by having excellent thermal stability, a deep HOMO level of 6.0 eV or higher, high triplet energy (ET) and hole stability.

In one embodiment of the present specification, by using the heterocyclic compound represented by Chemical Formula 1 in an electron control layer, low driving voltage and high efficiency are obtained, and device stability may be enhanced by hole stability of the compound.

Hereinbefore, preferred embodiments of the present disclosure have been described, however, the present disclosure is not limited thereto, and various modifications may be made within the scope of the claims and detailed descriptions of the disclosure, and these also belong to the category of the disclosure.

The invention claimed is:
1. A heterocyclic compound represented by the following Chemical Formula 1:

[Chemical Formula 1]

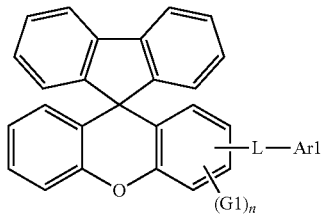

wherein, in Chemical Formula 1,

G1 is hydrogen; deuterium; a nitrile group; a nitro group; a hydroxyl group; a carbonyl group;

an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group;

L is a direct bond; or a substituted or unsubstituted arylene group;

Ar1 is any one of the following Chemical Formulae 2-A to 2-E:

[Chemical Formula 2-A]

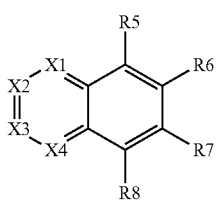

[Chemical Formula 2-B]

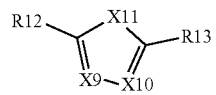

[Chemical Formula 2-C]

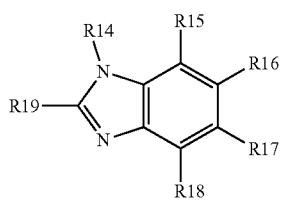

[Chemical Formula 2-D]

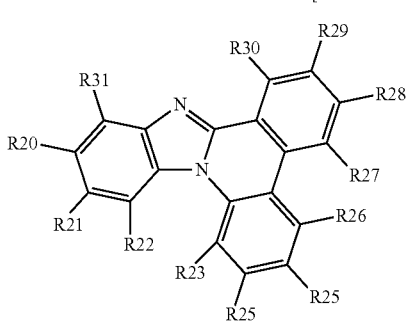

[Chemical Formula 2-E]

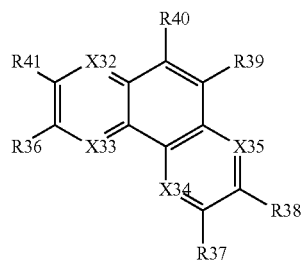

wherein, in Chemical Formula 2-A to Chemical Formula 2-E,

X1 is N or CR1, X2 is N or CR2, X3 is N or CR3, X4 is N or CR4, and at least two of X1 to X4 are N;

X9 is N or CR9, X10 is N or CR10, and X11 is O; S; or NR11;

and when X11 is NR11, at least one of X9 and X10 is N, and when X11 is O or S, X9 and X10 are each N;

X32 is N or CR32, X33 is N or CR33, X34 is N or CR34, X35 is N or CR35, and at least two of X32 to X35 are N;

any one of R1 to R8, any one of R9 to R13, any one of R14 to R19, any one of R20 to R31 or any one of R32 to R41 is a site bonding to L of Chemical Formula 1;

the rest of R1 to R13 and R20 to R41 other than the site bonding to L of Chemical Formula 1 are the same as or different from each other, and each independently hydrogen; deuterium; a nitrile group; a nitro group; a hydroxyl group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group; and the rest of R14 to R19 other than the site bonding to L of Chemical Formula 1 are the same as or different from each other, and each independently hydrogen; a phenyl group unsubstituted or substituted with a nitrile group; a naphthyl group unsubstituted or substituted with a nitrile group; or a biphenyl group unsubstituted or substituted with a nitrile group; and n is an integer of 0 to 3, and when n is 2 or greater, G1s are the same as or different from each other.

2. The heterocyclic compound of claim 1, wherein L is a direct bond; a substituted or unsubstituted phenylene group; a substituted or unsubstituted biphenylene group; a substituted or unsubstituted naphthalene group; a substituted or unsubstituted terphenylene group; a substituted or unsubstituted quaterphenylene group; a substituted or unsubstituted anthracenylene group; a substituted or unsubstituted phenanthrenylene group; a substituted or unsubstituted triphenylenylene group; a substituted or unsubstituted pyrenylene group; a substituted or unsubstituted fluorenylene group; or a substituted or unsubstituted spiro cyclopentane fluorenylene group.

3. The heterocyclic compound of claim 1, wherein Chemical Formula 2-A is represented by any one of the following Chemical Formulae 3-A to 3-D:

[Chemical Formula 3-A]

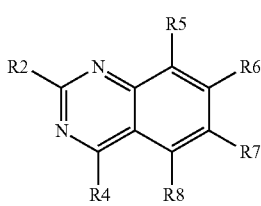

[Chemical Formula 3-B]

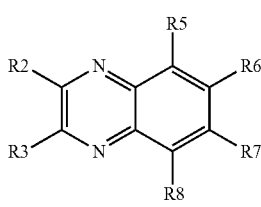

[Chemical Formula 3-C]

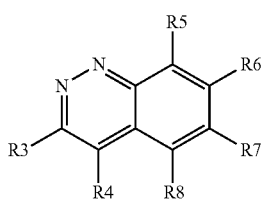

[Chemical Formula 3-D]

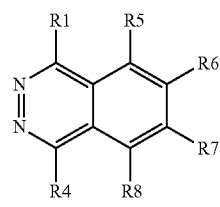

wherein,
in Chemical Formula 3-A, any one of R2 and R4 to R8 is a site bonding to L of Chemical Formula 1;
in Chemical Formula 3-B, any one of R2, R3 and R5 to R8 is a site bonding to L of Chemical Formula 1;
in Chemical Formula 3-C, any one of R3 to R8 is a site bonding to L of Chemical Formula 1;
in Chemical Formula 3-D, any one of R1 and R4 to R8 is a site bonding to L of Chemical Formula 1; and
the rest of R1 to R8 other than the site bonding to L of Chemical Formula 1 are the same as or different from each other, and each independently hydrogen; deuterium; a nitrile group; a nitro group; a hydroxyl group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group.

4. The heterocyclic compound of claim 1, wherein Chemical Formula 2-B is represented by any one of the following Chemical Formulae 4-A to 4-D:

[Chemical Formula 4-A]

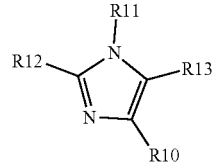

[Chemical Formula 4-B]

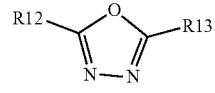

[Chemical Formula 4-C]

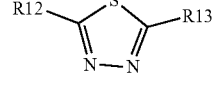

[Chemical Formula 4-D]

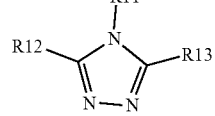

wherein,
in Chemical Formula 4-A, any one of R10 to R13 is a site bonding to L of Chemical Formula 1;
in Chemical Formulae 4-B and 4-C, R12 or R13 is a site bonding to L of Chemical Formula 1;
in Chemical Formula 4-D, any one of R11 to R13 is a site bonding to L of Chemical Formula 1; and
the rest of R10 to R13 other than the site bonding to L of Chemical Formula 1 are the same as or different from each other, and each independently hydrogen; deuterium; a nitrile group; a nitro group; a hydroxyl group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group.

5. The heterocyclic compound of claim 1, wherein Chemical Formula 2-E is represented by any one of the following Chemical Formulae 5-A to 5-G:

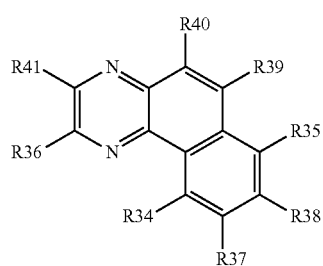

[Chemical Formula 5-A]

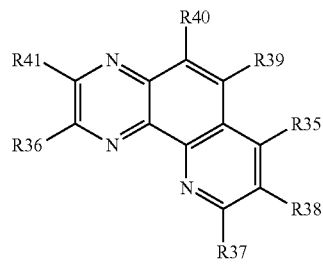

[Chemical Formula 5-B]

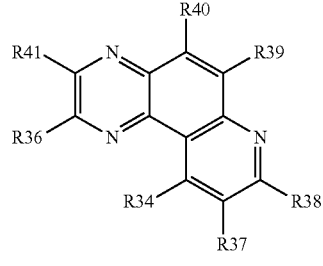

[Chemical Formula 5-C]

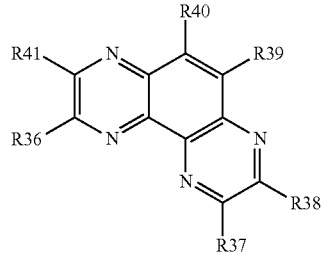

[Chemical Formula 5-D]

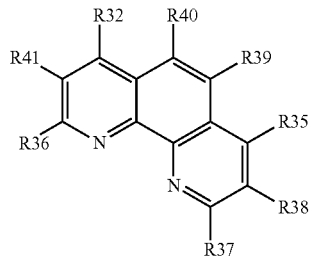

[Chemical Formula 5-E]

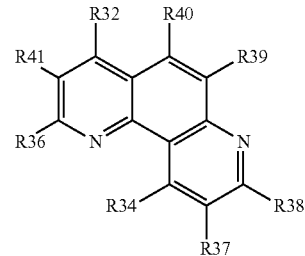

[Chemical Formula 5-F]

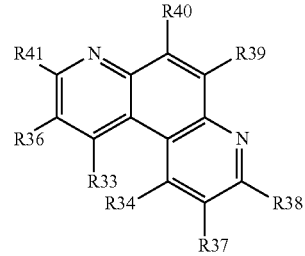

[Chemical Formula 5-G]

wherein,
in Chemical Formula 5-A, any one of R34 to R41 is a site bonding to L of Chemical Formula 1;
in Chemical Formula 5-B, any one of R35 to R41 is a site bonding to L of Chemical Formula 1;
in Chemical Formula 5-C, any one of R34 and R36 to R41 is a site bonding to L of Chemical Formula 1;
in Chemical Formula 5-D, any one of R36 to R41 is a site bonding to L of Chemical Formula 1;
in Chemical Formula 5-E, any one of R32 and R35 to R41 is a site bonding to L of Chemical Formula 1;
in Chemical Formula 5-F, any one of R32, R34 and R36 to R41 is a site bonding to L of Chemical Formula 1;
in Chemical Formula 5-G, any one of R33, R34 and R36 to R41 is a site bonding to L of Chemical Formula 1; and
the rest of R32 to R41 other than the site bonding to L of Chemical Formula 1 are the same as or different from each other, and each independently hydrogen; deuterium; a nitrile group; a nitro group; a hydroxyl group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group.

6. The heterocyclic compound of claim 1, wherein Chemical Formula 1 is represented by any one of the following Chemical Formulae 1-1 to 1-3:

[Chemical Formula 1-1]

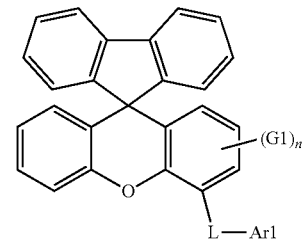

[Chemical Formula 1-2]

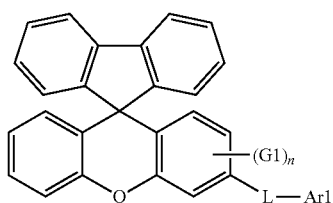

[Chemical Formula 1-3]

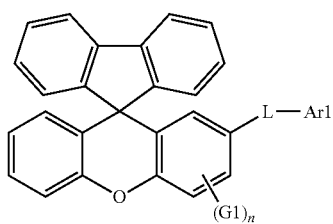

wherein, in Chemical Formulae 1-1 to 1-3,
L, Ar1, G1 and n have the same definitions as in Chemical Formula 1.

7. The heterocyclic compound of claim 1, wherein the rest of R1 to R8 other than the site bonding to L of Chemical Formula 1 are the same as or different from each other, and each independently hydrogen; a phenyl group unsubstituted or substituted with a nitrile group; a naphthyl group unsubstituted or substituted with a nitrile group; or a biphenyl group unsubstituted or substituted with a nitrile group.

8. The heterocyclic compound of claim 1, wherein the rest of R9 to R13 other than the site bonding to L of Chemical Formula 1 are the same as or different from each other, and each independently hydrogen; a phenyl group unsubstituted or substituted with a nitrile group; a naphthyl group unsubstituted or substituted with a nitrile group; or a biphenyl group unsubstituted or substituted with a nitrile group.

9. The heterocyclic compound of claim 1, wherein the rest of R20 to R31 other than the site bonding to L of Chemical Formula 1 are the same as or different from each other, and each independently hydrogen; a phenyl group unsubstituted or substituted with a nitrile group; a naphthyl group unsubstituted or substituted with a nitrile group; or a biphenyl group unsubstituted or substituted with a nitrile group.

10. The heterocyclic compound of claim 1, wherein the rest of R32 to R41 other than the site bonding to L of Chemical Formula 1 are the same as or different from each other, and each independently hydrogen; a phenyl group unsubstituted or substituted with a nitrile group; a naphthyl group unsubstituted or substituted with a nitrile group; or a biphenyl group unsubstituted or substituted with a nitrile group.

11. The heterocyclic compound of claim 1, wherein G1 is hydrogen or deuterium.

12. The heterocyclic compound of claim 1, wherein the heterocyclic compound represented by Chemical Formula 1 is any one selected from among the following heterocyclic compounds:

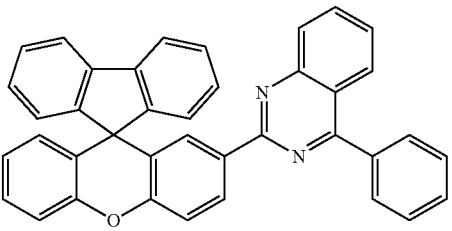

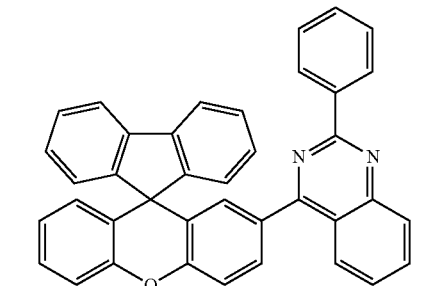

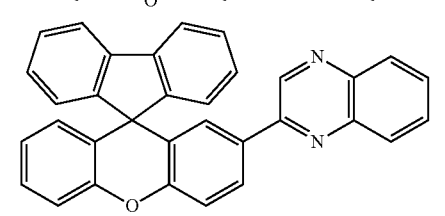

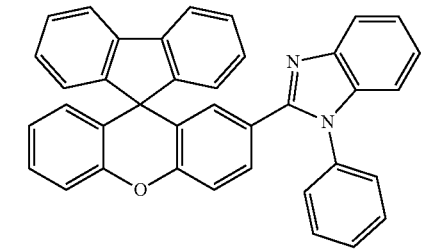

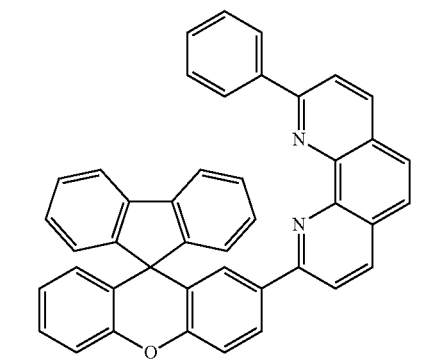

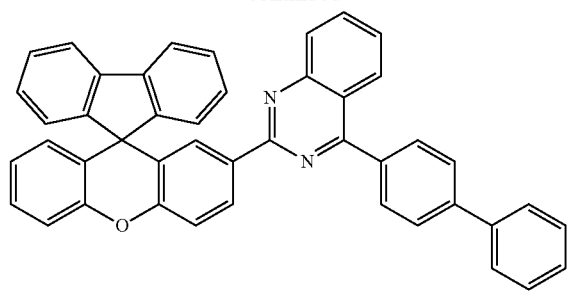
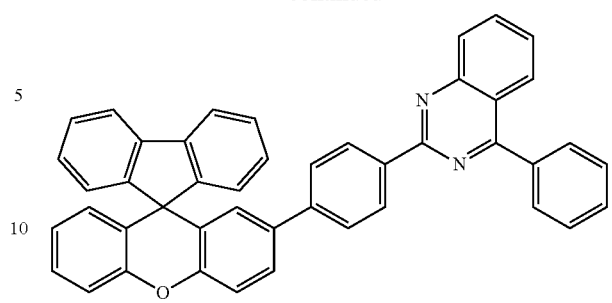
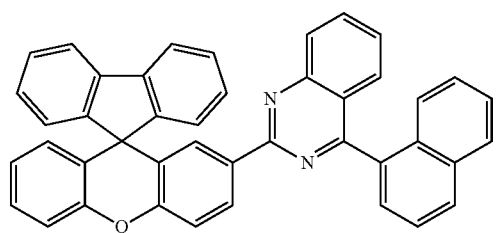
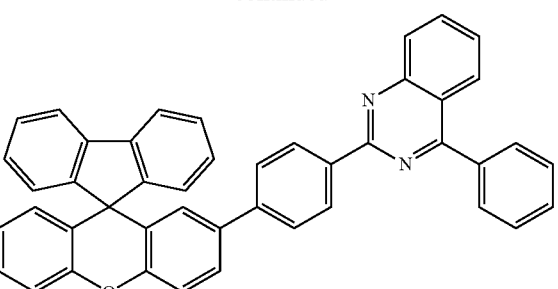
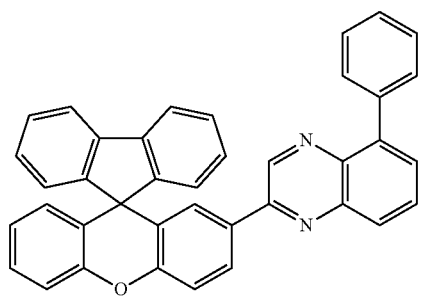
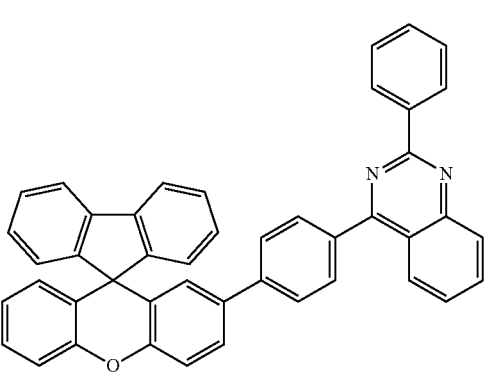
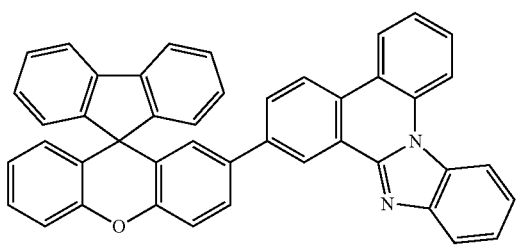
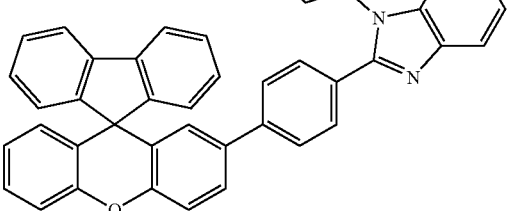
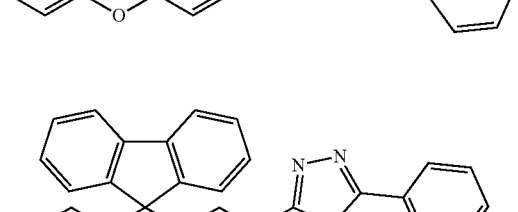
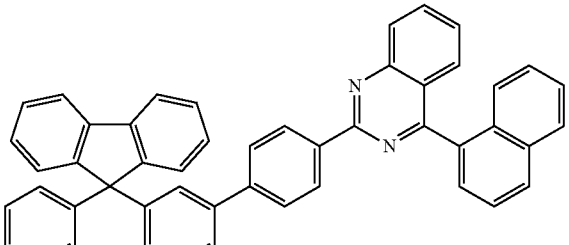
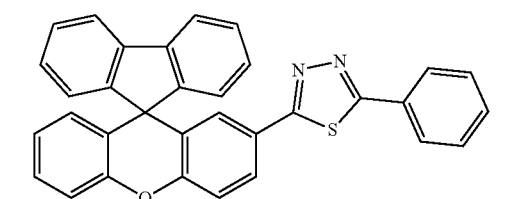
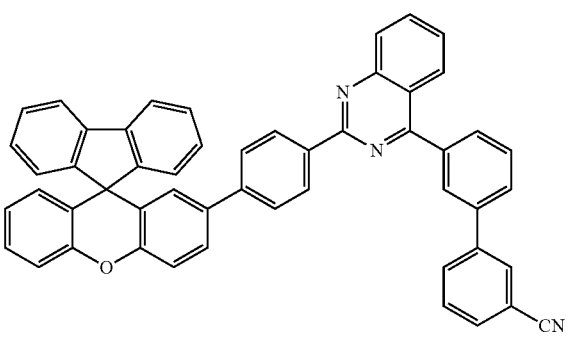

-continued
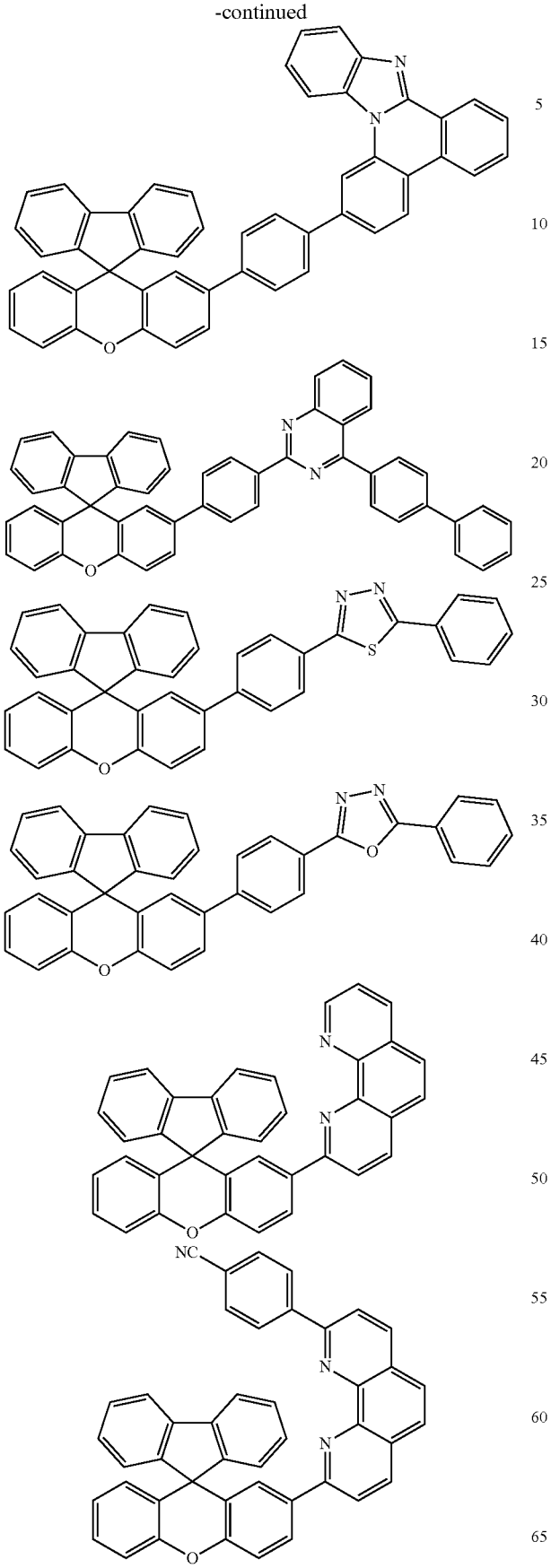
-continued
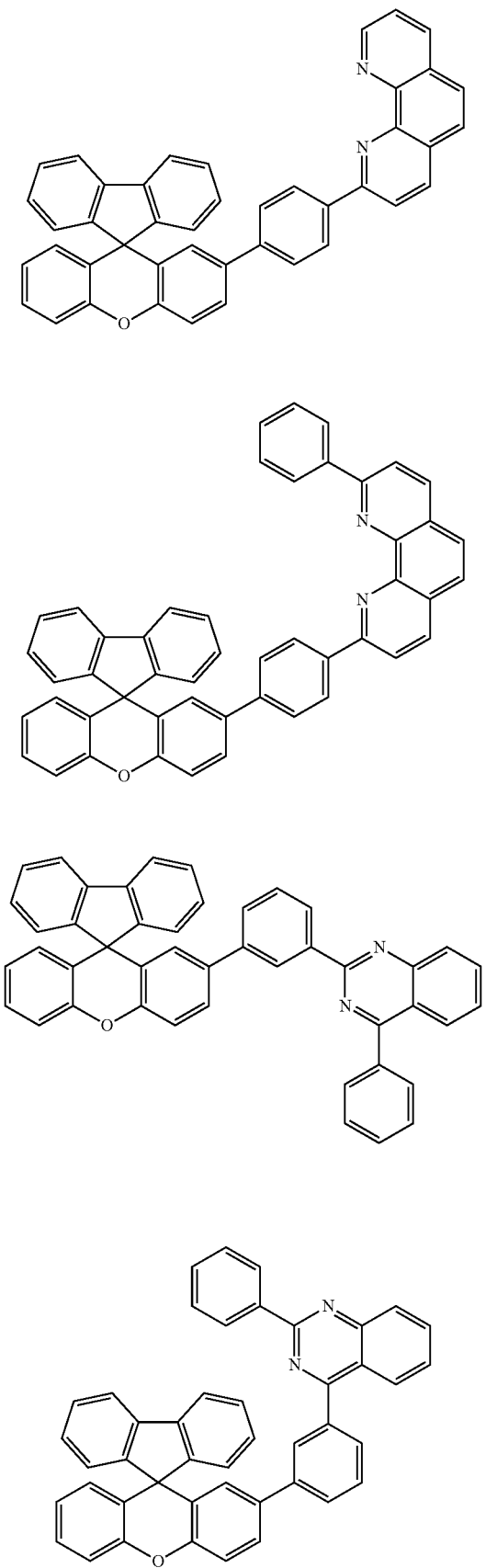

101
-continued
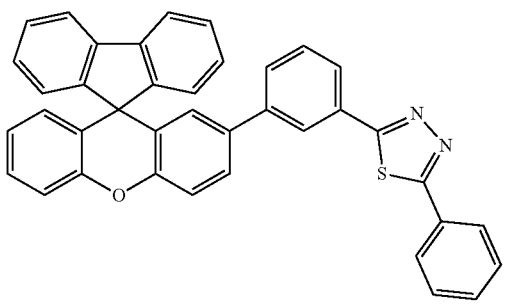
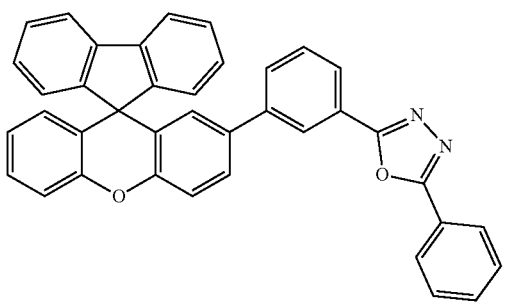
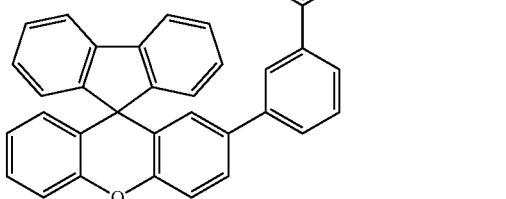
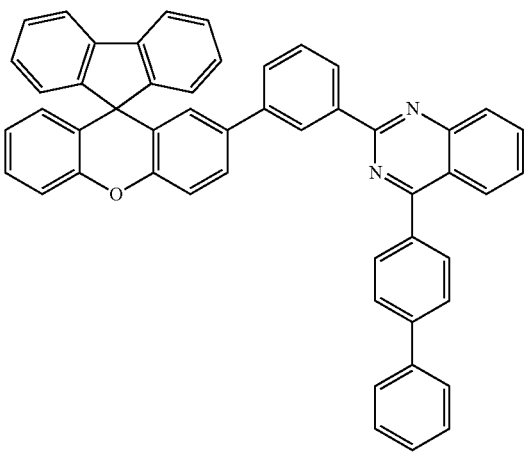
102
-continued
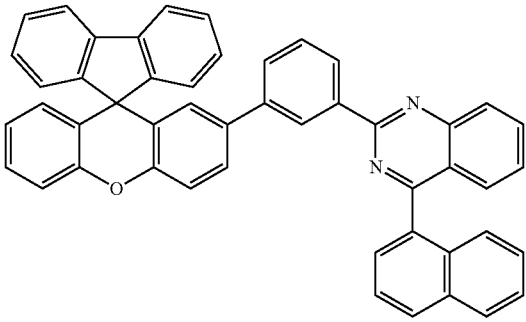
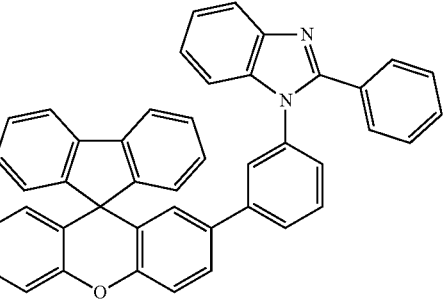
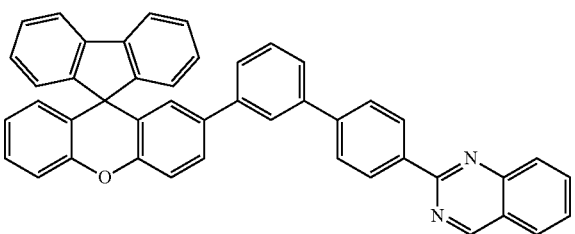
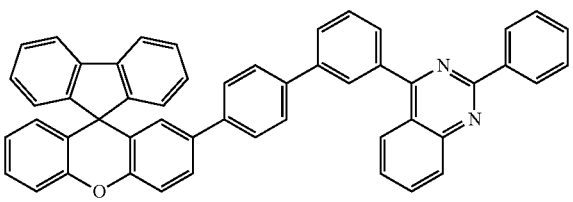
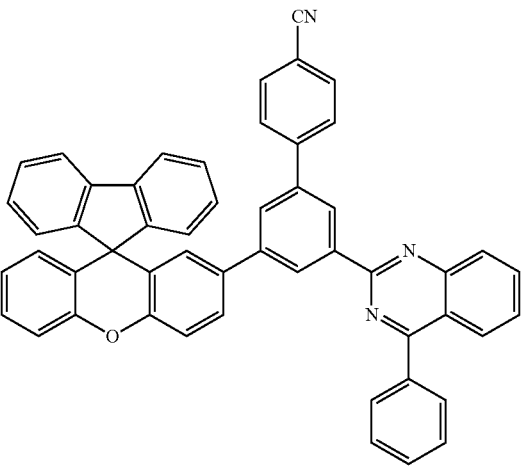

103
-continued
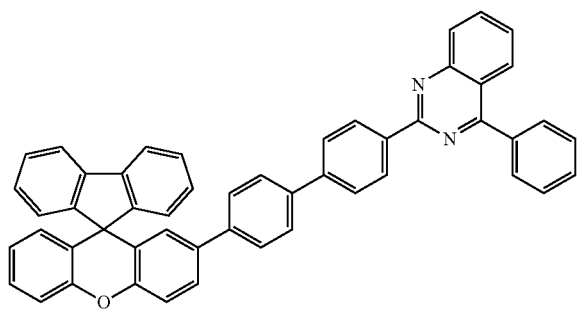
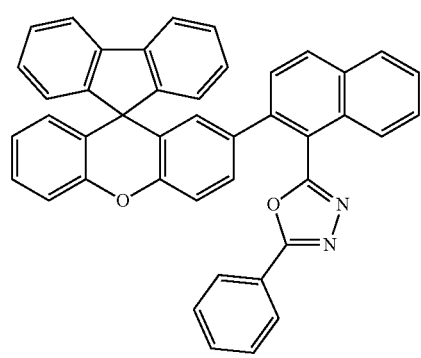
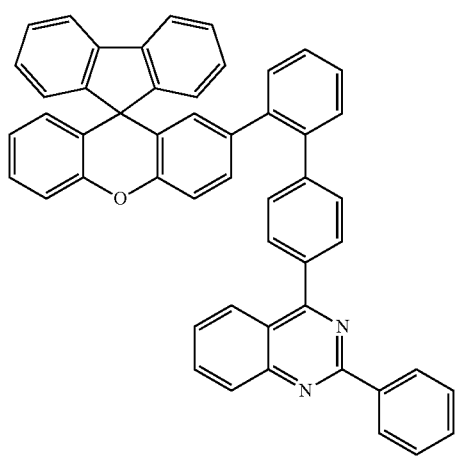
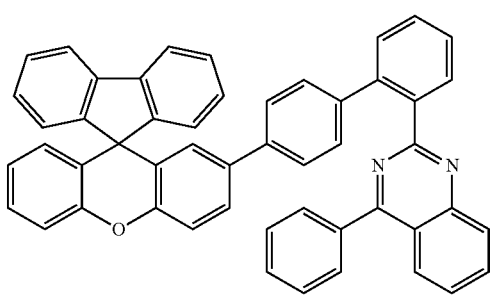
104
-continued
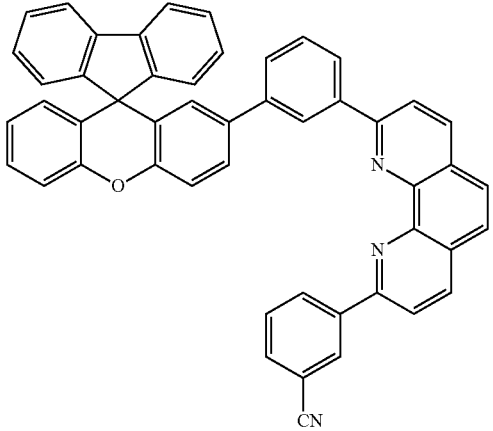
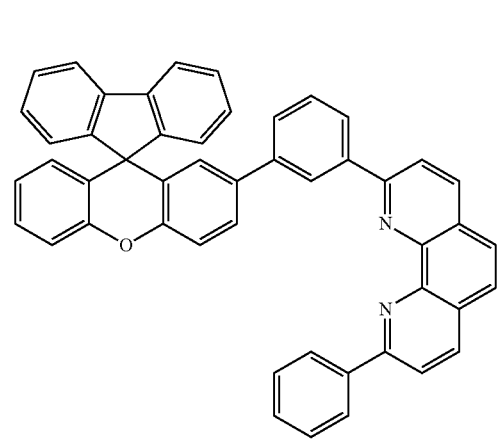
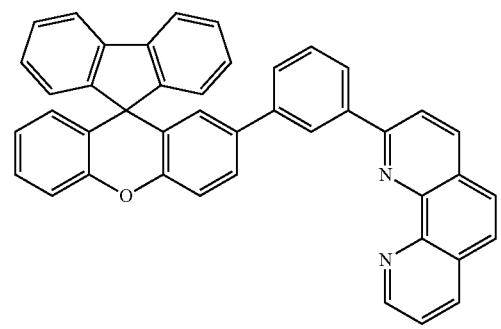
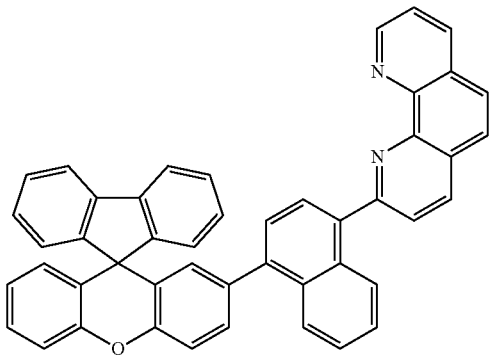

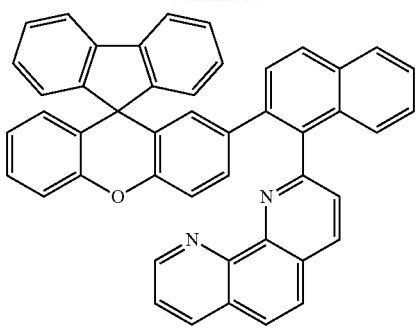
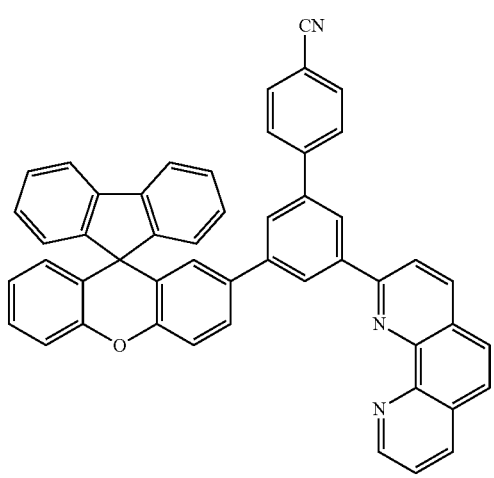
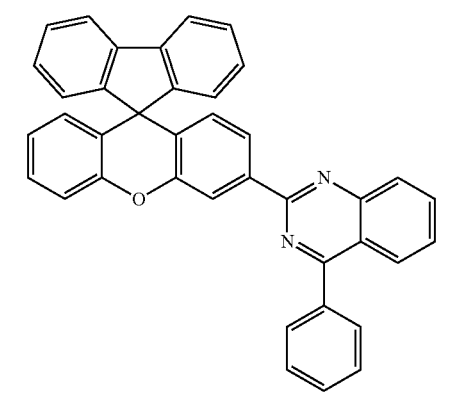
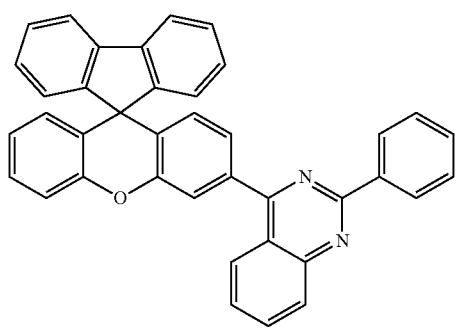
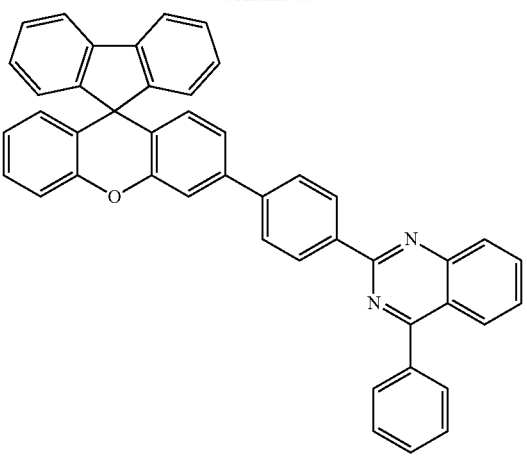
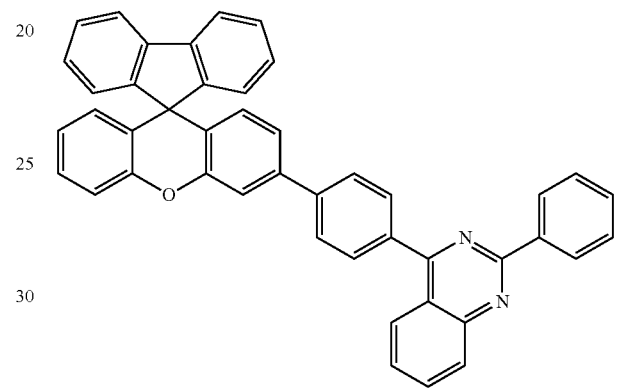
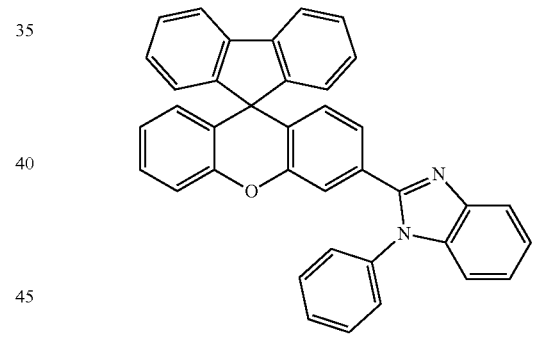
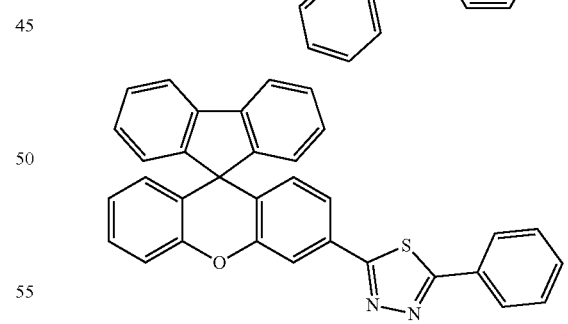
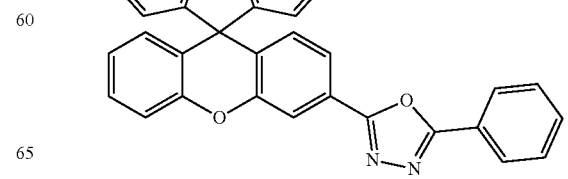

107
-continued
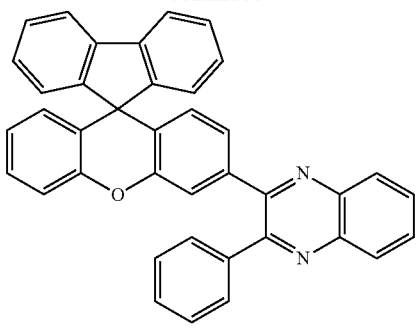
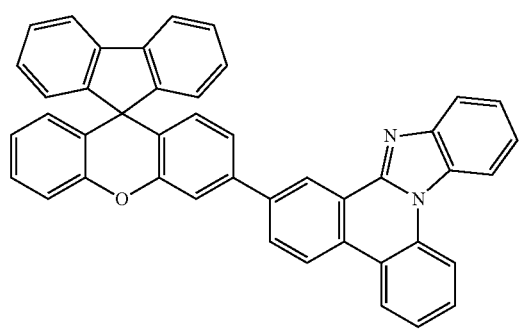
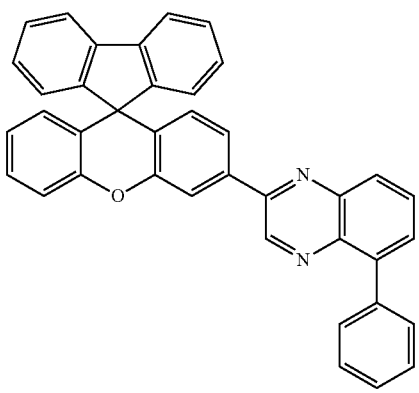
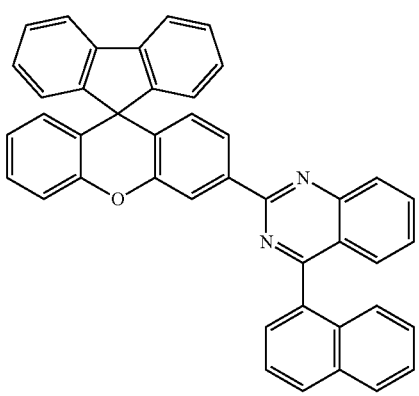
108
-continued
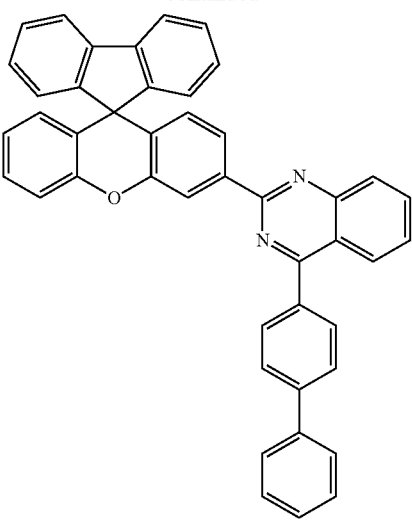
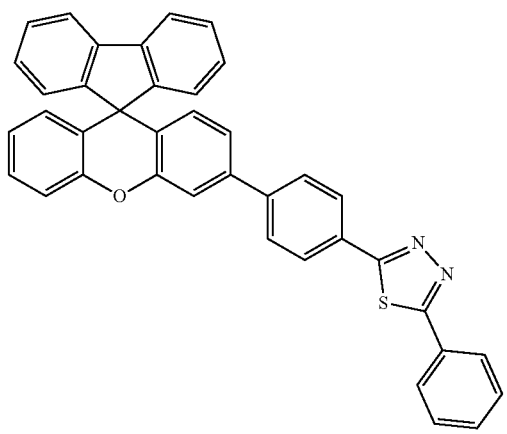
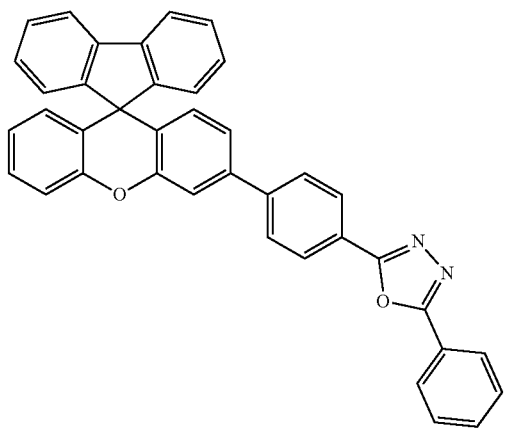

109
-continued
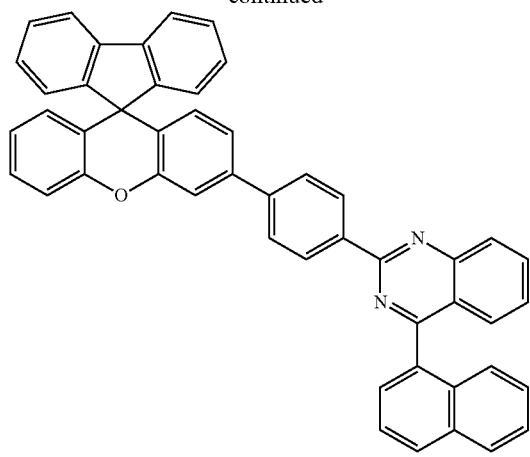
110
-continued
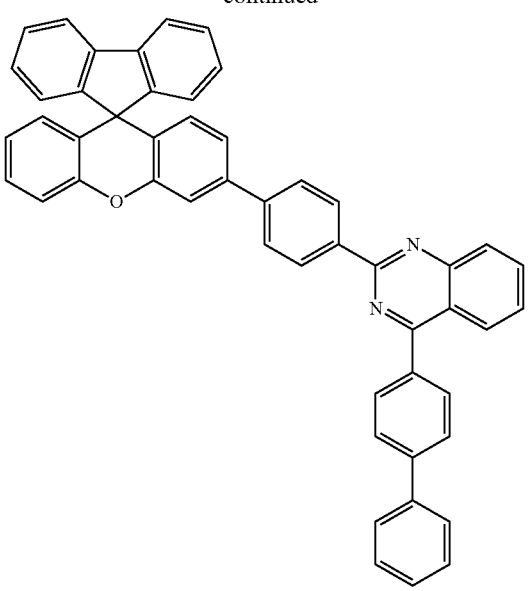
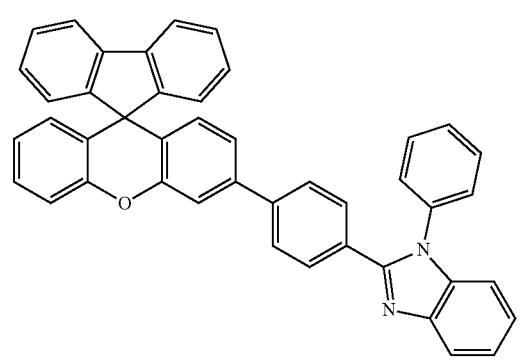
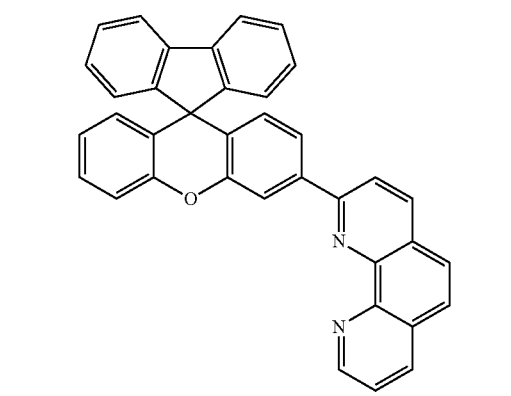
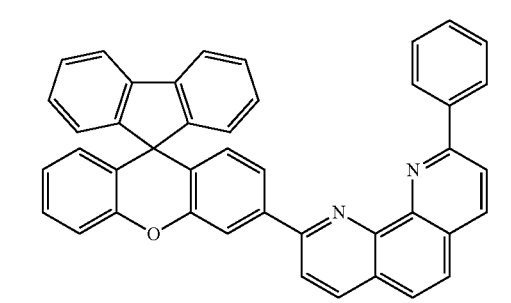

111
-continued
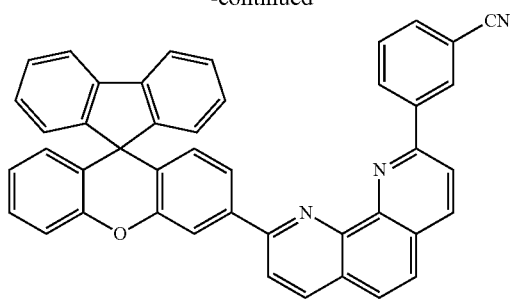
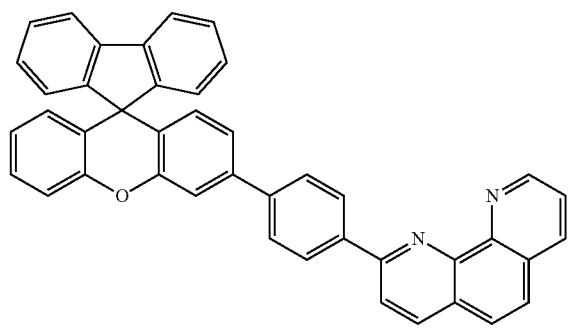
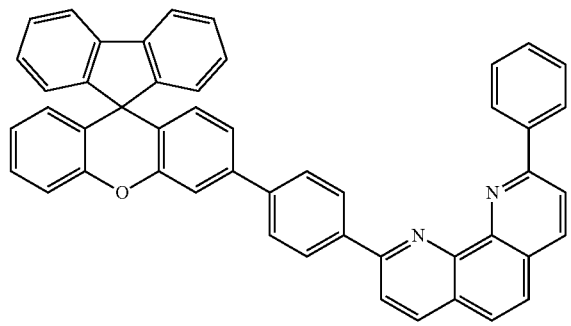
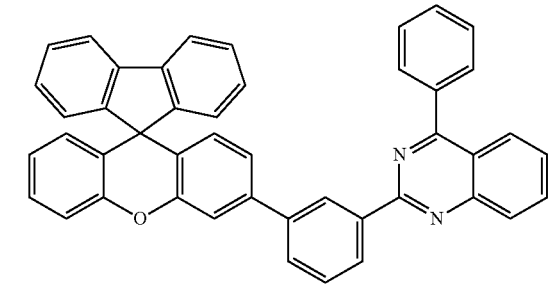
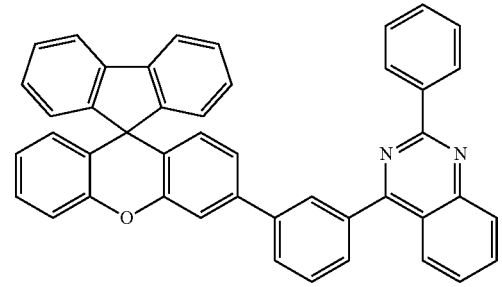
112
-continued
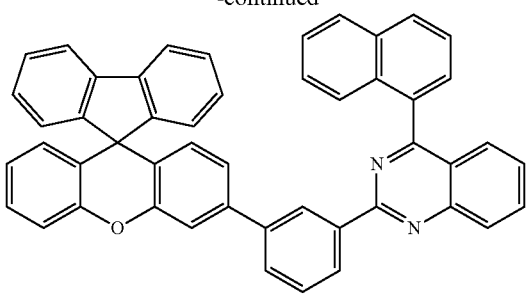
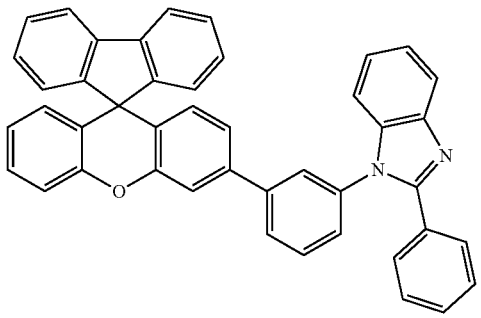
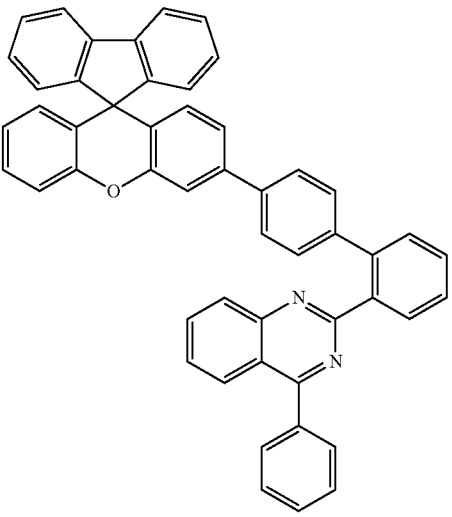
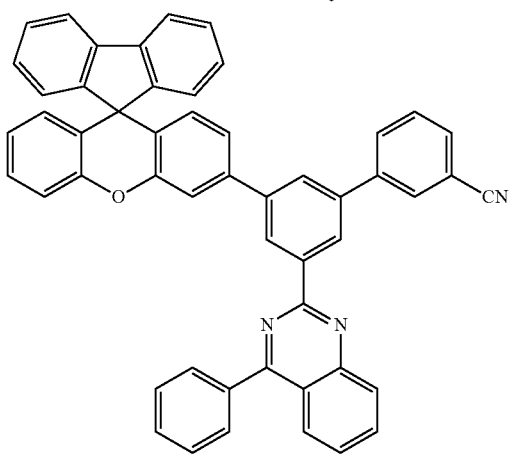

113
-continued
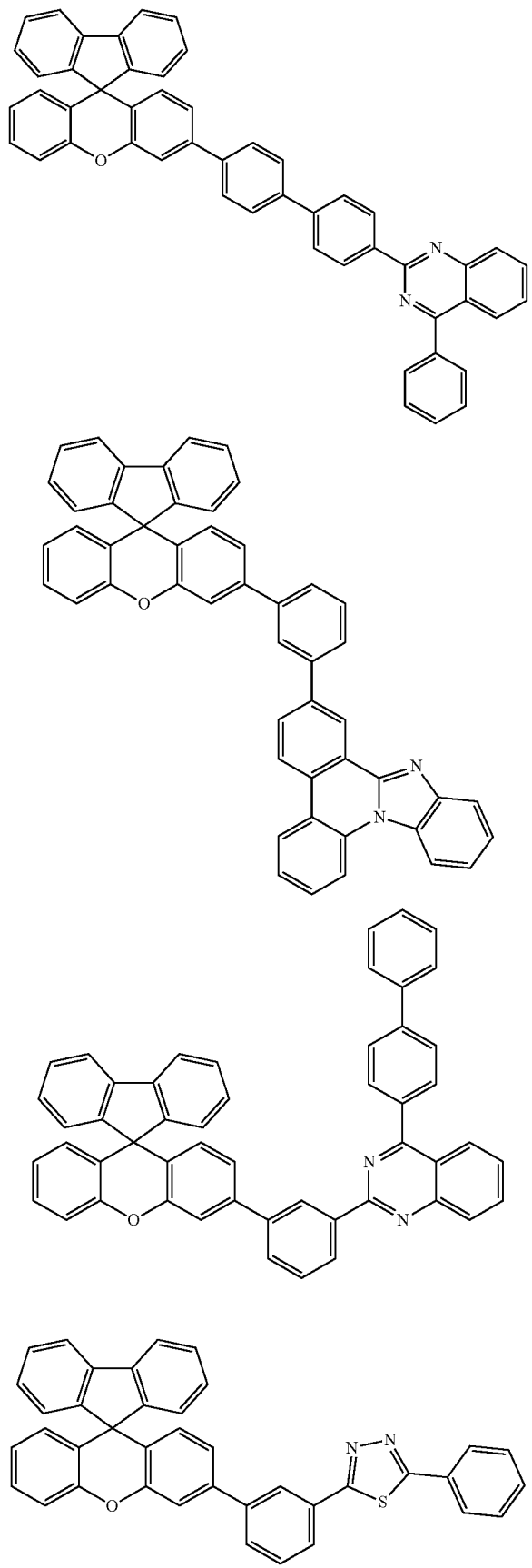
114
-continued
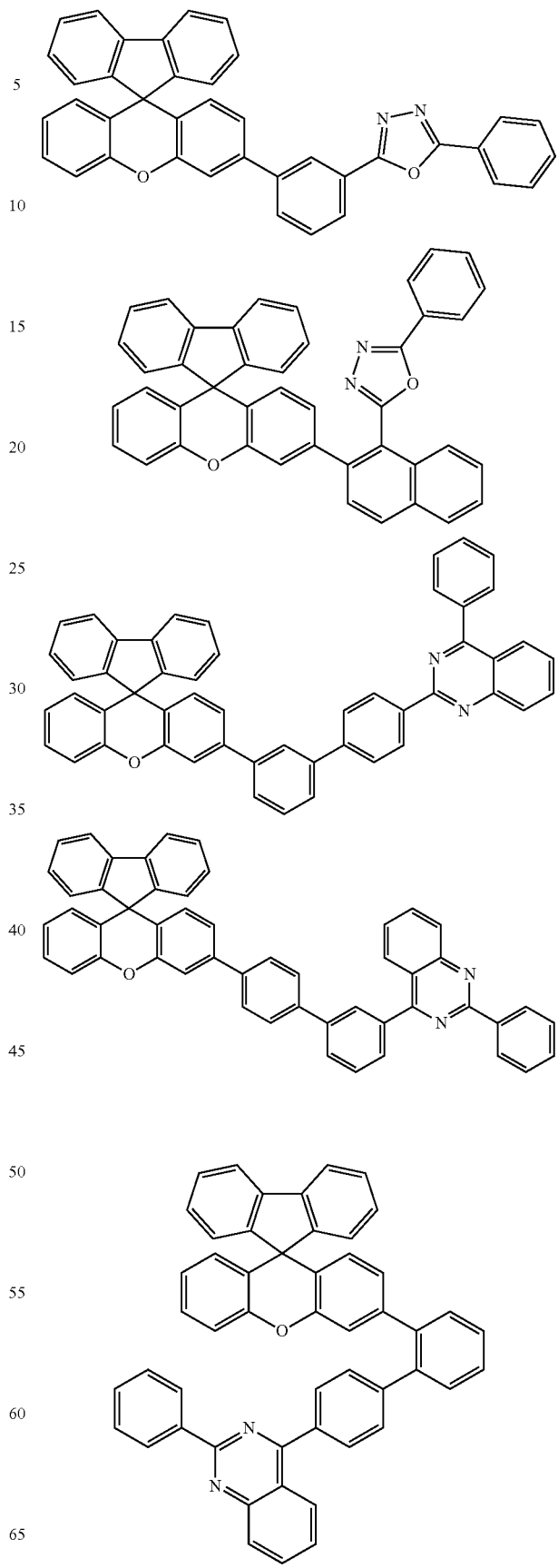

115
-continued
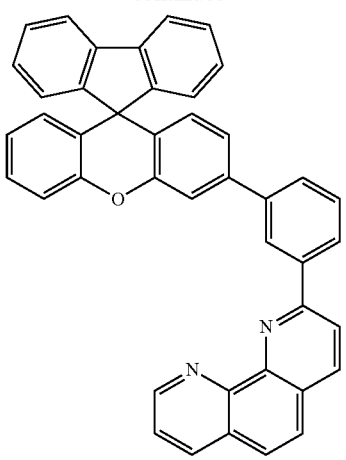
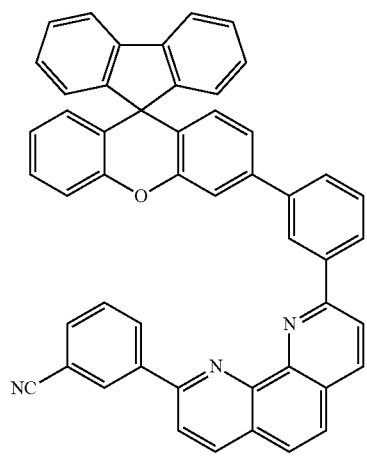
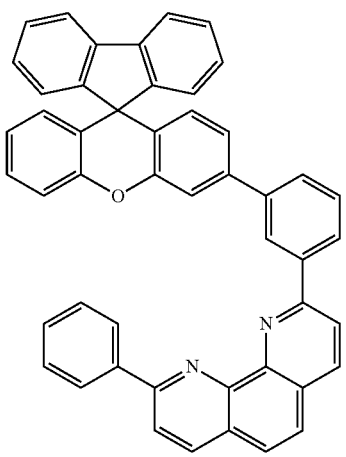
116
-continued
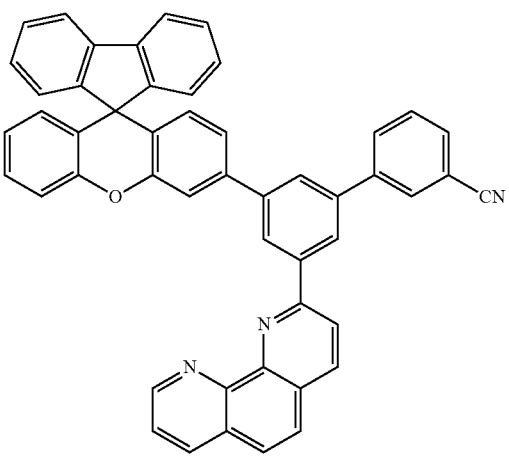
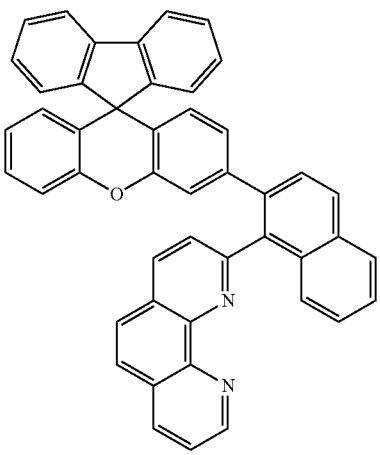
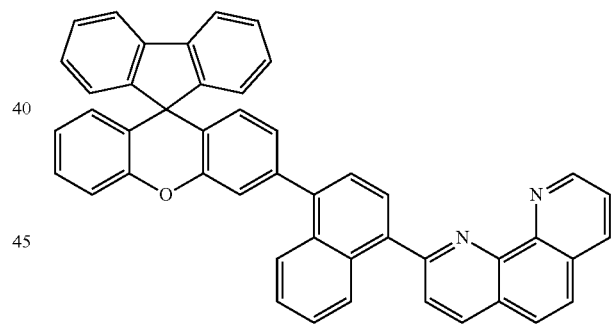
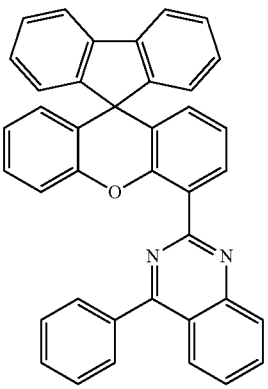

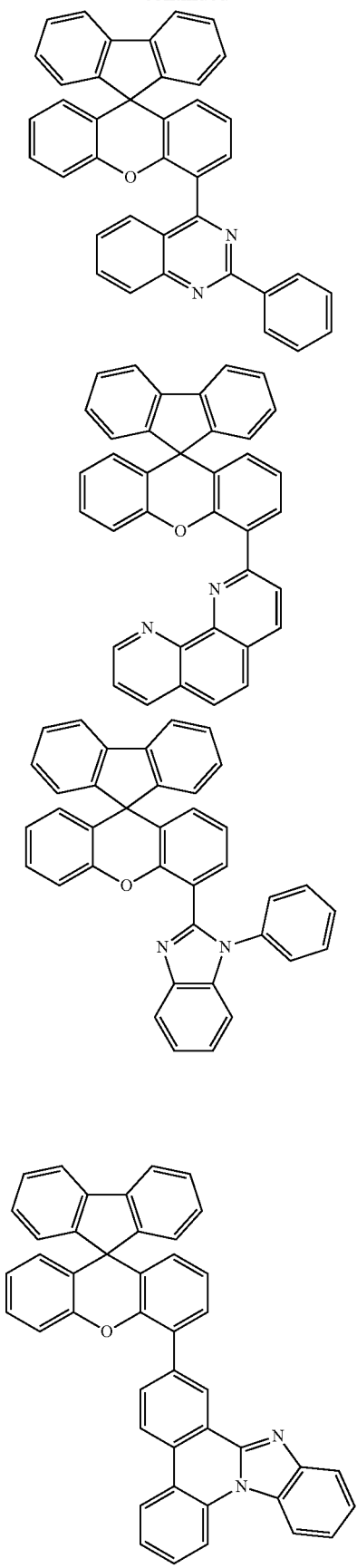
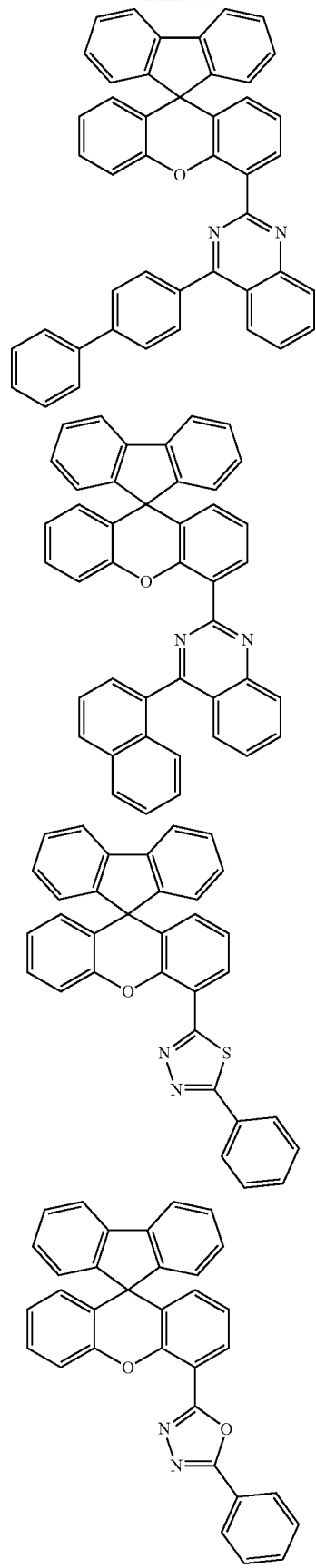

| 119 | 120 |
|---|---|
| -continued | -continued |
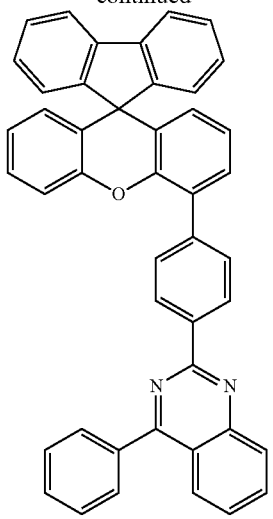
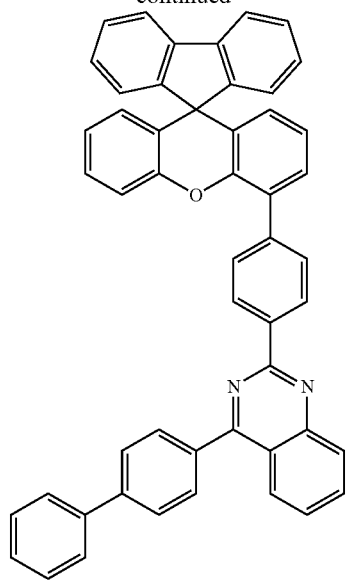
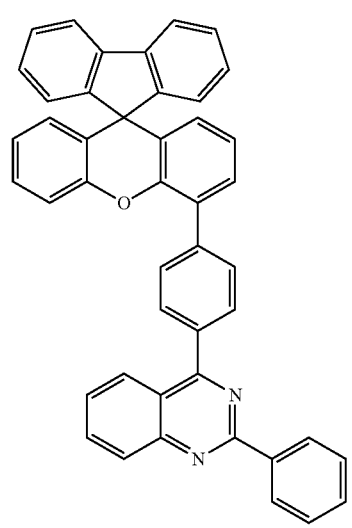
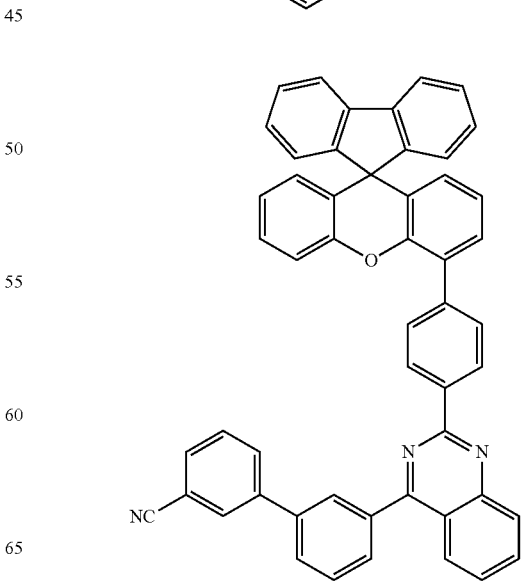
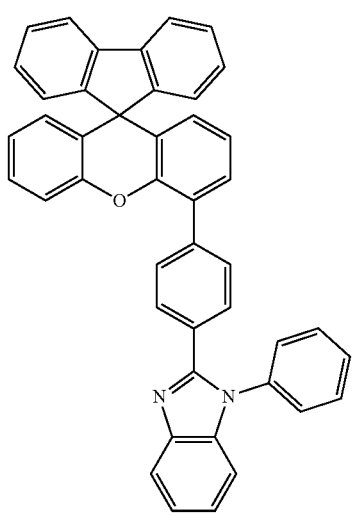

121
-continued
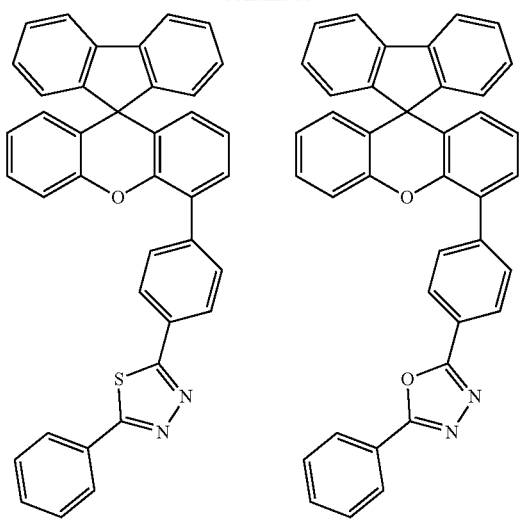
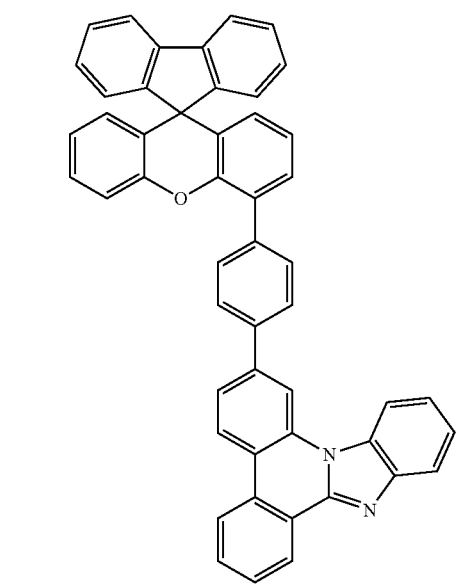
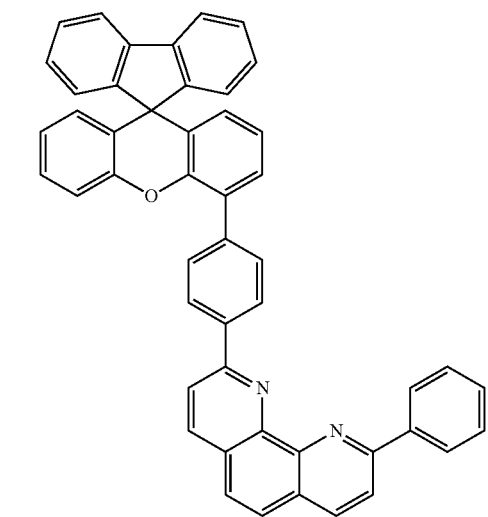
122
-continued
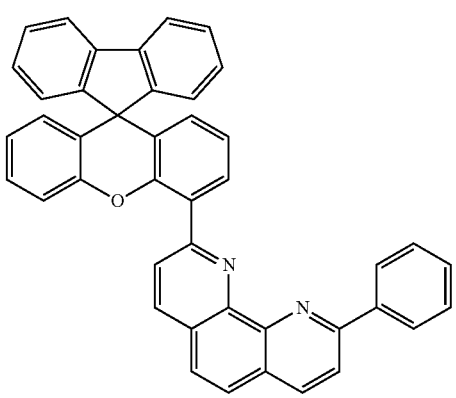
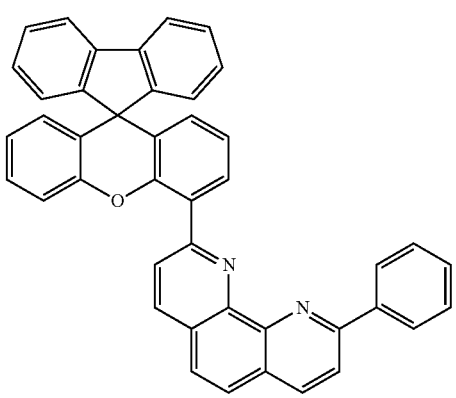
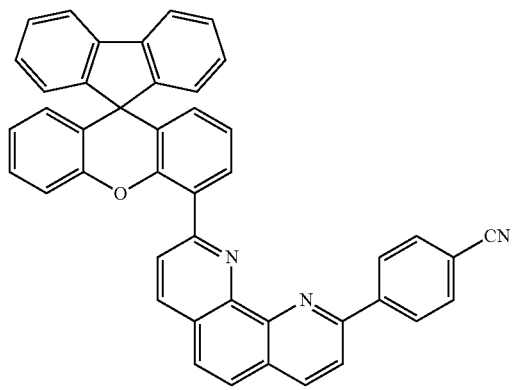

123
-continued
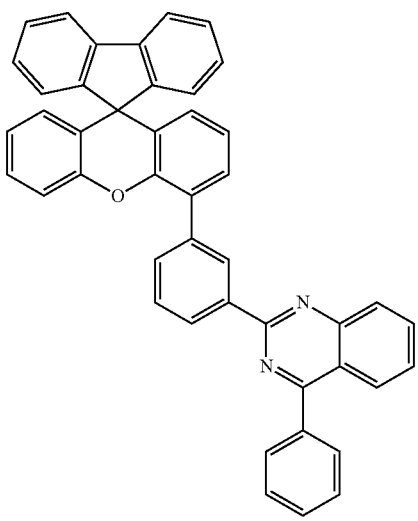
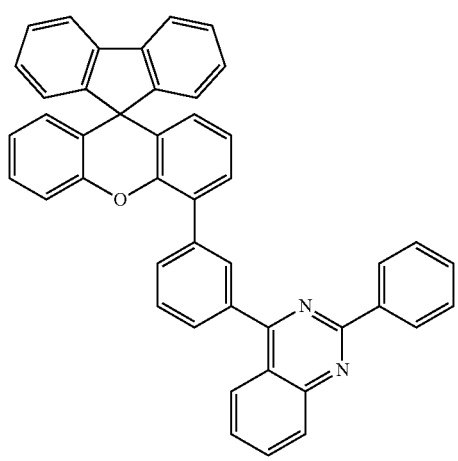
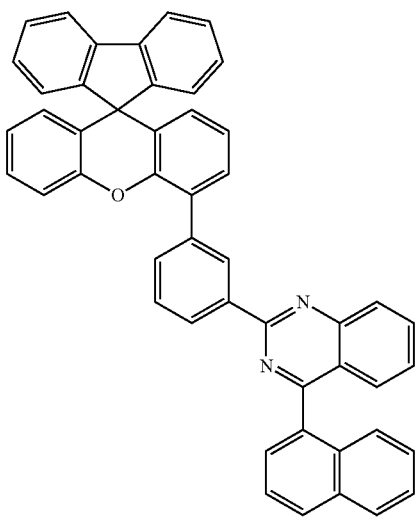
124
-continued
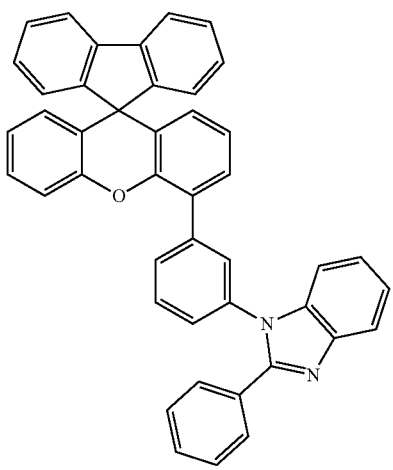
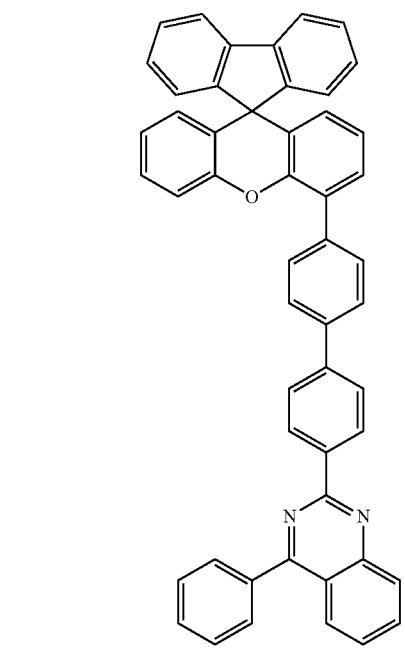
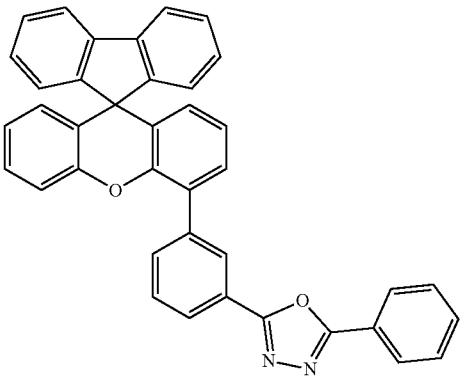

125
-continued
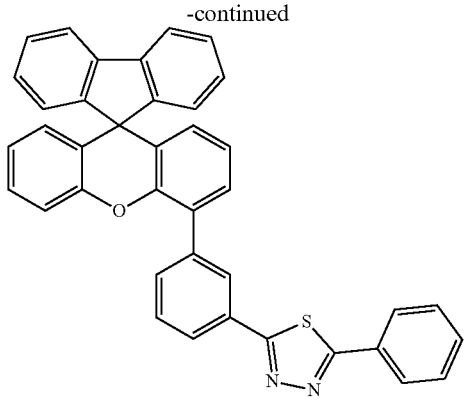
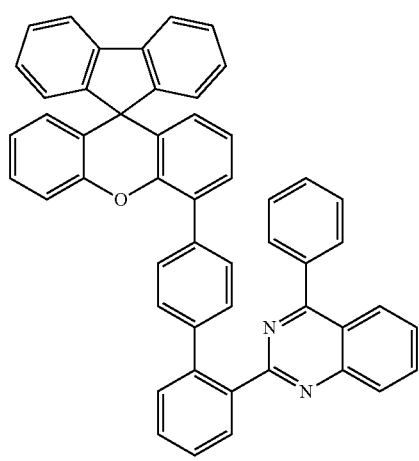
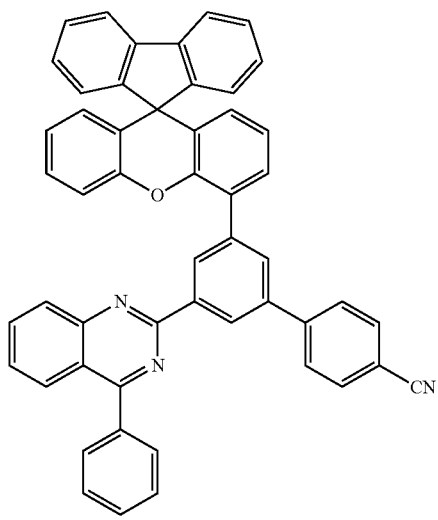
126
-continued
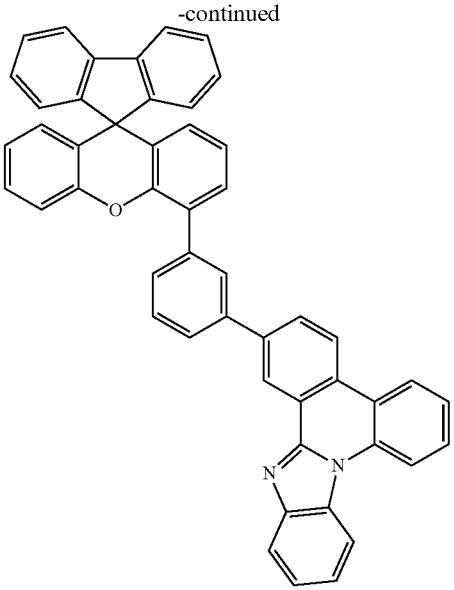
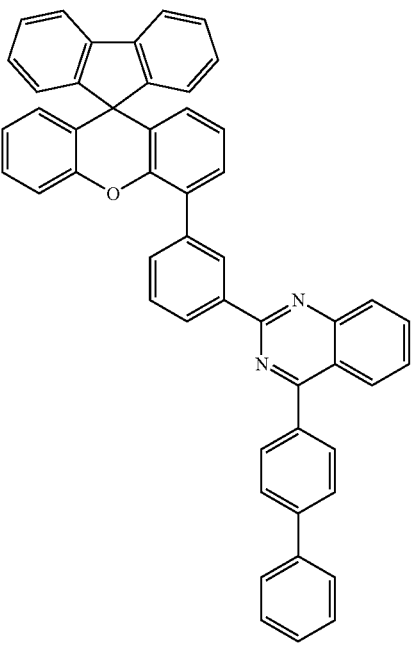

127
-continued
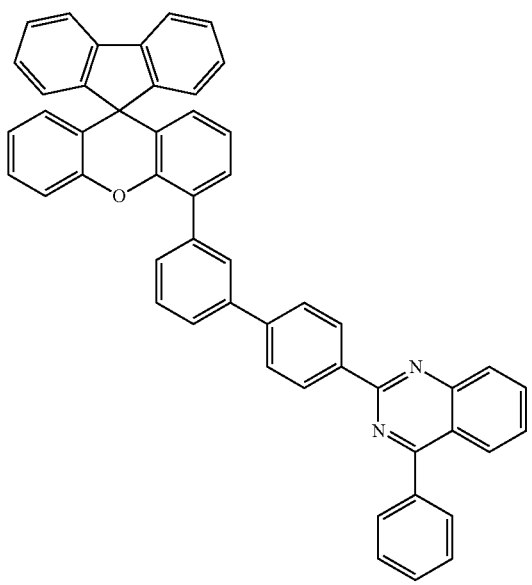
128
-continued
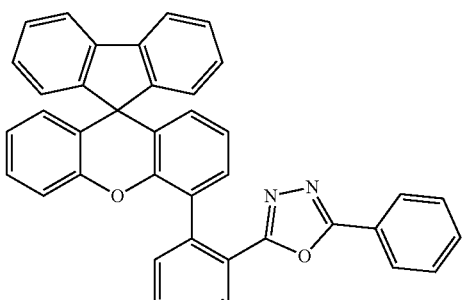
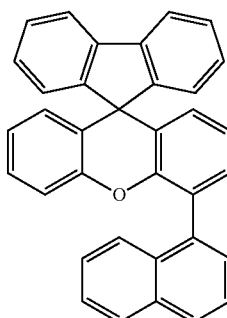
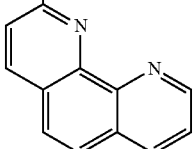
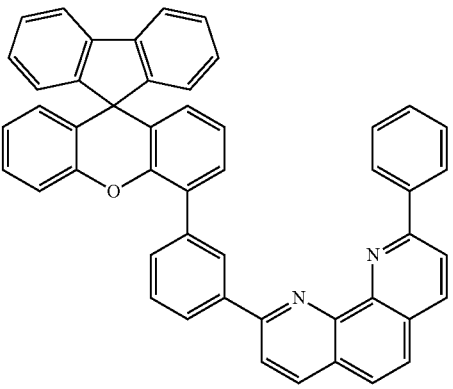
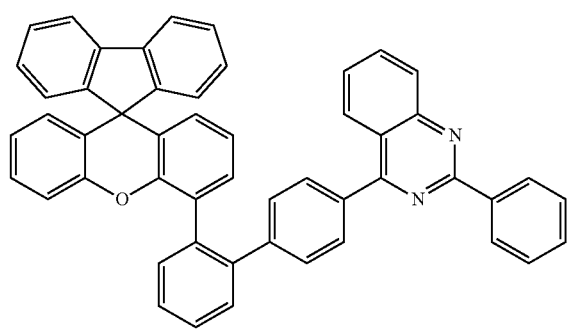
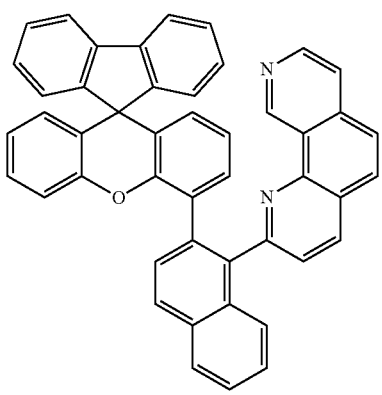

129
-continued

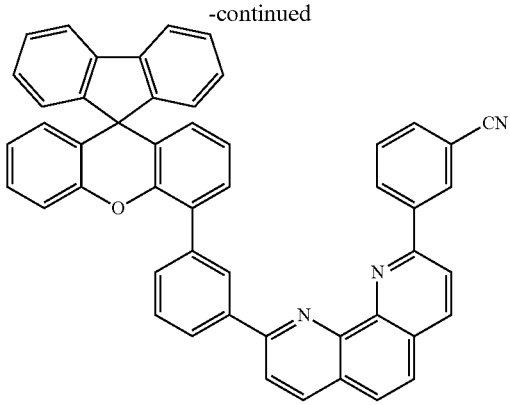

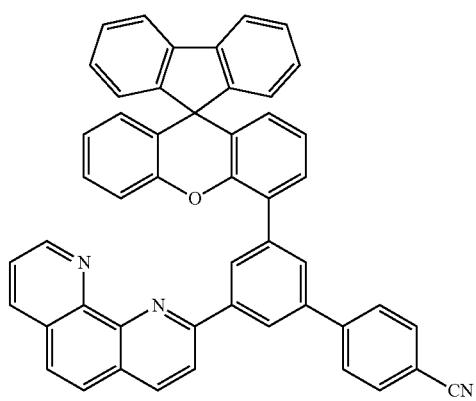

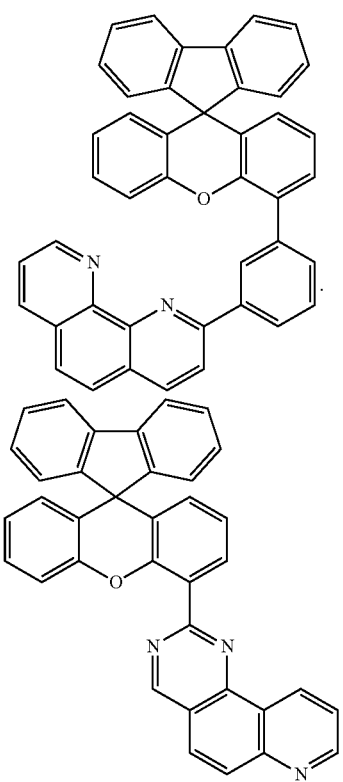

130
-continued

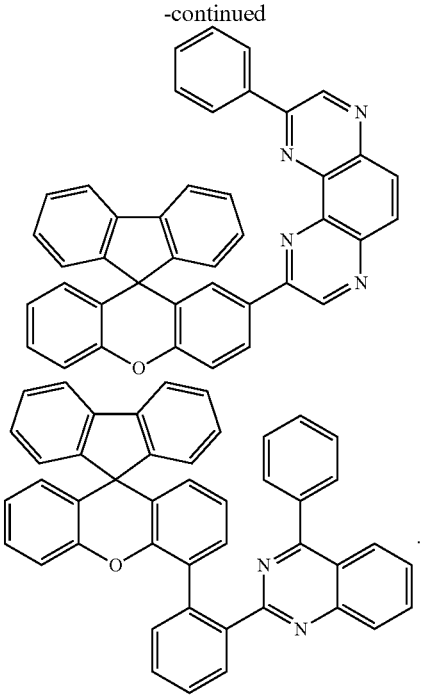

13. An organic light emitting device comprising:
   a first electrode;
   a second electrode provided opposite to the first electrode; and
   one or more organic material layers provided between the first electrode and the second electrode,
   wherein the heterocyclic compound of claim 1 is comprised in one or more layers of the one or more organic material layers.

14. The organic light emitting device of claim 13, wherein the heterocyclic compound is comprised in one or more layers of an electron injection layer, an electron transfer layer and a layer carrying out electron injection and electron transfer at the same time.

15. The organic light emitting device of claim 13, wherein the heterocyclic compound is comprised in an electron control layer.

16. The heterocyclic compound of claim 1, wherein L is a direct bond; or represented by any one of the following structural formulae:

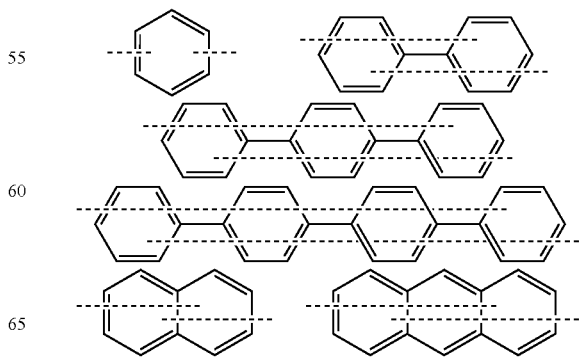

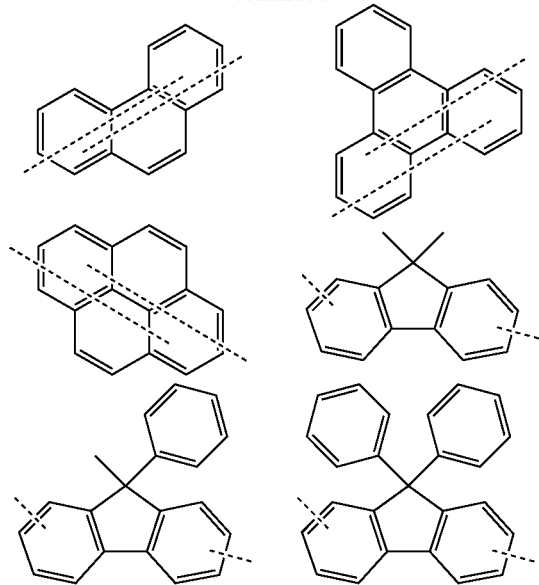
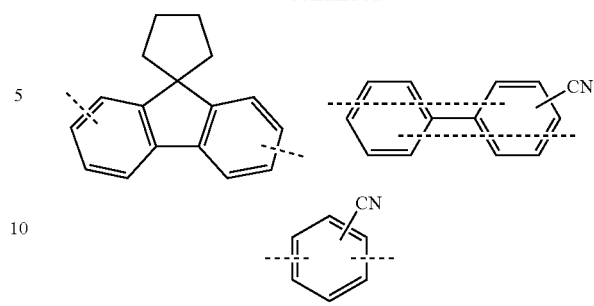
wherein is a site bonding to the main chain.
17. The organic light emitting device of claim 14, wherein the heterocyclic compound is further mixed with a n-type dopant.
18. The organic light emitting device of claim 17, wherein a weight ratio of the heterocyclic compound and the n-type dopant is from 1:100 to 100:1.
* * * * *

UNITED STATES PATENT AND TRADEMARK OFFICE
CERTIFICATE OF CORRECTION

| | | |
|---|---|---|
| PATENT NO. | : 11,450,819 B2 | Page 1 of 1 |
| APPLICATION NO. | : 16/484641 | |
| DATED | : September 20, 2022 | |
| INVENTOR(S) | : Dong Uk Heo et al. | |

It is certified that error appears in the above-identified patent and that said Letters Patent is hereby corrected as shown below:

On the Title Page

Item (71) Applicant: "LG Chern, Ltd., Seoul (KR)" should read -- LG Chem, Ltd., Seoul (KR) --.

Signed and Sealed this
First Day of November, 2022

Katherine Kelly Vidal
*Director of the United States Patent and Trademark Office*